(12) United States Patent
Burow et al.

(10) Patent No.: US 8,987,198 B2
(45) Date of Patent: Mar. 24, 2015

(54) COMPOSITIONS AND METHODS FOR TREATING OBESITY AND DIABETES

(75) Inventors: Matthew E. Burow, Slidell, LA (US); Stephen M. Boue, New Orleans, LA (US); Thomas T. Y. Wang, Beltsville, MD (US); Deepak Bhatnagar, New Orleans, LA (US); Charles E. Wood, Winston-Salem, NC (US); Mark L. Helman, New Orleans, LA (US)

(73) Assignees: The Administrators of the Tulane Educational Fund, New Orleans, LA (US); The United States Department of Agriculture, Washington, DC (US); Wake Forest University Health Sciences, Winston-Salem, NC (US); Nume Health, LLC, New Orleans, LA (US)

( * ) Notice: Subject to any disclaimer, the term of this patent is extended or adjusted under 35 U.S.C. 154(b) by 879 days.

(21) Appl. No.: 12/976,209

(22) Filed: Dec. 22, 2010

(65) Prior Publication Data

US 2011/0237505 A1    Sep. 29, 2011

Related U.S. Application Data

(60) Provisional application No. 61/284,623, filed on Dec. 22, 2009, provisional application No. 61/399,224, filed on Jul. 8, 2010.

(51) Int. Cl.
| | |
|---|---|
| *A61K 38/28* | (2006.01) |
| *A61K 38/00* | (2006.01) |
| *A61K 31/352* | (2006.01) |
| *A61K 31/52* | (2006.01) |

(52) U.S. Cl.
CPC .............. *A61K 31/352* (2013.01); *A61K 31/52* (2013.01); *A61K 38/28* (2013.01)
USPC ................ 514/6.5; 514/6.7; 514/6.8; 514/6.9

(58) Field of Classification Search
None
See application file for complete search history.

(56) References Cited

U.S. PATENT DOCUMENTS 7,101,544 B1 * 9/2006 Sawada et al. ............. 424/93.51
8,323,706 B2 * 12/2012 Cleveland et al. ............ 424/725

FOREIGN PATENT DOCUMENTS

KR    10-2009-0114001    11/2009

OTHER PUBLICATIONS

Boue et al. J Agric Food Chem 2012 60 6376-6382.*
J. Agric. Food Chem., 2007, 55 (20), pp. 7981-7994.*
Vital-Lopez et al. BMC systems biology 2013, 7:63 1-10.*
J. Nutr. Apr. 2006 vol. 136 No. 4 899-905.*
Kim, J-S, et al. "Regulation of Afipocyte Differentiation by Glyceollins", the FASEB Journal, 2009;23(1): 721-6.
Rochfort, S. et al. "Phytochemicals for health, the role of pulses", Journal of Agricultural and Food Chemistry, 2007;55(20): 7981-7994.
International Search Report of PCT/US2010-061887 mailed Aug. 18, 2011.
Written Opinion of PCT/US2010/061887 mailed Aug. 18, 2011.

* cited by examiner

*Primary Examiner* — James H Alstrum Acevedo
*Assistant Examiner* — Li Lee
(74) *Attorney, Agent, or Firm* — Miles & Stockbridge PC

(57) ABSTRACT

Disclosed are methods of modulating the expression of genes linked to adipocytokine signaling, carbohydrate metabolism, fatty acid metabolism, arachidonic acid metabolism, PPAR signaling, insulin signaling, lipid metabolism, extracellular matrix (ECM)-receptor interaction, or combinations thereof, methods of treating hyperlipidemia, obesity, excessive cholesterol, cardiovascular disease, liver disease, diabetes, or combinations thereof, and methods of stimulating glucose uptake in an animal in need thereof, comprising administering a composition comprising at least one isolated glyceollin to said animal.

9 Claims, 14 Drawing Sheets

*Sheet 1 / 14*
GENISTEIN 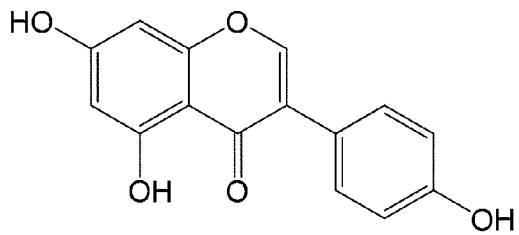
DAIDZEIN 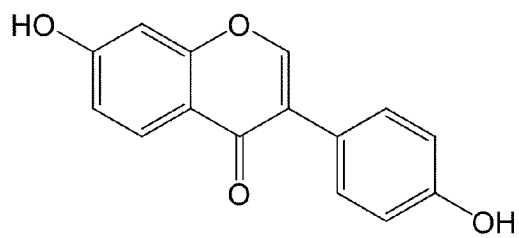
GLYCEOLLIN I 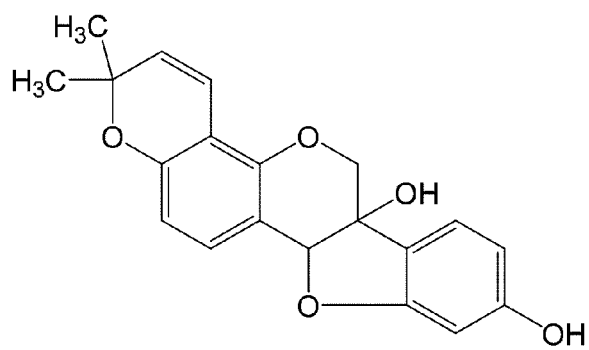
GLYCEOLLIN II 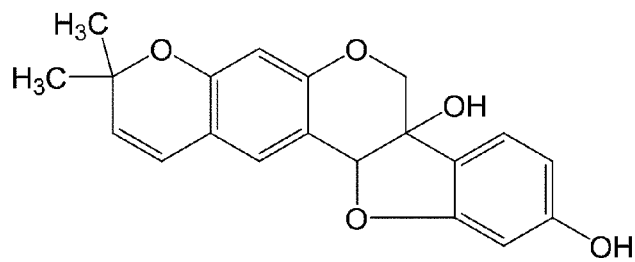
GLYCEOLLIN III 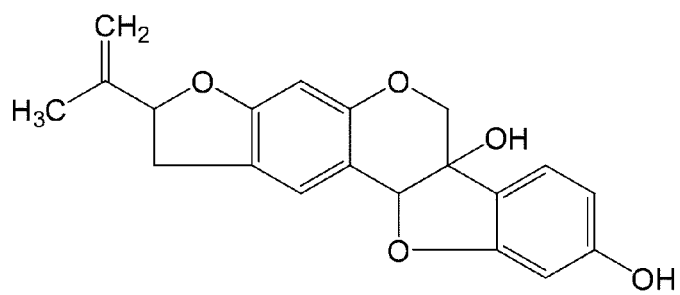
FIG. 1

| 1 | 2 | 3 | 4 | 5 | 6 |
|---|---|---|---|---|---|
| 10 µL tracer<br>990 µL KRH<br><br>*0 Insulin* | 10 µL tracer<br>990 µL KRH<br><br>*0 Insulin* | 10 µL tracer<br>990 µL KRH<br><br>*0 Insulin* | 10 µL tracer<br>890 µL KRH<br>100 µL Ins J<br><br>*0.03 nM Insulin* | 10 µL tracer<br>890 µL KRH<br>100 µL Ins J<br><br>*0.03 nM Insulin* | 10 µL tracer<br>890 µL KRH<br>100 µL Ins J<br><br>*0.03 nM Insulin* |
| 7 | 8 | 9 | 10 | 11 | 12 |
| 10 µL tracer<br>890 µL KRH<br>100 µL Ins I<br><br>*0.1 nM Insulin* | 10 µL tracer<br>890 µL KRH<br>100 µL Ins I<br><br>*0.1 nM Insulin* | 10 µL tracer<br>890 µL KRH<br>100 µL Ins I<br><br>*0.1 nM Insulin* | 10 µL tracer<br>890 µL KRH<br>100 µL Ins H<br><br>*0.3 nM Insulin* | 10 µL tracer<br>890 µL KRH<br>100 µL Ins H<br><br>*0.3 nM Insulin* | 10 µL tracer<br>890 µL KRH<br>100 µL Ins H<br><br>*0.3 nM Insulin* |
| 13 | 14 | 15 | 16 | 17 | 18 |
| 10 µL tracer<br>890 µL KRH<br>100 µL Ins G<br><br>*1 nM Insulin* | 10 µL tracer<br>890 µL KRH<br>100 µL Ins G<br><br>*1 nM Insulin* | 10 µL tracer<br>890 µL KRH<br>100 µL Ins G<br><br>*1 nM Insulin* | 10 µL tracer<br>890 µL KRH<br>100 µL Ins F<br><br>*3 nM Insulin* | 10 µL tracer<br>890 µL KRH<br>100 µL Ins F<br><br>*3 nM Insulin* | 10 µL tracer<br>890 µL KRH<br>100 µL Ins F<br><br>*3 nM Insulin* |
| 19 | 20 | 21 | 22 | 23 | 24 |
| 10 µL tracer<br>890 µL KRH<br>100 µL Ins E<br><br>*10 nM Insulin* | 10 µL tracer<br>890 µL KRH<br>100 µL Ins E<br><br>*10 nM Insulin* | 10 µL tracer<br>890 µL KRH<br>100 µL Ins E<br><br>*10 nM Insulin* | 10 µL tracer<br>890 µL KRH<br>100 µL Ins D<br><br>*30 nM Insulin* | 10 µL tracer<br>890 µL KRH<br>100 µL Ins D<br><br>*30 nM Insulin* | 10 µL tracer<br>890 µL KRH<br>100 µL Ins D<br><br>*30 nM Insulin* |

FIG. 7

| 1 | 2 | 3 | 4 | 5 | 6 |
|---|---|---|---|---|---|
| 10 µL tracer<br>990 µL KRH<br><br>*0 µM Gly* | 10 µL tracer<br>990 µL KRH<br><br>*0 µM Gly* | 10 µL tracer<br>990 µL KRH<br><br>*0 µM Gly* | 10 µL tracer<br>890 µL KRH<br>100 µL Gly I<br><br>*0.5 µM Gly* | 10 µL tracer<br>890 µL KRH<br>100 µL Gly I<br><br>*0.5 µM Gly* | 10 µL tracer<br>890 µL KRH<br>100 µL Gly I<br><br>*0.5 µM Gly* |
| 7 | 8 | 9 | 10 | 11 | 12 |
| 10 µL tracer<br>890 µL KRH<br>100 µL Gly H<br><br>*1 µM Gly* | 10 µL tracer<br>890 µL KRH<br>100 µL Gly H<br><br>*1 µM Gly* | 10 µL tracer<br>890 µL KRH<br>100 µL Gly H<br><br>*1 µM Gly* | 10 µL tracer<br>890 µL KRH<br>100 µL Gly G<br><br>*2 µM Gly* | 10 µL tracer<br>890 µL KRH<br>100 µL Gly G<br><br>*2 µM Gly* | 10 µL tracer<br>890 µL KRH<br>100 µL Gly G<br><br>*2 µM Gly* |
| 13 | 14 | 15 | 16 | 17 | 18 |
| 10 µL tracer<br>890 µL KRH<br>100 µL Gly F<br><br>*4 µM Gly* | 10 µL tracer<br>890 µL KRH<br>100 µL Gly F<br><br>*4 µM Gly* | 10 µL tracer<br>890 µL KRH<br>100 µL Gly F<br><br>*4 µM Gly* | 10 µL tracer<br>890 µL KRH<br>100 µL Gly E<br><br>*6 µM Gly* | 10 µL tracer<br>890 µL KRH<br>100 µL Gly E<br><br>*6 µM Gly* | 10 µL tracer<br>890 µL KRH<br>100 µL Gly E<br><br>*6 µM Gly* |
| 19 | 20 | 21 | 22 | 23 | 24 |
| 10 µL tracer<br>890 µL KRH<br>100 µL Gly D<br><br>*8 µM Gly* | 10 µL tracer<br>890 µL KRH<br>100 µL Gly D<br><br>*8 µM Gly* | 10 µL tracer<br>890 µL KRH<br>100 µL Gly D<br><br>*8 µM Gly* | 10 µL tracer<br>890 µL KRH<br>100 µL Gly C<br><br>*10 µM Gly* | 10 µL tracer<br>890 µL KRH<br>100 µL Gly C<br><br>*10 µM Gly* | 10 µL tracer<br>890 µL KRH<br>100 µL Gly C<br><br>*10 µM Gly* |

FIG. 8

COMPOSITIONS AND METHODS FOR TREATING OBESITY AND DIABETES

CROSS-REFERENCE TO RELATED APPLICATIONS

This application claims the benefit of U.S. Provisional Application No. 61/284,623, filed on Dec. 22, 2009, and of U.S. Provisional Application No. 61/399,224, filed on Jul. 8, 2010, each of which are hereby incorporated by reference in their entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON COMPACT DISC

Not applicable

BACKGROUND

1. Field

The present invention relates to the use of isoflavonoid phytoalexin compounds, Glyceollins I, II, and III, found in soy plants grown under stressed conditions, as a method of treating and/or preventing conditions such as hyperlipidemia, obesity, excessive cholesterol, cardiovascular diseases, diabetes, liver disease, and combinations thereof.

2. Description of Related Art

Obesity is reaching epidemic proportions in Western populations and is commonly attributed to the high fat consumption and the sedentary lifestyles of Western populations. It is a significant public health concern, being linked with diseases such as type 2 diabetes and cardiovascular disease. Visceral (central) obesity, in particular, is associated with insulin resistance, hyperglycaemia, hyperinsulinaemia, dyslipidaemia, hypertension, and prothrombotic and proinflammatory states. The term "metabolic syndrome" encompasses these biochemical abnormalities and clinical conditions that may or may not be associated with central obesity. Obesity is a disorder of energy balance and is associated with hyperinsulinemia, insulin resistance, and abnormalities in lipid metabolism. It is one of the most important risk factors in the development of Type II diabetes, cardiovascular disease, atherosclerosis, and certain cancers.

Because of the lower frequency of these diseases in Asian countries, attention has turned toward the Asian diet, which consists mostly of soy and soy-based food products. Adipocytes play a central role in lipid homeostasis and the maintenance of energy balance in vertebrate systems. Excess fat consumption can stimulate enlargement of existing adipocytes and induce differentiation of dormant preadipocytes into mature adipocytes. Hormones, including estradiol, are regulators of this process called adipogenesis. Soy isoflavones (also called phytoalexins) mimic certain estradiol effects by binding to estrogen receptors (ER) and thus altering adipogenesis. Adipogenesis is regulated by the peroxisome proliferator-activated receptor (PPAR-PPAR$\alpha$, PPAR$\beta$/$\delta$, and PPAR$\gamma$) families, the primary adipogenic transcription factors. Increasing evidence has established that soy isoflavones not only act through estrogen receptors but also exert effects through other pathways such as those regulated by PPARs.

Several researchers have shown that the isoflavone genistein (an ER agonist) can bind directly to and activate both PPAR$\alpha$ and PPAR$\gamma$. In the liver, activation of PPAR$\alpha$ leads to increased $\beta$-oxidation of fatty acids, decreased triglyceride (TG), and very low density lipoprotein (VLDL) synthesis. It is generally accepted that the majority of the effects of the soy isoflavone genistein are mediated by changes in the expression of genes involved in cholesterol metabolism. Genistein exerts antidiabetic and hypolipidimic effects through upregulation of PPAR-regulated genes. However, little is known about the effect of genistein and other phytoalexins or phytoalexin isoflavone metabolites on fatty acid synthesis or other aspects of lipid metabolism.

The liver X receptors (LXR$\alpha$ and LXR$\beta$) are additional members of the nuclear receptor superfamily that were originally identified as orphan receptors. These two receptors play a key role in the regulation of cholesterol metabolism and transport as well as glucose metabolism and inflammation. The liver X receptors (LXRs) are nuclear receptors that play central roles in the transcriptional control of lipid metabolism. LXRs function as nuclear cholesterol sensors that are activated in response to elevated intracellular cholesterol levels in multiple cell types. Once activated, LXRs induce the expression of an array of genes involved in cholesterol absorption, efflux, transport, and excretion. In addition to their function in lipid metabolism, LXRs have also been found to modulate immune and inflammatory responses in macrophages. The modulation of the activity of LXR receptors may be useful in the treatment of a number of pathophysiological states including dyslipidemia, atherosclerosis, and diabetes.

Synthetic LXR agonists promote cholesterol efflux and inhibit inflammation in vivo and inhibit the development of atherosclerosis in animal models. The ability of LXRs to integrate metabolic and inflammatory signaling makes them particularly attractive targets for intervention in human metabolic disease. There is still considerable debate whether selective activation of LXR$\alpha$ or LXR$\beta$ has a differential effect on cholesterol homeostasis or whether they exist as functionally redundant paralogs (X,Y). Studies using LXR$\alpha$/$\beta$ null mice suggest that the regulation of genes in liver and peripheral tissue involved in cholesterol homeostasis is primarily under the control of LXR$\alpha$, and activation of LXR$\beta$ can partially rescue LXR$\alpha$ null animals from gross peripheral cholesterol accumulation. However, outside of its role in cholesterol efflux, the broader biological functions of LXR$\beta$ are emerging, yet remain unclear. Unlike ABCG1 mRNA expression, which seems to be exclusively under the transcriptional control of LXR$\alpha$, ABCA1 mRNA in a number of cell types is regulated through signaling mechanisms independent of both LXR isotypes and its role in cholesterol transport. Despite this, measuring ABCA1 mRNA changes is often used as a surrogate marker for in vitro and in vivo LXR activation.

The liver is an important organ in the metabolism of lipids, carbohydrates, and proteins. Therefore, it is an attractive target organ in the study of obesity. Other tissues can also be analyzed for gene expression including mammary tissue. In primate animal model gene expression of mammary tissue was performed from oral treatments of soy protein isolate (combined with estradiol) with glyceollin-enriched soy protein isolate (combined with estradiol). Little is known about the alteration of genes in animal systems through the oral application of the glyceollins.

Of potential interest among the diet-derived compounds are the isoflavones, including genistein and daidzein that are rich in soy products. The isoflavones are also known as phytoalexins. Phytoalexins constitute a chemically heterogeneous group of low molecular weight antimicrobial compounds that are synthesized de novo and accumulate in plants in response to stress. Soy contains several phytoalexins including the constitutive isoflavones daidzein and genistein that are considered as candidates for diet-derived obesity preventive compounds. Initial interest in these compounds arose from studies that correlate consumption of soy products in Asian countries with a decreased incidence of obesity. Hence, a possible use for these compounds in obesity prevention has been suggested.

Dietary factors have been increasingly implicated in the etiology of a variety of chronic diseases. Much recent interest has focused on the role of specific bioactive components, particularly from dietary plants, in prevention or treatment of these diseases. Isoflavonoids are an important class of bioactive phytochemicals widely consumed as part of soy-based foods. Soy protein is rich in the glycosylated forms of the isoflavones genistein and daidzein, which have structural similarities to endogenous estrogens and exhibit a variety of biological functions relevant to human health. Recent evidence indicates that isoflavone metabolites may also mediate certain health-related effects of soy foods. The best-studied example is equol, which is formed from daidzein by gut bacteria in a subset of human soy consumers and various non-human species. Under the influence of stressors such as trauma or infection, daidzein may also be metabolized within soybeans to a unique class of defensive compounds called glyceollins. Prior studies have shown that glyceollins exhibit distinct effects compared with genistein and daidzein, including modulation of estrogen receptor (ER) signaling. Effects of glyceollins on other biological pathways and systems have not been investigated, however. The inventors evaluated the short-term effects of glyceollin-enriched soy protein on gene expression profiles in mammary adipose tissue. The inventors identified candidate target pathways of glyceollins and evaluated comparative effects of glyceollin-enriched soy protein with a standard soy protein isolate.

Diet is a major determinant of metabolic syndrome and related comorbid conditions, and prior findings suggest that glyceollins may competitively bind estrogen receptors (ERs) and elicit selective ER-modulating properties distinct from soy isoflavonoids. The role of specific isoflavonoids and their derivatives in modulating metabolic pathways remains poorly understood.

Gene expression DNA microarrays have provided medical researchers with a powerful tool to study the mechanisms of complex diseases such as obesity. This technology permits a more comprehensive understanding of multiple genes involved in the mechanisms behind both physiologic and pathologic conditions. Microarrays facilitate the classification of disease states according to the changes in the mRNA expressed in different cells or tissues. Gene expression profiling is the major application of DNA microarrays in the research of obesity in both animals and humans. Subcutaneous fat, visceral fat, adipocyte and preadipocyte, muscle, liver, pancreas, and cancer cells under normal and disease conditions are used in addressing the profile of gene expression in obesity.

Other research has revealed that some phytoalexins, including resveratrol, delay several diseases of ageing including cancer, atherosclerosis, Type II diabetes and even neurodegeneration. Considering the beneficial health effects of the phytoalexin resveratrol, it is reasonable to propose that other plant phytoalexins have similar beneficial activities. Most current food research based on legumes has focused on plant compounds that are constitutive; however plant food items may also contain thousands of phytoalexin compounds not present in current foods. In the legume family alone there are over two hundred phytoalexins with possible underutilized preventive benefits related to obesity. These compounds have the potential to create novel phytoalexin-enriched foods that would target and enhance obesity prevention.

In addition to genistein and daidzein, the glyceollins represent another group of phytoalexins whose biosynthesis is increased in response to stress signals. The glyceollin isomers I-III (FIG. 1) are derived from the precursor daidzein and exhibit core structures similar to that of coumestrol. The glyceollins (I-III) can be derived from exposure of soybean to the fungus *Aspergillus sojae*, a nontoxin-producing *Aspergillus* strain commonly used in the fermentation of soybeans to produce soy sauce and miso. Compared with genistein and daidzein, purified glyceollins show greater ability to modulate the activity of certain genes, including LXR receptors. These findings suggest that soy protein enriched with glyceollins may have distinct gene-modulating properties compared with standard soy protein.

There is a need to develop new treatments for obesity from both synthetic and natural sources. Thus, in view of the glyceollins' modulatory effects on pathways involved in lipid and carbohydrate metabolism, including PPAR and adipocytokine signaling, lipoprotein lipase, triglyceride metabolism, and LXRs in vitro, and further in view of their lack of toxic activity, the efficacy of glyceollins as a novel obesity therapy in vivo was studied.

BRIEF SUMMARY OF THE INVENTION

The present invention relates to glyceollins isolated from elicited soy which have been discovered to have modulatory effects on pathways involved in lipid and carbohydrate metabolism, including PPAR and adipocytokine signaling, lipoprotein lipase, and triglyceride metabolism, and on LXRs. These glyceollins thus would be useful in the prevention and treatment of obesity, and cardiovascular diseases.

In accordance with this discovery, it is an object of the invention to provide isolated glyceollins (Glyceollin I, II, and III) from elicited soy.

It is a further object of the invention to provide a composition containing glyceollin for preventing or minimizing obesity.

It is another object of the invention to provide a method for lowering serum total cholesterol, specifically non-high-density lipoprotein cholesterol.

It is another object of the invention to provide a method for preventing or minimizing diabetes.

It is another object of the invention to provide a method for preventing or minimizing dyslipidemia.

It is another object of the invention to provide a method for preventing or minimizing atherosclerosis.

It is another object of the invention to provide a method for preventing and treating cardiac and vascular diseases linked to obesity and hyperlipidemia.

It is another object of the invention to provide a method for preventing, minimizing, or ameliorating diabetes.

Also part of this invention is a kit, comprising a glyceollin-containing composition for preventing or minimizing obesity, for lowering serum total cholesterol, specifically non-high-density lipoprotein cholesterol, or for preventing, minimizing, or ameliorating diabetes.

Also part of this invention is a kit, comprising a glyceollin-containing composition for preventing or minimizing obesity, dyslipidemia, atherosclerosis, or diabetes.

Further information on uses for glyceollins is disclosed in U.S. patent application Ser. No. 11/118,431, published as US 2006/0246162, the disclosure of which is hereby incorporated by reference.

Provided is a method of modulating the expression of genes linked to adipocytokine signaling, carbohydrate metabolism, fatty acid metabolism, arachidonic acid metabolism, PPAR signaling, insulin signaling, lipid metabolism, extracellular matrix (ECM)-receptor interaction, or combinations thereof, in an animal, comprising administering to said animal a composition comprising at least one isolated glyceollin. The at least one isolated glyceollin may be isolated from elicited soy, and may be glyceollin I, glyceollin II, glyceollin III, or combinations thereof. The at least one isolated glyceollin may be provided in an amount of from about 100 nM to about 50 μM. The at least one isolated glyceollin may be provided in an amount of from about 1 mg/kg/animal to about 100 mg/kg/animal. The genes may be upregulated, relative to an animal that has not been administered said composition comprising at least one isolated glyceollin, and may be selected from the group consisting of: ADIPOQ; DGAT2; GPD1; GYS1; LEP; LPIN1; LPL; PLIN; PPARG; and combinations thereof. The genes may be upregulated, relative to an animal that has not been administered said composition comprising at least one isolated glyceollin, and may be selected from the group consisting of: ACACB; ACAT 1; ACOX1; AGPAT 2; AHSG; AKT1; AKT2; CAP1; CD36; CEBPB; CRK; DBI; EIF2B1; EIF4EBP1; FBP1; FOS; GPD1; GPAM; HADH; HRAS1; ITGA7; LPL; MAP2K1; ORM1; PLIN; PRKAR2B; PTGDS; PTPN1; PTPN11; SORBS1; SREBF1; VEGFA; and combinations thereof. The genes may be downregulated, relative to an animal that has not been administered said composition comprising at least one isolated glyceollin, and may be selected from the group consisting of: AEBP1; ARAF; CBL; CEBPA; CEBPD; CSN2; DOK2; DOK3; EIF4E; FRS3; G6PC; GCG; GCK; GPD2; GRB10; GRB2; GSK3B; IGF2; INS1; ITGA2; ITGA8; LDLR; NCK2; NOS2; NPY; OLR 1; PHIP; PIK3CA; PIK3R2; PPP1CA; PRKCI; PTPRF; RETN; SDC1; SHC3; SLC27A4; and combinations thereof.

Provided is a method of treating hyperlipidemia, obesity, excessive cholesterol, cardiovascular disease, liver disease, diabetes, or combinations thereof, in an animal in need thereof, comprising administering a composition comprising at least one isolated glyceollin to said animal. The at least one isolated glyceollin may be isolated from elicited soy, and may be glyceollin I, glyceollin II, glyceollin III, or combinations thereof. The at least one isolated glyceollin may be provided in an amount of from about 100 nM to about 50 μM. The at least one isolated glyceollin may be provided in an amount of from about 1 mg/kg/animal to about 100 mg/kg/animal. The method may further comprise increasing the expression in said animal of genes selected from the group consisting of: ADIPOQ; DGAT2; GPD1; GYS1; LEP; LPIN1; LPL; PLIN; PPARG; and combinations thereof, relative to an animal that has not been administered said composition comprising at least one isolated glyceollin. The method may further comprise lowering total cholesterol (TC), lowering low-density lipoprotein (LDL) cholesterol and very low density lipoprotein (VLDL) cholesterol, raising triglycerides (TG), or combinations thereof in said animal, relative to an animal that has not been administered said composition comprising at least one isolated glyceollin. The method may further comprise increasing the expression in said animal of genes selected from the group consisting of: ACACB; ACAT 1; ACOX1; AGPAT 2; AHSG; AKT1; AKT2; CAP1; CD36; CEBPB; CRK; DBI; EIF2B1; EIF4EBP1; FBP1; FOS; GPD1; GPAM; HADH; HRAS1; ITGA7; LPL; MAP2K1; ORM1; PLIN; PRKAR2B; PTGDS; PTPN1; PTPN11; SORBS1; SREBF1; VEGFA; and combinations thereof, relative to an animal that has not been administered said composition comprising at least one isolated glyceollin. The method may further comprise decreasing the expression in said animal of genes selected from the group consisting of: AEBP1; ARAF; CBL; CEBPA; CEBPD; CSN2; DOK2; DOK3; EIF4E; FRS3; G6PC; GCG; GCK; GPD2; GRB10; GRB2; GSK3B; IGF2; INS1; ITGA2; ITGA8; LDLR; NCK2; NOS2; NPY; PHIP; PIK3CA; PIK3R2; PPP1CA; PTPRF; RETN; SDC1; SHC3; SLC27A4; and combinations thereof, relative to an animal that has not been administered said composition comprising at least one isolated glyceollin.

A method of stimulating glucose uptake in an animal in need thereof is provided, comprising administering a composition comprising at least one isolated glyceollin to said animal. The at least one isolated glyceollin may be isolated from elicited soy, and may be glyceollin I, glyceollin II, glyceollin III, or combinations thereof. The at least one isolated glyceollin may be provided in an amount of from about 100 nM to about 50 μM. The at least one isolated glyceollin may be provided in an amount of from about 1 mg/kg/animal to about 100 mg/kg/animal. The composition may further comprise insulin, or a further composition comprising insulin may also be administered to said animal.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

FIG. 1 shows the structures of the soy isoflavone phytoalexins genistein, daidzein, glyceollin I, glyceollin II, and glyceollin III.

As shown in FIG. 2, results from LNCaP cell suggest a role for the glyceollins on LXR. Glyceollin treatment at 5 μM for 48 h led to an 8.1 fold up-regulation of ABCG1 (*=p<0.01).

FIG. 4.

FIG. 7 shows a challenge map for the plates used with the insulin stimulation experiments of EXAMPLE 11.

FIG. 8 shows a challenge map for the plates used with the glyceollin incubation experiments of EXAMPLE 12.

DETAILED DESCRIPTION

Figure 2:
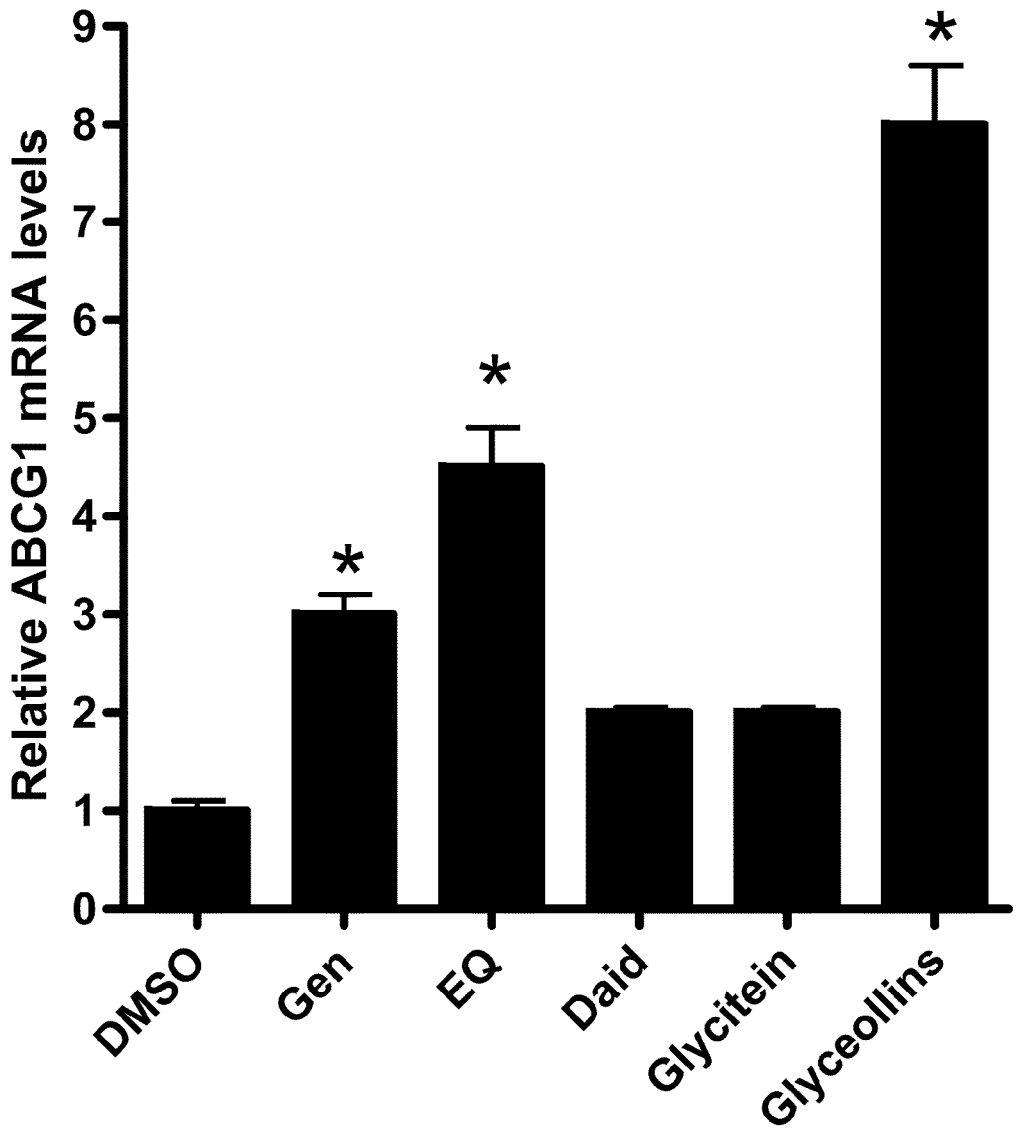
FIG. 2 demonstrates the effect of glyceollins on upregulation of ABCG1, a gene which is involved in cholesterol efflux by Liver X Receptor in LNCaP Cells in vitro; ABCG1 is a LXR-responsive gene that functions as a cholesterol efflux pump.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

Other than in the operating examples, or where otherwise indicated, all numbers expressing quantities of ingredients, reaction conditions and so forth used in the specification and claims are to be understood as being modified in all instances by the term "about". Accordingly, unless indicated to the contrary, the numerical parameters set forth in the instant specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the instant disclosure are approximations, the numerical values set forth in the specific examples are reported as precisely as possible. Any numerical values, however, inherently contain certain errors necessarily resulting from the standard deviation found in their respective testing measurements.

It should also be understood that any numerical range recited herein is intended to include all sub-ranges subsumed therein. For example, a range of 1" to 10" is intended to include all sub-ranges between and including the recited minimum value of 1 and the recited maximum value of 10, that is, having a minimum value equal to or greater than 1 and a maximum value of equal to or less than 10.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

As used herein, the term "minimize" or "reduce", or a variant thereof, includes a complete or partial inhibition of a specified biological effect (which is apparent from the context in which the term minimize is used). The term "glyceollin" may mean both a single glyceollin and plural glyceollins when the glyceollin is defined as at least one of a selected group of glyceollins.

This disclosure describes, inter alia, the increased biosynthesis of the isoflavonoid phytoalexin compounds, Glyceollins I, II and III, in soy plants grown under stressed conditions (elicited soy) and their marked effects on LXRα and/or LXRβ function, pathways involved in lipid and carbohydrate metabolism, including PPAR and adipocytokine signaling, lipoprotein lipase, and triglyceride metabolism. To fully understand the role of glyceollins' role in liver function, the well-established model of LNCaP cancer cells in an in vitro model was used to examine the effects of glyceollins on selective gene expression. In this model, using the LNCaP cancer cells, the in vitro activity of the glyceollins on LXRα or LXRβ has been established.

The glyceollin compounds used in the compositions and methods of the present invention are naturally occurring substances which may be found in plants such as soybeans that are stressed or that have been treated with elicitors. The glyceollin compounds may be isolated from the plant sources in which they naturally occur after treatment with an elicitor, or may be synthetically prepared by processes known in the art.

It is preferred to extract the glyceollins useful in the compositions and methods of the present invention from the plant materials in which they naturally occur. A preferred method of isolating the glyceollin compounds is to extract the plant materials with an alcohol, preferably methanol or ethanol, or an aqueous methanolic solution, to remove the glyceollins from the plant material. It is preferred to comminute the plant material before extracting the glyceollin compounds to maximize recovery of glyceollin compounds from the plant material. The glyceollin compounds are isolated from the extract by conventional separation procedures, such as high performance liquid chromatography, HPLC.

In a preferred embodiment, the glyceollin compounds are isolated from a soy material. Soy materials from which the glyceollin compounds can be isolated include elicitor-treated: soy seeds, soybeans, dehulled soybeans, soy cotyledeons, soy leaf tissue, soy roots, and soy hypocotyls. In one embodiment, the glyceollins are extracted from soy seeds, with a low molecular weight organic extractant, preferably an alcohol, ethyl acetate, acetone, or ether, and most preferably aqueous ethyl alcohol or methyl alcohol.

The present disclosure demonstrates that specific glyceollins, isolated from elicited soy, displayed modulatory effect on pathways involved in lipid and carbohydrate metabolism, including PPAR and adipocytokine signaling, lipoprotein lipase, and triglyceride metabolism in vivo, as well as on LXRα or LXRβ in vitro. The modulatory effects of the glyceollins (glyceollin I, glyceollin II, glyceollin II, or combinations thereof) can be observed at between about 0.5 and about 10 µM, about 0.5 and about 5.0 µM, about 0.5 and about 1.0 µM, about 1.0 and about 10 µM, about 1.0 and about 5 µM, about 5.0 and about 10 µM, and preferably about 5.0 µM. The modulatory effects of the glyceollins on LNCaP cells were similar to that observed for genistein (FIG. 1). The glyceollins (glyceollin I, glyceollin II, glyceollin II, or combinations thereof) can be provided to, administered to, or consumed by an animal in an amount of greater than zero mg/kg to about 100 mg/kg, about 0.1 mg/kg to about 90 mg/kg, about 0.1 mg/kg to about 80 mg/kg, about 0.1 mg/kg to about 75 mg/kg, about 0.1 mg/kg to about 70 mg/kg, about 0.1 mg/kg to about 60 mg/kg, about 0.1 mg/kg to about 50 mg/kg, about 0.1 mg/kg to about 40 mg/kg, about 0.1 mg/kg to about 30 mg/kg, about 0.1 mg/kg to about 25 mg/kg, about 0.1 mg/kg to about 20 mg/kg, about 0.1 mg/kg to about 15 mg/kg, about 0.1 mg/kg to about 10 mg/kg, about 0.1 mg/kg to about 5 mg/kg, about 0.1 mg/kg to about 2.5 mg/kg, about 0.1 mg/kg to about 1 mg/kg, about 1 mg/kg to about 100 mg/kg, about 2.5 mg/kg to about 90 mg/kg, about 5 mg/kg to about 80 mg/kg, about 7.5 mg/kg to about 75 mg/kg, about 10 mg/kg to about 60 mg/kg, about 20 mg/kg to about 50 mg/kg, about 25 mg/kg to about 40 mg/kg, about 25 mg/kg to about 35 mg/kg, and preferably about 30 mg/kg per animal.

Materials and Methods: Liver X Receptors
Chemicals

Dihydrotestosterone (DHT), dimethylsulfoxide (DMSO), and genistein, 17β-estradiol were from Sigma Chemical Co. (St. Louis, Mo.). Cell culture media and reagents were purchased from Invitrogen (Carlsbad, Calif.).

Soybean Treatment and Harvesting

*Aspergillus sojae* (SRRC 1125) cultures were grown at 25° C. in the dark on potato dextrose agar. After 5 days, inoculum was prepared by harvesting conidia ($3.4 \times 10^7$/ml) in 15 ml sterile, distilled $H_2O$. Seeds from commercial soybean variety Asgrow 5902 were surface-sterilized for 3 min in 70% ethanol followed by a quick deionized-$H_2O$ rinse and two 2 min rinses in deionized-$H_2O$. Seeds were presoaked in sterile deionized-$H_2O$ for 4-5 hr, and then chopped for 2 min in a Cuisinart food processor. *Aspergillus sojae* spore suspension (300 ml) was applied to the cut surface of seeds on each tray. All trays were stored at 25° C. in the dark for three days, rinsed with water to remove spores, and oven dried at 40° C. for 24 hrs. Seeds were ground using a Waring blender before extraction.

Isolation of Glyceollins (I-III)

The glyceollins I, II, and III were extracted from the 300 g ground seeds with 1 L methanol. The glyceollins were isolated using preparative scale HPLC using two Waters 25 mm 10 mm particle size mBondapak C18 radial compression column segments combined using an extension tube. HPLC was performed on a Waters 600E System Controller combined with a Waters UV-VIS 996 detector. Elution was carried out at a flow rate of 8.0 ml/min with the following solvent system: A=acetonitrile, B=water; 5% A for 10 min, then 5% A to 90% A in 60 min followed by holding at 90% A for 20 min. The injection volume was 20 mL. The fraction containing the glyceollins was concentrated under vacuum and freeze-dried. The glyceollins were confirmed by UV-VIS spectrophotometry, mass spectrometry, and NMR. The solvents acetonitrile (HPLC grade) and methanol were purchased from Aldrich Chemical Company. Water was obtained using a Millipore system and used during sample preparation procedures and HPLC analyses. A mixture of glyceollins I (68%), II (21%), and III (11%) were isolated (see FIG. 1) and used in treatments. An average MW of 338 was use to calculate the concentration of glyceollins used in all cell culture experiments.

Cells and Cell Culture

LNCaP cells were obtained from the American Type Culture Collection (Manassas, Va.) and maintained in Media A [RPMI 1640 medium with phenol red (Invitrogen, Carlsbad, Calif.), 2 mM L-glutamine (Sigma), 100 U/mL penicillin and 100 µg/mL streptomycin (BioSource International, Camarillo, Calif.) with 10% fetal bovine serum (FBS) (Invitrogen, Carlsbad, Calif.)]. Cells were incubated in the presence of 5% $CO_2$ in air at 37° C.

Gene SuperArrays with MCF-7 Cells In Vitro.

MCF-7 cells were seeded into 75 cm2 flasks in DMEM media supplemented with 5% fetal bovine serum. On the following day media was replaced with phenol-red free DMEM supplemented with 5% charcoal stripped serum for 2 days. Cells were treated with DMSO (vehicle), 1 nM 17β-estradiol, 10 µM glyceollin mixture and 100 nM tamoxifen. Total RNA was extracted. Each array profiles the expression of a panel of 96 genes. For each array, 4 µg RNA was reverse transcribed into cDNA in the presence of gene-specific oligonucleotide primers as described in the manufacturer's protocol. cDNA template was mixed with the appropriate ready-to-use PCR master mix, equal volumes were aliquoted to each well of the same plate, and then the real-time PCR cycling program was run. Quantitative RT-PCR and Estrogen Receptor Signaling Superarray, Gaithersburg, Md., USA). Relative gene expressions were calculated by using the $2^{-\Delta\Delta Ct}$ method, in which Ct indicates the fractional cycle number where the fluorescent signal reaches detection threshold. The 'delta-delta' method (which is described by Pfaffl et al.,) uses the normalized ΔCt value of each sample, calculated using a total of five endogenous control genes (18S rRNA, HPRT1, RPL13A, GAPDH, and ACTB). Fold change values are then presented as average fold change=$2-(^{average\ \Delta\Delta Ct})$ for genes in treated relative to control samples. Clinical variables were characterized using descriptive statistics, and the statistical significance of differences in gene expression between groups was calculated using the student's t-test.

Primate Study and Diets

The inventors used 30 adult female surgically menopausal cynomolgus macaques (*Macaca fascicularis*) with an average age of 17.8±0.5 years. All animals had been ovariectomized for 4 yr and housed since that time in stable social groups of three to four animals each. These animals were previously enrolled in a randomized Latin-square crossover study evaluating soy isoflavone effects when given with either trace or low-dose oral estradiol. In this previous study, each social group of animals received the same experimental treatments but in a different sequence. No significant carryover effects were found for any breast endpoints across the 4-wk washout periods between treatment phases. The estradiol doses used in the previous study (equivalent to 0.09 or 0.5 mg/day in women) were less than those typically prescribed to postmenopausal women for hormone therapy (~1.0 mg/day), and the isoflavone doses (equivalent to 0, 60, 120, or 240 mg/day in women) were within the range of human dietary or supplement exposure. There is no evidence that this level of estrogen or isoflavone exposure alters the subsequent hormonal response of the adult mammary gland. For the current study, the monkeys all received a control casein/lactalbumin-based diet for 6 wk before the start of the experiment. Animals were then randomized by social group to receive one of three diets containing the following: 1) estradiol (E2, 1 mg/1,800 kcal)+casein/lactalbumin [control (Con), n=9]; 2) E2+soy protein isolate (SPI) containing 193.6 mg/1,800 kcal isoflavonoids (n=11); and 3) E2+glyceollin-enriched soy protein (GLY) containing 188.5 mg/1,800 kcal isoflavonoids and 134.1 mg/1,800 kcal glyceollins (n=10). The control diet contained a trace amount of soy protein delivering 6.7 mg/1,800 kcal isoflavonoids. All isoflavonoid doses are expressed in aglycone equivalents. Diets were isocaloric and similar in macronutrients, cholesterol, calcium, and phosphorus. The glyceollin-enriched protein was produced by enzymatic treatment of scarred soybeans (Glycine max) to induce conversion of the parent isoflavone daidzein to glyceollins. The beans were then ground, defatted, and incorporated into a fiber concentrate. The GLY supplement contained 959.5 μg of unconjugated glyceollins per gram of product (76.8% glyceollin I, 9.9% glyceollin II, and 13.6% glyceollin III), as determined by high-pressure liquid chromatography (HPLC) and ultraviolet (UV) monitoring (visible spectrophotometry). Glyceollin HPLC analyses were performed on a Waters 600E System Controller combined with a UV-VIS 996 detector. Glyceollins were extracted and homogenized in 0.5 ml 80% EtOH, heated at 50° C. for 1 h, cooled, centrifuged at 14,000 g for 10 min, and filtered. An aliquot (20 μl) of supernatant was directly analyzed by HPLC. Glyceollins were monitored at a wavelength of 285 nm, and separations were carried out using a Vydac Multiring C18 (4.6×250 mm; 5 μm) reverse-phase column. Elution was carried out at a flow rate of 1.0 ml/min using a standard solvent system. All HPLC analyses were run in triplicate. Relative isoflavonoid content was also measured per 75 units as 61.5% genistein, 34.6% daidzein, and 3.8% glyceitein for the soy protein isolate and 52.6% genistein, 43.0% daidzein, and 4.4% glyceitein for the glyceollin-enriched protein. To balance the diets, a fiber concentrate (FIBRIM 2000®) was added to the control and SPI diets. This concentrate contained a small amount of soy protein (11.4% by weight) providing 0.17 mg isoflavonoids per gram of product (as measured by HPLC). The soy protein isolate and fiber concentrate were generously provided by Solae, a division of Dupont (St. Louis, Mo.). The glyceollin-enriched protein was provided through collaborative efforts of Solae; the Southern Regional Research Center, United States Department of Agriculture; and the Tulane University School of Medicine. Estradiol tablets were obtained from Mylan Pharmaceuticals (Morganton, W. Va.). Animals were fed approximately 120 kcal/kg body weight (BW) once daily. Daily doses of estradiol, isoflavonoids, and glyceollins were scaled to 1,800 kcal of diet (the estimated daily intake for a U.S. woman) to account for differences in metabolic rates between the monkeys and human subjects. Monkeys were thus given 66.7 μg of E2/kg BW (all groups); 0.44 mg (Con), 12.91 mg (SPI), or 12.57 mg (GLY) of isoflavonoids/kg BW; and 8.94 mg glyceollins/kg BW (GLY) each day. Of note, the initial SPI and GLY diet formulations lacked adequate palatability, requiring all the animals to be placed on the control group diet (with E2) for 1 wk 14 days into the experiment. All diets were reformulated during this time with sweetened applesauce and fed henceforth for 3 weeks without compliance problems. All procedures involving these animals were conducted in compliance with state and federal laws, standards of the U.S. Department of Health and Human Services, and guidelines established by the Wake Forest University Animal Care and Use Committee (ACUC). The facilities and laboratory animal program of Wake Forest University are fully accredited by the Association for the Assessment and Accreditation of Laboratory Animal Care.

Primate Breast Biopsies

At the beginning and end of the dietary treatment period, the animals were anesthetized with ketamine and buprenorphine for breast biopsy, blood collection, uterine ultrasound, vaginal cytology, and body weight measurement. For the breast biopsy, a 1.5-cm incision was made in a preselected breast quadrant, and a small (~0.4 g) sample of mammary gland was removed. The incision was sutured, and the animals were monitored and given analgesia during recovery following ACUC-approved clinical procedures. The biopsy site was tattooed to prevent later resampling at the same site. Half of the biopsy sample was frozen; the other half was fixed at 4° C. in 4% paraformaldehyde for 24 h and then processed for histology using standard procedures.

Example 1

Glyceollins Upregulate ABCG1 via Liver X Receptor in LNCaP Cells In Vitro

As shown in FIG. 1, results from LNCaP cell suggest a role for the glyceollins on LXR. Glyceollin treatment at 5 μM for 48 h led to an 8.1 fold up-regulation of ABCG1. A significant up-regulation for ABCA1 was also observed (data not shown). Genistein treatment led to a 3 fold up-regulation, and daidzein and genistein led to a 2 fold up-regulation.

Example 2

Glyceollin Treatments Lead to Up Regulation of LXR Responsive Genes ABCG1 and ABCA1

The two LXR responsive genes ABCG1 and ABCA1 work in tandem as a cholesterol efflux pump. These molecular effects provide potential mechanisms by which soy glyceollins may provide protection against obesity and obesity related syndrome such as hypercholesterolemia and inflammation. LXRα and LXRβ isotypes have been studied for their critical role in limiting accumulation of free cholesterol in peripheral tissue and macrophages through regulation of reverse cholesterol transporters ATP-binding cassette, subfamily A, member 1 (ABCA1) and subfamily member G1 (ABCG1; 4-5). LXRα is primarily expressed in liver, adipose, and enterocytes where LXRβ is expressed ubiquitously.

Example 3

Glyceollins Alter Gene Expression in MCF7 Cells In Vitro

TABLE 1 shows the results of a SuperArray analysis of genes altered by estradiol, a glyceollin mixture, and tamoxifen treatment in MCF-7 cells. Numbers in bold indicate fold changes in gene expression greater than 1.5. Upon examination of the differential effects of glyceollin and tamoxifen treatment on both SDF-1 and PgR gene expression, we sought to further investigate the differences between the two compounds using a more extensive panel of genes which are commonly altered in breast cancer and estrogen signaling by performing a superarray analyses. Based on the above real time RT-PCR data we chose to treat the MCF-7 cells for four hours with DMSO (vehicle), 1 nM E2, 100 nM tamoxifen or 10 μM glyceollin. Total RNA was extracted, quantitated and a real-time PCR array was performed. The inventors identified several genes up-regulated by Glyceollin: SREBF1, SREBF2, ACOX1, PPARA, FASN, AGPAT7, AGPAT6, SCD5, CPT2, ABCG1, ACO2, ECH1, ECHDC1, ECHDC2, ECHDC3.

TABLE 1

| Estrogen | GLY | TAM | Gene | Description |
|---|---|---|---|---|
| 0.917639882 | 2.139094176 | 1.631274987 | SREBF1 | Homo sapiens sterol regulatory element binding transcription factor 1 (SREBF1), transcript variant 1, mRNA [NM_001005291] |
| 0.982820599 | 1.531557997 | 1.258757174 | SREBF2 | Homo sapiens sterol regulatory element binding transcription factor 2 (SREBF2), mRNA [NM_004599] |
| 1.035264924 | 1.437936533 | 1.300440147 | SREBF2 | Sterol regulatory element-binding protein 2 (SREBP-2) (Sterol regulatory element-binding transcription factor 2). [Source: Uniprot/SWISSPROT; Acc: Q12772] [ENST00000361204] |
| 0.922742493 | 1.53581027 | 1.377450046 | PPARA | Homo sapiens peroxisome proliferator-activated receptor alpha (PPARA), transcript variant 5, mRNA [NM_005036] |
| 0.927230546 | 1.157490217 | 1.204972315 | PPARG | Homo sapiens peroxisome proliferator-activated receptor gamma (PPARG), transcript variant 3, mRNA [NM_138711] |
| 0.893165852 | 1.343503426 | 1.175276328 | ACOX1 | Homo sapiens acyl-Coenzyme A oxidase 1, palmitoyl (ACOX1), transcript variant 1, mRNA [NM_004035] |
| 0.944092419 | 1.28788163 | 1.095811766 | CPT1A | Carnitine O-palmitoyltransferase I, liver isoform (EC 2.3.1.21) (CPTI) (CPTI-L) (Carnitine palmitoyltransferase 1A). |
| 1.006257823 | 1.485552921 | 1.310393404 | CPT1A | Homo sapiens carnitine palmitoyltransferase 1A (liver) (CPT1A), nuclear gene encoding mitochondrial protein, transcript variant 1, mRNA [NM_001876] |
| 1.082224645 | 1.979313313 | 1.52414483 | UCP2 | Homo sapiens uncoupling protein 2 (mitochondrial, proton carrier) (UCP2), nuclear gene encoding mitochondrial protein, mRNA [NM_003355] |
| 1.299539062 | 1.483494934 | 1.346300069 | SERBP1 | Homo sapiens SERPINE1 mRNA binding protein 1 (SERBP1), transcript variant 4, mRNA [NM_015640] |
| 1.4063932 | 2.0265138 | 1.586667686 | FASN | Homo sapiens fatty acid synthase (FASN), mRNA [NM_004104] |
| 1.516767545 | 1.623379162 | 1.404444876 | FASTKD2 | Homo sapiens FAST kinase domains 2 (FASTKD2), mRNA [NM_014929] |
| 2.345669898 | 2.529759085 | 1.312211255 | SGEF | Homo sapiens infant liver cDNA, clone: HMFN1864, full insert sequence. [AB073386] |
| 0.744322628 | 1.241427492 | 1.372684431 | ACSL3 | Homo sapiens acyl-CoA synthetase long-chain family member 3 (ACSL3), transcript variant 1, mRNA [NM_004457] |
| 0.768437591 | 1.608816742 | 1.22010051 | AGPAT7 | Homo sapiens 1-acylglycerol-3-phosphate O-acyltransferase 7 (lysophosphatidic acid acyltransferase, eta) (AGPAT7), mRNA [NM_153613] |
| 1.483494934 | 1.484523571 | 1.178539408 | AGPAT5 | Homo sapiens 1-acylglycerol-3-phosphate O-acyltransferase 5 (lysophosphatidic acid acyltransferase, epsilon) (AGPAT5), mRNA [NM_018361] |
| 1.108032348 | 1.599920257 | 1.370782805 | SCD5 | Homo sapiens stearoyl-CoA desaturase 5 (SCD5), transcript variant 1, mRNA [NM_001037582] |
| 1.00486382 | 1.071773463 | 1.00486382 | SCD5 | Homo sapiens stearoyl-CoA desaturase 5, mRNA (cDNA clone IMAGE: 3607979), complete cds. [BC004936] |

TABLE 1-continued

| Estrogen | GLY | TAM | Gene | Description |
|---|---|---|---|---|
| 1.021720083 | 0.965936329 | 1.054822317 | SCD5 | *Homo sapiens* stearoyl-CoA desaturase 5 (SCD5), transcript variant 2, mRNA [NM_024906] |
| 1.073260286 | 1.282536603 | 1.121943481 | ACACA | *Homo sapiens* acetyl-Coenzyme A carboxylase alpha (ACACA), transcript variant 2, mRNA [NM_198839] |
| 0.967947027 | 1.493813457 | 1.32317144 | CPT1C | *Homo sapiens* carnitine palmitoyltransferase 1C (CPT1C), mRNA [NM_152359] |
| 1.25962998 | 2.084931522 | 2.106722072 | CPT2 | *Homo sapiens* carnitine palmitoyltransferase II (CPT2), nuclear gene encoding mitochondrial protein, mRNA [NM_000098] |
| 0.702222438 | 1.155085785 | 0.916368645 | CPT1B | *Homo sapiens* carnitine palmitoyltransferase 1B (muscle) (CPT1B), nuclear gene encoding mitochondrial protein, transcript variant 3, mRNA [NM_152246] |
| 1.021720083 | 1.301341855 | 1.071030823 | ACSM3 | *Homo sapiens* acyl-CoA synthetase medium-chain family member 3 (ACSM3), transcript variant 2, mRNA [NM_202000] |
| 1.652900636 | 2.243886961 | 1.958840595 | ACSS1 | *Homo sapiens* acyl-CoA synthetase short-chain family member 1 (ACSS1), nuclear gene encoding mitochondrial protein, mRNA [NM_032501] |
| 0.955282936 | 1.303147149 | 1.162314108 | ACSS2 | *Homo sapiens* acyl-CoA synthetase short-chain family member 2 (ACSS2), transcript variant 1, mRNA [NM_018677] |
| 0.961927455 | 1.199478705 | 1.217566019 | IL1RN | *Homo sapiens* interleukin 1 receptor antagonist (IL1RN), transcript variant 1, mRNA [NM_173842] |
| 1.00486382 | 1.071773463 | 1.051172909 | IL1RN | *Homo sapiens* interleukin 1 receptor antagonist, mRNA (cDNA clone IMAGE: 5270437), partial cds. [BC068441] |
| 1.011152081 | 1.038139271 | 1.082975046 | ABCA1 | *Homo sapiens* ATP-binding cassette, sub-family A (ABC1), member 1 (ABCA1), mRNA [NM_005502] |
| 0.965267025 | 1.081474763 | 1.057750964 | ABCA1 | *Homo sapiens* cDNA FLJ14266 fis, clone PLACE1002437, highly similar to ATP-BINDING CASSETTE TRANSPORTER 1. [AK024328] |
| 1.02313747 | 1.042465761 | 1.043188594 | ABCA1 | *Homo sapiens* ATP-binding cassette, sub-family A (ABC1), member 1 (ABCA1), mRNA [NM_005502] |
| 0.987600861 | 1.068065408 | 1.019597683 | ABCA10 | *Homo sapiens* ATP-binding cassette, sub-family A (ABC1), member 10 (ABCA10), mRNA [NM_080282] |
| 1.070288698 | 1.028826708 | 1.0132569 | ABCA13 | *Homo sapiens* ATP-binding cassette, sub-family A (ABC1), member 13 (ABCA13), mRNA [NM_152701] |
| 1.922521857 | 1.655193632 | 1.333298677 | ABCA3 | *Homo sapiens* ATP-binding cassette, sub-family A (ABC1), member 3 (ABCA3), mRNA [NM_001089] |
| 0.76101669 | 0.965936329 | 0.874784765 | ABCA5 | *Homo sapiens* ATP-binding cassette, sub-family A (ABC1), member 5 (ABCA5), transcript variant 1, mRNA [NM_018672] |
| 0.988970916 | 1.082224645 | 1.042465761 | ABCA6 | *Homo sapiens* ATP-binding cassette, sub-family A (ABC1), member 6 (ABCA6), mRNA [NM_080284] |
| 0.880869374 | 1.297738767 | 1.151089491 | ABCA7 | *Homo sapiens* ATP-binding cassette, sub-family A (ABC1), member 7 (ABCA7), transcript variant 1, mRNA [NM_019112] |
| 1.071030823 | 1.033830736 | 1.016774673 | ABCA8 | *Homo sapiens* ATP-binding cassette, sub-family A (ABC1), member 8 (ABCA8), mRNA [NM_007168] |
| 1.016070143 | 1.016774673 | 1.076986376 | ABCA9 | *Homo sapiens* ATP-binding cassette, sub-family A (ABC1), member 9 (ABCA9), mRNA [NM_080283] |
| 1.024556823 | 1.318593614 | 1.137605228 | ABCA11 | *Homo sapiens* ATP-binding cassette, sub-family A (ABC1), member 11 (pseudogene) (ABCA11) on chromosome 4 [NR_002451] |
| 0.76630998 | 1.652900636 | 1.374588696 | ABCA12 | *Homo sapiens* ATP-binding cassette, sub-family A (ABC1), member 12 (ABCA12), transcript variant 1, mRNA [NM_173076] |
| 0.620283649 | 2.051956291 | 1.22010051 | ABCG1 | *Homo sapiens* ATP-binding cassette, sub-family G (WHITE), member 1 (ABCG1), transcript variant 1, mRNA [NM_207630] |
| 0.944747041 | 1.413233644 | 1.616641738 | ACSL1 | *Homo sapiens* acyl-CoA synthetase long-chain family member 1 (ACSL1), mRNA [NM_001995] |
| 0.91319825 | 1.436940177 | 1.295940965 | ACSS2 | *Homo sapiens* acyl-CoA synthetase short-chain family member 2 (ACSS2), transcript variant 1, mRNA [NM_018677] |
| 1.178539408 | 1.469168633 | 1.387030969 | AACS | *Homo sapiens* acetoacetyl-CoA synthetase (AACS), mRNA [NM_023928] |
| 1.719512972 | 1.695839929 | 1.756860936 | ACSS1 | *Homo sapiens* acyl-CoA synthetase short-chain family member 1 (ACSS1), nuclear gene encoding mitochondrial protein, mRNA [NM_032501] |
| 1.408344227 | 1.529436278 | 1.43893358 | IRS2 | *Homo sapiens* insulin receptor substrate 2 (IRS2), mRNA [NM_003749] |
| 0.942784536 | 1.271031689 | 1.266634254 | ACO1 | *Homo sapiens* aconitase 1, soluble (ACO1), mRNA [NM_002197] |

TABLE 1-continued

| Estrogen | GLY | TAM | Gene | Description |
|---|---|---|---|---|
| 1.163120042 | 1.832737289 | 1.618884433 | ACO2 | *Homo sapiens* aconitase 2, mitochondrial (ACO2), nuclear gene encoding mitochondrial protein, mRNA [NM_001098] |
| 1.043188594 | 1.407368375 | 1.223488041 | AGPAT3 | *Homo sapiens* 1-acylglycerol-3-phosphate O-acyltransferase 3 (AGPAT3), transcript variant 1, mRNA [NM_020132] |
| 1.062159186 | 1.4054187 | 1.271913007 | AGPAT3 | *Homo sapiens* 1-acylglycerol-3-phosphate O-acyltransferase 3 (AGPAT3), transcript variant 1, mRNA [NM_020132] |
| 1.230291345 | 2.225300241 | 2.139094176 | ECH1 | *Homo sapiens* enoyl Coenzyme A hydratase 1, peroxisomal (ECH1), mRNA [NM_001398] |
| 1.154285418 | 1.419123356 | 1.495885758 | ECHDC1 | *Homo sapiens* enoyl Coenzyme A hydratase domain containing 1 (ECHDC1), mRNA [NM_018479] |
| 1.209994089 | 2.0265138 | 1.70408819 | ECHDC2 | *Homo sapiens* enoyl Coenzyme A hydratase domain containing 2 (ECHDC2), mRNA [NM_018281] |
| 1.261377409 | 2.009727641 | 1.526259209 | ECHDC3 | *Homo sapiens* enoyl Coenzyme A hydratase domain containing 3 (ECHDC3), mRNA [NM_024693] |
| 1.154285418 | 1.496922987 | 1.500038989 | ECHS1 | *Homo sapiens* enoyl Coenzyme A hydratase, short chain, 1, mitochondrial (ECHS1), nuclear gene encoding mitochondrial protein, mRNA [NM_004092] |
| 1.10343374 | 1.346300069 | 1.337927555 | IDE | *Homo sapiens* insulin-degrading enzyme (IDE), mRNA [NM_004969] |
| 0.981459064 | 1.599920257 | 1.337927555 | IGF2R | *Homo sapiens* insulin-like growth factor 2 receptor (IGF2R), mRNA [NM_000876] |
| 0.938221197 | 1.53261996 | 1.546492675 | LEPROT | *Homo sapiens* leptin receptor overlapping transcript (LEPROT), mRNA [NM_017526] |
| 1.082224645 | 1.979313313 | 1.52414483 | UCP2 | *Homo sapiens* uncoupling protein 2 (mitochondrial, proton carrier) (UCP2), nuclear gene encoding mitochondrial protein, mRNA [NM_003355] |
| 0.784040454 | 1.374588696 | 1.221793102 | IGFBP5 | *Homo sapiens* insulin-like growth factor binding protein 5 (IGFBP5), mRNA [NM_000599] |
| 0.798851916 | 1.160703914 | 1.25092908 | LEPROT | *Homo sapiens* leptin receptor overlapping transcript (LEPROT), mRNA [NM_017526] |
| 1.284315809 | 1.335148303 | 1.092020546 | IGF1R | *Homo sapiens* insulin-like growth factor 1 receptor (IGF1R), mRNA [NM_000875] |
| 1.263127262 | 1.387992719 | 1.082224645 | IGF1R | *Homo sapiens* insulin-like growth factor 1 receptor (IGF1R), mRNA [NM_000875] |
| 1.221793102 | 1.395710764 | 1.100378609 | IGF1R | *Homo sapiens* insulin-like growth factor 1 receptor (IGF1R), mRNA [NM_000875] |
| 1.23370717 | 1.381274448 | 1.0453601 | IGF1R | *Homo sapiens* insulin-like growth factor 1 receptor (IGF1R), mRNA [NM_000875] |
| 1.25092908 | 1.446934886 | 1.011152081 | IGF1R | *Homo sapiens* insulin-like growth factor 1 receptor (IGF1R), mRNA [NM_000875] |
| 3.988925005 | 2.491474831 | 1.22603486 | IGFBP4 | *Homo sapiens* insulin-like growth factor binding protein 4 (IGFBP4), mRNA [NM_001552] |
| 1.0181852 | 1.250062303 | 1.092777739 | AGPAT3 | *Homo sapiens* 1-acylglycerol-3-phosphate O-acyltransferase 3 (AGPAT3), transcript variant 1, mRNA [NM_020132] |
| 1.893427262 | 2.199232299 | 1.695839929 | AGPAT6 | *Homo sapiens* 1-acylglycerol-3-phosphate O-acyltransferase 6 (lysophosphatidic acid acyltransferase, zeta) (AGPAT6), mRNA [NM_178819] |
| 1.842928372 | 2.340797283 | 1.711190051 | AGPAT6 | *Homo sapiens* 1-acylglycerol-3-phosphate O-acyltransferase 6 (lysophosphatidic acid acyltransferase, zeta) (AGPAT6), mRNA [NM_178819] |
| 0.962594443 | 1.262252032 | 1.204137381 | ECH1 | Homo sapiens, clone IMAGE: 3858114, mRNA. [BC014786] |
| 1.399585866 | 2.199232299 | 1.496922987 | ECHDC3 | *Homo sapiens* enoyl Coenzyme A hydratase domain containing 3 (ECHDC3), mRNA [NM_024693] |
| 1.041743429 | 1.35754498 | 1.29145735 | GPATCH1 | *Homo sapiens* G patch domain containing 1 (GPATCH1), mRNA [NM_018025] |
| 1.244874235 | 1.104198847 | 1.065108203 | IGF2 | *Homo sapiens* insulin-like growth factor 2 (somatomedin A) (IGF2), transcript variant 2, mRNA [NM_001007139] |
| 0.944747041 | 1.174461971 | 1.101141598 | ACACB | *Homo sapiens* acetyl-Coenzyme A carboxylase beta (ACACB), mRNA [NM_001093] |
| 0.924022572 | 1.139183377 | 1.165541198 | ACO1 | *Homo sapiens* aconitase 1, soluble (ACO1), mRNA [NM_002197] |
| 0.993092495 | 1.098854218 | 1.042465761 | ACOX1 | *Homo sapiens* acyl-Coenzyme A oxidase 1, palmitoyl (ACOX1), transcript variant 1, mRNA [NM_004035] |

TABLE 1-continued

| Estrogen | GLY | TAM | Gene | Description |
|---|---|---|---|---|
| 1.016070143 | 1.0132569 | 1.022428531 | ACOXL | Homo sapiens acyl-Coenzyme A oxidase-like (ACOXL), mRNA [NM_018308] |
| 1.0181852 | 1.02313747 | 0.999307093 | ACSBG1 | Homo sapiens acyl-CoA synthetase bubblegum family member 1 (ACSBG1), mRNA [NM_015162] |
| 1.01395948 | 1.057750964 | 1.031683179 | ACSBG2 | Homo sapiens acyl-CoA synthetase bubblegum family member 2 (ACSBG2), mRNA [NM_030924] |
| 0.612592666 | 1.092020546 | 1.034547582 | ACSL3 | Homo sapiens acyl-CoA synthetase long-chain family member 3 (ACSL3), transcript variant 1, mRNA [NM_004457] |
| 0.974679631 | 1.083725967 | 1.051901779 | ACSL4 | Homo sapiens acyl-CoA synthetase long-chain family member 4 (ACSL4), transcript variant 1, mRNA [NM_004458] |
| 0.997922719 | 1.056285625 | 1.042465761 | ACSL5 | Homo sapiens acyl-CoA synthetase long-chain family member 5 (ACSL5), transcript variant 3, mRNA [NM_203380] |
| 1.062159186 | 1.021012126 | 1.052631155 | ACSL6 | Homo sapiens mRNA for KIAA0837 protein, partial cds. [AB020644] |
| 1.010451446 | 1.062895674 | 1.044635763 | ACSL6 | Homo sapiens long chain fatty acyl CoA synthetase 2 (LACS2) mRNA, complete cds. [AF099740] |
| 0.993781093 | 1.011152081 | 1.0132569 | ACSL6 | Homo sapiens acyl-CoA synthetase long-chain family member 6 (ACSL6), transcript variant 2, mRNA [NM_001009185] |
| 1.019597683 | 1.136816973 | 1.034547582 | ACSM1 | Homo sapiens acyl-CoA synthetase medium-chain family member 1 (ACSM1), mRNA [NM_052956] |
| 1.040300267 | 1.143930973 | 1.012554807 | ACSM2 | Homo sapiens acyl-CoA synthetase medium-chain family member 2 (ACSM2), nuclear gene encoding mitochondrial protein, mRNA [NM_182617] |
| 0.914465089 | 1.116512962 | 1.088997015 | AGPAT1 | Homo sapiens 1-acylglycerol-3-phosphate O-acyltransferase 1 (lysophosphatidic acid acyltransferase, alpha) (AGPAT1), transcript variant 1, mRNA [NM_006411] |
| 1.141554707 | 2.106722072 | 1.94126894 | AGPAT2 | Homo sapiens 1-acylglycerol-3-phosphate O-acyltransferase 2 (lysophosphatidic acid acyltransferase, beta) (AGPAT2), transcript variant 1, mRNA [NM_006412] |
| 0.96996191 | 1.048989328 | 1.041021598 | AGPAT4 | Homo sapiens 1-acylglycerol-3-phosphate O-acyltransferase 4 (lysophosphatidic acid acyltransferase, delta) (AGPAT4), mRNA [NM_020133] |
| 0.991029563 | 1.009751298 | 1.030968319 | AGPAT4 | Homo sapiens 1-acylglycerol-3-phosphate O-acyltransferase 4 (lysophosphatidic acid acyltransferase, delta) (AGPAT4), mRNA [NM_020133] |
| 1.281647924 | 1.170398641 | 0.984866443 | AGPAT5 | Homo sapiens 1-acylglycerol-3-phosphate O-acyltransferase 5 (lysophosphatidic acid acyltransferase, epsilon) (AGPAT5), mRNA [NM_018361] |
| 1.048989328 | 1.168777249 | 1.130530567 | FAS | Homo sapiens Fas (TNF receptor superfamily, member 6) (FAS), transcript variant 1, mRNA [NM_000043] |
| 1.082224645 | 1.025267238 | 1.039579435 | FASLG | Homo sapiens Fas ligand (TNF superfamily, member 6) (FASLG), mRNA [NM_000639] |
| 0.910038824 | 1.21335356 | 1.147902414 | FASTK | Homo sapiens Fas-activated serine/threonine kinase (FASTK), transcript variant 1, mRNA [NM_006712] |
| 0.906890329 | 1.181811547 | 1.151887642 | FASTK | Homo sapiens Fas-activated serine/threonine kinase (FASTK), transcript variant 1, mRNA [NM_006712] |
| 0.865136691 | 1.23370717 | 1.140763716 | FASTKD1 | Homo sapiens FAST kinase domains 1 (FASTKD1), mRNA [NM_024622] |
| 1.037419937 | 1.048989328 | 1.030253954 | FASTKD1 | Homo sapiens mRNA for KIAA1800 protein, partial cds. [AB058703] |
| 1.071030823 | 0.908778116 | 0.948026965 | FASTKD2 | Homo sapiens FAST kinase domains 2 (FASTKD2), mRNA [NM_014929] |
| 1.078480432 | 1.019597683 | 1.337000495 | FASTKD5 | Homo sapiens FAST kinase domains 5 (FASTKD5), mRNA [NM_021826] |
| 1.169587664 | 1.29056249 | 1.174461971 | HMGCR | Homo sapiens 3-hydroxy-3-methylglutaryl-Coenzyme A reductase (HMGCR), mRNA [NM_000859] |
| 1.163120042 | 1.199139914 | 1.115739322 | HMGCS1 | Homo sapiens 3-hydroxy-3-methylglutaryl-Coenzyme A synthase 1 (soluble) (HMGCS1), mRNA [NM_002130] |
| 0.997922719 | 0.996540263 | 1.074004472 | HMGCS2 | Homo sapiens 3-hydroxy-3-methylglutaryl-Coenzyme A synthase 2 (mitochondrial) (HMGCS2), mRNA [NM_005518] |
| 1.062895674 | 1.330529041 | 1.170398641 | LEPROTL1 | Homo sapiens leptin receptor overlapping transcript-like 1 (LEPROTL1), mRNA [NM_015344] |
| 0.763658749 | 1.207480591 | 1.182631 | LPIN1 | Homo sapiens lipin 1 (LPIN1), mRNA [NM_145693] |

TABLE 1-continued

| Estrogen | GLY | TAM | Gene | Description |
|---|---|---|---|---|
| 0.947370071 | 1.096571589 | 1.067325338 | LPIN2 | *Homo sapiens* lipin 2 (LPIN2), mRNA [NM_014646] |
| 1.00695555 | 1.237132479 | 1.077733145 | LPIN3 | *Homo sapiens* lipin 3 (LPIN3), mRNA [NM_022896] |
| 1.076986376 | 1.131314463 | 1.029540083 | PLIN | *Homo sapiens* perilipin (PLIN), mRNA [NM_002666] |
| 1.015366101 | 0.996540263 | 1.019597683 | SORBS1 | *Homo sapiens* sorbin and SH3 domain containing 1 (SORBS1), transcript variant 2, mRNA [NM_015385] |
| 0.942131274 | 1.056285625 | 0.948684315 | SORBS1 | *Homo sapiens* cDNA FLJ12406 fis, clone MAMMA1002842, weakly similar to Mus musculus c-Cbl associated protein CAP mRNA. [AK022468] |
| 0.986232704 | 1.014662547 | 1.038859103 | UCP1 | *Homo sapiens* uncoupling protein 1 (mitochondrial, proton carrier) (UCP1), nuclear gene encoding mitochondrial protein, mRNA [NM_021833] |
| 0.942131274 | 0.921464186 | 1.00765376 | UCP3 | *Homo sapiens* uncoupling protein 3 (mitochondrial, proton carrier) (UCP3), nuclear gene encoding mitochondrial protein, transcript variant long, mRNA [NM_003356] |
| 1.183451022 | 1.575707772 | 1.225185332 | VEGFA | *Homo sapiens* vascular endothelial growth factor A (VEGFA), transcript variant 1, mRNA [NM_001025366] |
| 0.942784536 | 1.677136369 | 1.447938172 | VEGFB | *Homo sapiens* vascular endothelial growth factor B (VEGFB), mRNA [NM_003377] |
| 1.011152081 | 1.038139271 | 1.082975046 | ABCA1 | *Homo sapiens* ATP-binding cassette, sub-family A (ABC1), member 1 (ABCA1), mRNA [NM_005502] |

Example 4

Glyceollins Alter Gene Expression in Primate Mammary Tissue

TABLE 2 shows the number of significant up-regulated and down-regulated genes in mammary tissue comparing glyceollin-enriched soy protein isolate to normal soy protein isolate. The HADH gene, involved in fatty acid metabolism, was up-regulated with glyceollin treatment. Several genes involved with glycerolipid metabolism were up-regulated including GPD1, GPAM, AGPAT2, and GPAM. The PTGDS gene that is involved with arachidonic acid metabolism was up-regulated. Several genes involved with the ECM-receptor interaction were down regulated including ITGA8, SDC1, syndecan 1, and ITGA2. Up-regulated genes were ITGA7 and CD36. Several genes involved with the PPAR signaling pathway were up-regulated including LPL, PLIN, SORBS1, CD36, and DBI. Several genes involved with the insulin signaling pathway were up-regulated including PRKAR2B, SORBS1, and ACACB.

TABLE 2

| Protein | Gene ID | Grp1 Mean | Grp1 SEM | Grp2 Mean | Grp2 SEM | Ratio | Direction | Gene Identifier |
|---|---|---|---|---|---|---|---|---|
| Fatty acid metabolism | | | | | | | | |
| Hydroxyacyl-Coenzyme A dehydrogenase | HADH | 9.38 | 0.12 | 10.12 | 0.11 | 1.66 | Up | AF001903 |
| Hydroxyacyl-Coenzyme A dehydrogenase | HADH | 8.64 | 0.13 | 9.33 | 0.12 | 1.62 | Up | BC000306 |
| Acetyl-Coenzyme A acetyltransferase 1 (acetoacetyl Coenzyme A thiolase) | ACAT1 | 9.8 | 0.07 | 10.37 | 0.04 | 1.49 | Up | NM_000019 |
| Hydroxyacyl-Coenzyme A dehydrogenase | HADH | 9.55 | 0.08 | 10.12 | 0.13 | 1.49 | Up | NM_005327 |
| Aldehyde dehydrogenase 3 family, member A2 | ALDH3A2 | 8.02 | 0.02 | 8.4 | 0.07 | 1.31 | Up | L47162 |
| Hydroxyacyl-Coenzyme A dehydrogenase/3-ketoacyl-Coenzyme A thiolase/enoyl-Coenzyme A hydratase (trifunctional protein), beta | HADHB | 8.92 | 0.04 | 9.26 | 0.08 | 1.27 | Up | NM_000183 |
| Hydroxyacyl-Coenzyme A dehydrogenase/3-ketoacyl-Coenzyme A thiolase/enoyl-Coenzyme A hydratase (trifunctional protein), alpha | HADHA | 5.46 | 0.09 | 5.79 | 0.09 | 1.26 | Up | BG472176 |
| Glycerolipid metabolism | | | | | | | | |
| Glycerol-3-phosphate dehydrogenase 1 (soluble) | GPD1 | 8.68 | 0.26 | 9.82 | 0.2 | 2.2 | Up | NM_005276 |
| Glycerol-3-phosphate acyltransferase, mitochondrial | GPAM | 8.9 | 0.2 | 10.03 | 0.36 | 2.18 | Up | AV699379 |

TABLE 2-continued

| Protein | Gene ID | Grp1 Mean | Grp1 SEM | Grp2 Mean | Grp2 SEM | Ratio | Direction | Gene Identifier |
|---|---|---|---|---|---|---|---|---|
| 1-acylglycerol-3-phosphate O-acyltransferase 2 (lysophosphatidic acid acyltransferase, beta) | AGPAT2 | 8.14 | 0.16 | 9.18 | 0.26 | 2.05 | Up | U56418 |
| Glycerol-3-phosphate acyltransferase, mitochondrial | GPAM | 9.58 | 0.21 | 10.58 | 0.3 | 2 | Up | AB046780 |
| Glycerol-3-phosphate dehydrogenase 1 (soluble) | GPD1 | 8.53 | 0.22 | 9.43 | 0.28 | 1.87 | Up | AI368018 |
| Choline phosphotransferase 1 | CHPT1 | 8.67 | 0.12 | 9.06 | 0.11 | 1.31 | Up | AF195624 |
| Patatin-like phospholipase domain containing 3 | PNPLA3 | 4.45 | 0.1 | 4.83 | 0.1 | 1.3 | Up | AK025665 |
| Phospholipase A2, group III | PLA2G3 | 4.55 | 0.06 | 4.89 | 0.07 | 1.27 | Up | NM_015715 |
| Arachidonic acid metabolism | | | | | | | | |
| Prostaglandin D2 synthase 21 kDa (brain) | PTGDS | 10.95 | 0.29 | 12.02 | 0.18 | 2.11 | Up | NM_000954 |
| Prostaglandin D2 synthase 21 kDa (brain) | PTGDS | 11.05 | 0.25 | 12.03 | 0.12 | 1.96 | Up | BC005939 |
| Phospholipase A2, group III | PLA2G3 | 4.55 | 0.06 | 4.89 | 0.07 | 1.27 | Up | NM_015715 |
| ECM-receptor interaction | | | | | | | | |
| Integrin, alpha 8 | ITGA8 | 6.54 | 0.33 | 5.38 | 0.19 | 2.24 | Down | AI193623 |
| Syndecan 1 | SDC1 | 8 | 0.19 | 7.16 | 0.13 | 1.8 | Down | NM_002997 |
| Syndecan 1 | SDC1 | 8.69 | 0.17 | 7.94 | 0.18 | 1.68 | Down | NM_002997 |
| Integrin, alpha 7 | ITGA7 | 8.5 | 0.07 | 9.23 | 0.25 | 1.65 | Up | AK022548 |
| syndecan 1 | SDC1 | 7.28 | 0.21 | 6.58 | 0.1 | 1.63 | Down | Z48199 |
| Integrin, alpha 7 | ITGA7 | 7.4 | 0.03 | 8.06 | 0.24 | 1.59 | Up | AF072132 |
| Integrin, alpha 2 (CD49B, alpha 2 subunit of VLA-2 receptor) | ITGA2 | 7.81 | 0.06 | 7.19 | 0.15 | 1.54 | Down | N95414 |
| CD36 molecule (thrombospondin receptor) | CD36 | 11.09 | 0.13 | 11.71 | 0.18 | 1.53 | Up | NM_000072 |
| PPAR signaling pathway | | | | | | | | |
| Lipoprotein lipase | LPL | 11.21 | 0.18 | 12.15 | 0.2 | 1.91 | Up | BF672975 |
| Perilipin | PLIN | 11.03 | 0.07 | 11.8 | 0.24 | 1.7 | Up | NM_002666 |
| Sorbin and SH3 domain containing 1 | SORBS1 | 7.89 | 0.08 | 8.58 | 0.27 | 1.61 | Up | N21458 |
| Sorbin and SH3 domain containing 1 | SORBS1 | 8.97 | 0.06 | 9.63 | 0.13 | 1.58 | Up | NM_015385 |
| CD36 molecule (thrombospondin receptor) | CD36 | 11.09 | 0.13 | 11.71 | 0.18 | 1.53 | Up | NM_000072 |
| Diazepam binding inhibitor (GABA receptor modulator, acyl-Coenzyme A binding protein) | DBI | 11.27 | 0.11 | 11.85 | 0.16 | 1.5 | Up | BC006466 |
| Diazepam binding inhibitor (GABA receptor modulator, acyl-Coenzyme A binding protein) | DBI | 11.34 | 0.06 | 11.9 | 0.16 | 1.48 | Up | M15887 |
| CD36 molecule (thrombospondin receptor) | CD36 | 11.85 | 0.12 | 12.33 | 0.15 | 1.4 | Up | M98399 |
| Oxidized low density lipoprotein (lectin-like) receptor 1 | OLR1 | 4.4 | 0.04 | 4.13 | 0.1 | 1.2 | Down | AF035776 |
| Insulin signaling pathway | | | | | | | | |
| Protein kinase, cAMP-dependent, regulatory, type II, beta | PRKAR2B | 9.07 | 0.16 | 9.9 | 0.28 | 1.77 | Up | NM_002736 |
| Sorbin and SH3 domain containing 1 | SORBS1 | 7.89 | 0.08 | 8.58 | 0.27 | 1.61 | Up | N21458 |
| Acetyl-Coenzyme A carboxylase beta | ACACB | 7.75 | 0.22 | 8.43 | 0.16 | 1.61 | Up | R99037 |
| Sorbin and SH3 domain containing 1 | SORBS1 | 8.97 | 0.06 | 9.63 | 0.13 | 1.58 | Up | NM_015385 |
| Acetyl-Coenzyme A carboxylase beta | ACACB | 7.32 | 0.15 | 7.97 | 0.11 | 1.56 | Up | NM_001093 |
| Acetyl-Coenzyme A carboxylase beta | ACACB | 9.32 | 0.15 | 9.89 | 0.17 | 1.49 | Up | AI057637 |
| Protein kinase, AMP-activated, beta 1 non-catalytic subunit | PRKAB1 | 6.7 | 0.14 | 7.1 | 0.08 | 1.32 | Up | NM_006253 |
| Protein kinase, AMP-activated, beta 2 non-catalytic subunit | PRKAB2 | 4.43 | 0.08 | 4.8 | 0.08 | 1.28 | Up | NM_005399 |
| Sterol regulatory element binding transcription factor 1 | SREBF1 | 9.1 | 0.1 | 9.43 | 0.07 | 1.26 | Up | NM_004176 |
| Protein kinase, cAMP-dependent, regulatory, type II, alpha | PRKAR2A | 6.12 | 0.07 | 6.44 | 0.1 | 1.25 | Up | BC002763 |

TABLE 2-continued

| Protein | Gene ID | Grp1 Mean | Grp1 SEM | Grp2 Mean | Grp2 SEM | Ratio | Direction | Gene Identifier |
|---|---|---|---|---|---|---|---|---|
| Protein kinase C, iota | PRKCI | 7.4 | 0.03 | 7.12 | 0.08 | 1.21 | Down | L18964 |
| Ras homolog enriched in brain | RHEB | 8.23 | 0.06 | 8.5 | 0.02 | 1.21 | Up | AF493921 |

Example 5

Glyceollins Alter Gene Expression in Mouse Liver Tissue

TABLE 3 shows gene expression in liver tissue treated with glyceollins, TABLE 4 shows the number of significant up-regulated (>1.5), and TABLE 5 shows the number of significant down-regulated (<1.5) genes glyceollin treated mouse liver tissue with glyceollins compared to controls.

As can be appreciated from TABLES 3, 4, and 5, treatment with glyceollins caused significant changes in gene expression. A total of 13 genes were up-regulated and 13 genes were down-regulated with glyceollin treatment. In this study the lipid metabolism gene ACOX1 was significantly up-regulated. The up-regulation of this gene may be performed in the liver to prevent excess lipid accumulation. Also, up-regulation of the AHSG and LEP genes alters regulation of body fat and insulin sensitivity.

TABLE 3

| RefSeq Number | Symbol | Description | Group 1 | | | | Group 2 | | | | Group2/ Group 1 |
|---|---|---|---|---|---|---|---|---|---|---|---|
| | | | C1 | C2 | C3 | Avg | TR1 | TR2 | TR3 | Avg | |
| NM_008084 | Gapdh | Glyceraldehyde-3-phosphate dehydrogenase | 26.18 | 16.7 | 49.09 | 30.66 | 85.24 | 47.24 | 96.69 | 76.39 | 2.49 |
| NM_133360 | Acaca | Acetyl-Coenzyme A carboxylase alpha | 1.6 | 0.97 | 1.25 | 1.27 | 0.93 | 1.56 | 1.39 | 1.29 | 1.02 |
| NM_133904 | Acacb | Acetyl-Coenzyme A carboxylase beta | 0.41 | 0.04 | 0.31 | 0.25 | 0.31 | 0.37 | 0.33 | 0.34 | 1.35 |
| NM_015729 | Acox1 | Acyl-Coenzyme A oxidase 1, palmitoyl | 0.66 | 0.44 | 2.37 | 1.16 | 13.73 | 2.16 | 11.03 | 8.97 | 7.75 |
| NM_013459 | Cfd | Complement factor D (adipsin) | 0.41 | 0 | 0.16 | 0.19 | 0.3 | 0.35 | 0.39 | 0.35 | 1.83 |
| NM_013460 | Adra1d | Adrenergic receptor, alpha 1d | 0.54 | 0.13 | 0.36 | 0.34 | 0.33 | 0.5 | 0.5 | 0.44 | 1.28 |
| NM_009636 | Aebp1 | AE binding protein 1 | 10.45 | 8.23 | 5.53 | 8.07 | 3.95 | 9.38 | 6.25 | 6.53 | 0.81 |
| NM_013465 | Ahsg | Alpha-2-HS-glycoprotein | 2.45 | 0.83 | 2.64 | 1.97 | 53.11 | 4.13 | 42.04 | 33.09 | 16.76 |
| NM_009652 | Akt1 | Thymoma viral proto-oncogene 1 | 0.42 | 0.33 | 0.66 | 0.47 | 1.03 | 0.42 | 0.98 | 0.81 | 1.72 |
| NM_007434 | Akt2 | Thymoma viral proto-oncogene 2 | 0.39 | 0.21 | 0.59 | 0.4 | 0.66 | 0.27 | 0.61 | 0.51 | 1.3 |
| NM_011785 | Akt3 | Thymoma viral proto-oncogene 3 | 1.09 | 0.9 | 0.91 | 0.96 | 0.62 | 1.16 | 0.8 | 0.86 | 0.89 |
| NM_009703 | Araf | V-raf murine sarcoma 3611 viral oncogene homolog | 19.26 | 15.7 | 13.41 | 16.12 | 7.92 | 23.37 | 13.14 | 14.81 | 0.92 |
| NM_009743 | Bcl2l1 | Bcl2-like 1 | 0.58 | 0.32 | 0.43 | 0.45 | 0.29 | 0.37 | 0.34 | 0.34 | 0.76 |
| NM_139294 | Braf | Braf transforming gene | 0.26 | 0.25 | 0.3 | 0.27 | 0.3 | 0.18 | 0.28 | 0.25 | 0.94 |
| NM_007598 | Cap1 | CAP, adenylate cyclase-associated protein 1 (yeast) | 0.63 | 0.33 | 0.49 | 0.48 | 0.49 | 0.49 | 0.49 | 0.49 | 1 |
| NM_007619 | Cbl | Casitas B-lineage lymphoma | 12.53 | 10.73 | 8.16 | 10.47 | 6.04 | 13.58 | 8.43 | 9.35 | 0.89 |
| NM_007678 | Cebpa | CCAAT/enhancer binding protein (C/EBP), alpha | 8.55 | 8.19 | 8.13 | 8.29 | 4.53 | 9.4 | 6.46 | 6.8 | 0.82 |
| NM_009883 | Cebpb | CCAAT/enhancer binding protein (C/EBP), beta | 1.23 | 0.91 | 1.15 | 1.1 | 1.91 | 0.83 | 1.6 | 1.44 | 1.31 |
| NM_007679 | Cebpd | CCAAT/enhancer binding protein (C/EBP), delta | 8.07 | 6.7 | 5.38 | 6.72 | 3.57 | 7.72 | 5.32 | 5.53 | 0.82 |
| NM_133656 | Crk | V-crk sarcoma virus CT10 oncogene homolog (avian) | 0.82 | 0.6 | 0.6 | 0.68 | 0.35 | 0.31 | 0.3 | 0.32 | 0.48 |
| NM_009972 | Csn2 | Casein beta | 8.22 | 7.2 | 5.4 | 6.94 | 4.37 | 9.3 | 5.64 | 6.44 | 0.93 |
| NM_010070 | Dok1 | Docking protein 1 | 0.45 | 0.32 | 0.28 | 0.35 | 0.6 | 0.03 | 0.13 | 0.26 | 0.73 |
| NM_010071 | Dok2 | Docking protein 2 | 11.32 | 6.49 | 5.91 | 7.91 | 4.77 | 7.39 | 6.67 | 6.28 | 0.79 |
| NM_013739 | Dok3 | Docking protein 3 | 4.05 | 2.27 | 2.23 | 2.85 | 1.9 | 2.28 | 2.25 | 2.14 | 0.75 |
| NM_053246 | Dok4 | Docking protein 4 | 0.18 | 0.3 | 0.5 | 0.33 | 0.24 | 0.02 | 0.19 | 0.15 | 0.47 |
| NM_029761 | Dok5 | Docking protein 5 | 0.27 | 0.14 | 0.16 | 0.19 | 0.15 | 0.07 | 0.12 | 0.11 | 0.59 |
| NM_019819 | Dusp14 | Dual specificity phosphatase 14 | 0.39 | 0.25 | 0.21 | 0.28 | 0.24 | 0.05 | 0.1 | 0.13 | 0.46 |

TABLE 3-continued

| RefSeq Number | Symbol | Description | Group 1 | | | | Group 2 | | | | Group2/ Group 1 |
|---|---|---|---|---|---|---|---|---|---|---|---|
| | | | C1 | C2 | C3 | Avg | TR1 | TR2 | TR3 | Avg | |
| NM_145371 | Eif2b1 | Eukaryotic translation initiation factor 2B, subunit 1 (alpha) | 1.08 | 0.82 | 0.76 | 0.88 | 0.94 | 0.86 | 0.75 | 0.85 | 0.96 |
| NM_007917 | Eif4e | Eukaryotic translation initiation factor 4E | 90.31 | 86.51 | 59.24 | 78.69 | 41.55 | 91.44 | 64.42 | 65.8 | 0.84 |
| NM_007918 | Eif4ebp1 | Eukaryotic translation initiation factor 4E binding protein 1 | 0.69 | 0.49 | 0.4 | 0.53 | 0.56 | 0.43 | 0.45 | 0.48 | 0.91 |
| NM_007948 | Ercc1 | Excision repair cross-complementing rodent repair deficiency, complementation group 1 | 0.66 | 0.61 | 0.31 | 0.52 | 0.47 | 0.26 | 0.45 | 0.4 | 0.76 |
| NM_007988 | Fasn | Fatty acid synthase | 0.42 | 0.12 | 0.16 | 0.23 | 0.26 | 0 | 0.36 | 0.21 | 0.89 |
| NM_019395 | Fbp1 | Fructose bisphosphatase 1 | 0.38 | 0.42 | 0.57 | 0.46 | 2.7 | 0.27 | 2.03 | 1.67 | 3.66 |
| NM_010234 | Fos | FBJ osteosarcoma oncogene | 0.24 | 0.25 | 0.22 | 0.23 | 0.22 | 0.23 | 0.17 | 0.21 | 0.9 |
| NM_020009 | Frap1 | FK506 binding protein 12-rapamycin associated protein 1 | 0.32 | 0.27 | 0.34 | 0.31 | 0.52 | 0.24 | 0.35 | 0.37 | 1.21 |
| NM_177798 | Frs2 | Fibroblast growth factor receptor substrate 2 | 0.68 | 0.51 | 0.52 | 0.57 | 0.9 | 0.58 | 0.9 | 0.79 | 1.39 |
| NM_144939 | Frs3 | Fibroblast growth factor receptor substrate 3 | 3.24 | 2.9 | 2 | 2.72 | 2.06 | 3.07 | 2.28 | 2.47 | 0.91 |
| NM_008061 | G6pc | Glucose-6-phosphatase, catalytic | 6 | 4.78 | 3.43 | 4.73 | 3.64 | 6.3 | 3.55 | 4.5 | 0.95 |
| NM_021331 | G6pc2 | Glucose-6-phosphatase, catalytic, 2 | 0.39 | 0.27 | 0.15 | 0.27 | 0.28 | 0.01 | 0.08 | 0.12 | 0.46 |
| NM_019468 | G6pd2 | Glucose-6-phosphate dehydrogenase 2 | 0.47 | 0.2 | 0.15 | 0.28 | 0.32 | 0.05 | 0.23 | 0.2 | 0.72 |
| NM_008062 | G6pdx | Glucose-6-phosphate dehydrogenase X-linked | 0.61 | 0.81 | 1.77 | 1.06 | 1.05 | 1.27 | 0.97 | 1.09 | 1.03 |
| NM_021356 | Gab1 | Growth factor receptor bound protein 2-associated protein 1 | 0.58 | 0.96 | 1.26 | 0.93 | 0.78 | 0.8 | 0.66 | 0.75 | 0.8 |
| NM_008100 | Gcg | Glucagon | 2.09 | 2.56 | 2.36 | 2.34 | 1.94 | 2.34 | 1.92 | 2.07 | 0.88 |
| NM_010292 | Gck | Glucokinase | 164.43 | 154.99 | 118.53 | 145.99 | 84.14 | 158.53 | 131.53 | 124.73 | 0.85 |
| NM_010271 | Gpd1 | Glycerol-3-phosphate dehydrogenase 1 (soluble) | 0.73 | 0.5 | 0.36 | 0.53 | 0.77 | 0.7 | 0.43 | 0.63 | 1.19 |
| NM_010274 | Gpd2 | Glycerol phosphate dehydrogenase 2, mitochondrial | 11.64 | 9.39 | 7.32 | 9.45 | 7.91 | 12.84 | 9.57 | 10.11 | 1.07 |
| NM_010345 | Grb10 | Growth factor receptor bound protein 10 | 1.96 | 1.49 | 1.29 | 1.58 | 1.86 | 1.82 | 1.48 | 1.72 | 1.09 |
| NM_008163 | Grb2 | Growth factor receptor bound protein 2 | 3.86 | 2.17 | 4.57 | 3.53 | 2.62 | 2.77 | 2.62 | 2.67 | 0.76 |
| NM_019827 | Gsk3b | Glycogen synthase kinase 3 beta | 7.19 | 7.75 | 7.91 | 7.62 | 5.8 | 9.85 | 8.38 | 8.01 | 1.05 |
| NM_013820 | Hk2 | Hexokinase 2 | 0.23 | 0.34 | 0.26 | 0.28 | 0.55 | 0.24 | 0.22 | 0.34 | 1.21 |
| NM_008284 | Hras1 | Harvey rat sarcoma virus oncogene 1 | 0.5 | 0.82 | 0.75 | 0.69 | 0.92 | 0.62 | 0.85 | 0.8 | 1.15 |
| NM_010513 | Igf1r | Insulin-like growth factor I receptor | 1.17 | 0.95 | 1 | 1.04 | 0.79 | 0.95 | 0.86 | 0.87 | 0.84 |
| NM_010514 | Igf2 | Insulin-like growth factor 2 | 2.1 | 1.92 | 1.75 | 1.92 | 2 | 2.83 | 2.06 | 2.3 | 1.2 |
| NM_008341 | Igfbp1 | Insulin-like growth factor binding protein 1 | 8.49 | 7.6 | 6.52 | 7.54 | 6.67 | 11.26 | 8.89 | 8.94 | 1.19 |
| NM_008386 | Ins1 | Insulin I | 1.78 | 1.54 | 1.47 | 1.6 | 1.56 | 1.94 | 1.52 | 1.67 | 1.05 |
| NM_013564 | Insl3 | Insulin-like 3 | 0.58 | 0.53 | 0.37 | 0.49 | 0.99 | 0.57 | 0.86 | 0.81 | 1.64 |
| NM_010568 | Insr | Insulin receptor | 0.1 | 0.22 | 0.14 | 0.15 | 0.57 | 0.3 | 0.57 | 0.48 | 3.13 |
| NM_010570 | Irs1 | Insulin receptor substrate 1 | 0.54 | 1.05 | 0.87 | 0.82 | 1.02 | 1.31 | 0.96 | 1.1 | 1.33 |
| XM_357863 | Irs2 | Insulin receptor substrate 2 | 0 | 0.09 | 0.26 | 0.12 | 0.33 | 0.11 | 0.53 | 0.33 | 2.77 |

TABLE 3-continued

| RefSeq Number | Symbol | Description | Group 1 | | | | Group 2 | | | | Group2/ Group 1 |
|---|---|---|---|---|---|---|---|---|---|---|---|
| | | | C1 | C2 | C3 | Avg | TR1 | TR2 | TR3 | Avg | |
| NM_010572 | Irs4 | Insulin receptor substrate 4 | 0.1 | 0.31 | 0.09 | 0.17 | 0.24 | 0.05 | 0.25 | 0.18 | 1.08 |
| NM_010591 | Jun | Jun oncogene | 0.13 | 0.18 | 0.18 | 0.16 | 0.47 | 0.23 | 0.41 | 0.37 | 2.24 |
| NM_021284 | Kras | V-Ki-ras2 Kirsten rat sarcoma viral oncogene homolog | 0.28 | 0.31 | 0.24 | 0.28 | 0.72 | 0.31 | 0.91 | 0.65 | 2.35 |
| NM_010700 | Ldlr | Low density lipoprotein receptor | 7.86 | 6.85 | 6.38 | 7.03 | 5.91 | 10.64 | 7.16 | 7.9 | 1.12 |
| NM_008493 | Lep | Leptin | 0.24 | 0.22 | 0 | 0.15 | 0.5 | 0.33 | 0.86 | 0.57 | 3.71 |
| NM_008927 | Map2k1 | Mitogen activated protein kinase kinase 1 | 0.34 | 0.34 | 0.38 | 0.35 | 0.32 | 0.19 | 0.37 | 0.29 | 0.82 |
| NM_023138 | Map2k2 | Mitogen activated protein kinase kinase 2 | 0.4 | 0.45 | 0.45 | 0.43 | 0.42 | 0.4 | 0.38 | 0.4 | 0.93 |
| NM_011949 | Mapk1 | Mitogen activated protein kinase 1 | 0.34 | 0.32 | 0.37 | 0.34 | 0.32 | 0.32 | 0.32 | 0.32 | 0.94 |
| NM_021461 | Mknk1 | MAP kinase-interacting serine/threonine kinase 1 | 1.66 | 1.62 | 1.77 | 1.69 | 1.46 | 2.25 | 1.97 | 1.89 | 1.12 |
| NM_010878 | Nck1 | Non-catalytic region of tyrosine kinase adaptor protein 1 | 0.2 | 0.58 | 0.28 | 0.35 | 0.59 | 0.09 | 0.29 | 0.32 | 0.91 |
| NM_010879 | Nck2 | Non-catalytic region of tyrosine kinase adaptor protein 2 | 2.56 | 2.5 | 3.83 | 2.96 | 2.5 | 4.47 | 2.79 | 3.25 | 1.1 |
| NM_010927 | Nos2 | Nitric oxide synthase 2, inducible, macrophage | 17.52 | 16.47 | 13.84 | 15.94 | 9.88 | 23.63 | 14.88 | 16.13 | 1.01 |
| NM_023456 | Npy | Neuropeptide Y | 17.78 | 13.21 | 12.68 | 14.56 | 7.92 | 22 | 10.06 | 13.33 | 0.92 |
| NM_008768 | Orm1 | Orosomucoid 1 | 0.28 | 0.3 | 0.45 | 0.34 | 0.05 | 0.16 | 0.27 | 0.16 | 0.47 |
| NM_028994 | Pck2 | Phosphoenolpyruvate carboxykinase 2 (mitochondrial) | 0.45 | 0.44 | 0.86 | 0.58 | 0.17 | 0.31 | 0.36 | 0.28 | 0.48 |
| NM_011062 | Pdpk1 | 3-phosphoinositide dependent protein kinase-1 | 0.18 | 0.12 | 0.45 | 0.25 | 0.13 | 0.03 | 0.12 | 0.09 | 0.38 |
| XM_358384 | Phip | Pleckstrin homology domain interacting protein | 1.32 | 1.1 | 1.32 | 1.25 | 1.27 | 1.71 | 1.47 | 1.48 | 1.19 |
| NM_008839 | Pik3ca | Phosphatidylinositol 3-kinase, catalytic, alpha polypeptide | 3.75 | 4.3 | 3.69 | 3.91 | 1.94 | 4.21 | 3.6 | 3.25 | 0.83 |
| NM_029094 | Pik3cb | Phosphatidylinositol 3-kinase, catalytic, beta polypeptide | 0.32 | 0.65 | 0.45 | 0.47 | 0.77 | 0.28 | 0.27 | 0.44 | 0.94 |
| NM_001024955 | Pik3r1 | Phosphatidylinositol 3-kinase, regulatory subunit, polypeptide 1 (p85 alpha) | 1.15 | 1.94 | 0.87 | 1.32 | 1.39 | 1.25 | 0.94 | 1.19 | 0.9 |
| NM_008841 | Pik3r2 | Phosphatidylinositol 3-kinase, regulatory subunit, polypeptide 2 (p85 beta) | 2.26 | 2.78 | 2.21 | 2.41 | 2.28 | 2.52 | 1.49 | 2.1 | 0.87 |
| NM_181585 | Pik3r3 | Phosphatidylinositol 3 kinase, regulatory subunit, polypeptide 3 (p55) | 0.38 | 0.11 | 0.34 | 0.28 | 0 | 0.23 | 0 | 0.08 | 0.27 |
| NM_013631 | Pklr | Pyruvate kinase liver and red blood cell | 0.48 | 0.2 | 0.49 | 0.39 | 0.11 | 9.53 | 0.13 | 3.26 | 8.35 |
| NM_011099 | Pkm2 | Pyruvate kinase, muscle | 1 | 0.77 | 1.09 | 0.95 | 0.43 | 1.08 | 0.66 | 0.72 | 0.76 |
| NM_011146 | Pparg | Peroxisome proliferator activated receptor gamma | 2.59 | 2.25 | 2.13 | 2.33 | 1.01 | 2.53 | 2 | 1.85 | 0.79 |
| NM_031868 | Ppp1ca | Protein phosphatase 1, catalytic subunit, alpha isoform | 14.68 | 11.81 | 10.24 | 12.25 | 5.89 | 16.04 | 10.86 | 10.93 | 0.89 |
| NM_008855 | Prkcb1 | Protein kinase C, beta 1 | 0.45 | 0.6 | 0.46 | 0.5 | 0.74 | 0.16 | 0.11 | 0.34 | 0.68 |
| NM_011102 | Prkcc | Protein kinase C, gamma | 0.61 | 0.87 | 0.6 | 0.69 | 0.82 | 0.21 | 0.48 | 0.51 | 0.73 |
| NM_008857 | Prkci | Protein kinase C, iota | 0.52 | 1.09 | 0.48 | 0.7 | 0.68 | 0.22 | 0.16 | 0.35 | 0.51 |
| NM_008860 | Prkcz | Protein kinase C, zeta | 0.62 | 0.44 | 0.83 | 0.63 | 0.15 | 0.38 | 0.56 | 0.36 | 0.58 |
| NM_011164 | Prl | Prolactin | 0.22 | 0.06 | 0.41 | 0.23 | 0.04 | 0.13 | 0.07 | 0.08 | 0.35 |

TABLE 3-continued

| RefSeq Number | Symbol | Description | Group 1 | | | | Group 2 | | | | Group2/ Group 1 |
|---|---|---|---|---|---|---|---|---|---|---|---|
| | | | C1 | C2 | C3 | Avg | TR1 | TR2 | TR3 | Avg | |
| NM_011201 | Ptpn1 | Protein tyrosine phosphatase, non-receptor type 1 | 0.32 | 0.01 | 1.21 | 0.51 | 0.16 | 0.68 | 0.28 | 0.37 | 0.73 |
| NM_011202 | Ptpn11 | Protein tyrosine phosphatase, non-receptor type 11 | 0.22 | 0.03 | 0.16 | 0.14 | 0.11 | 0.01 | 0.08 | 0.07 | 0.48 |
| NM_011213 | Ptprf | Protein tyrosine phosphatase, receptor type, F | 2.78 | 2.22 | 1.83 | 2.28 | 1.44 | 2.14 | 2.05 | 1.88 | 0.82 |
| NM_029780 | Raf1 | V-raf-leukemia viral oncogene 1 | 0.41 | 0.23 | 0.77 | 0.47 | 0.56 | 2.31 | 0.31 | 1.06 | 2.24 |
| NM_022984 | Retn | Resistin | 1.88 | 3.13 | 2.11 | 2.38 | 2.09 | 2.01 | 1.96 | 2.02 | 0.85 |
| NM_009097 | Rps6ka1 | Ribosomal protein S6 kinase polypeptide 1 | 1.01 | 2.2 | 0.9 | 1.37 | 0.78 | 0.87 | 0.44 | 0.69 | 0.51 |
| NM_028259 | Rps6kb1 | Ribosomal protein S6 kinase, polypeptide 1 | 19.72 | 21.12 | 16.6 | 19.15 | 7.79 | 23.44 | 16.35 | 15.86 | 0.83 |
| NM_009101 | Rras | Harvey rat sarcoma oncogene, subgroup R | 3.18 | 3.31 | 2.79 | 3.09 | 1.85 | 4.43 | 3.94 | 3.41 | 1.1 |
| NM_025846 | Rras2 | Related RAS viral (r-ras) oncogene homolog 2 | 0.34 | 0.1 | 0.34 | 0.26 | 0.2 | 0.15 | 0.17 | 0.18 | 0.68 |
| NM_008871 | Serpine1 | Serine (or cysteine) peptidase inhibitor, clade E, member 1 | 0.21 | 0.06 | 0.2 | 0.16 | 0.25 | 0.11 | 0.53 | 0.3 | 1.89 |
| NM_011368 | Shc1 | Src homology 2 domain-containing transforming protein C1 | 0.48 | 0.34 | 0.43 | 0.41 | 0.53 | 0.23 | 0.5 | 0.42 | 1.01 |
| NM_009167 | Shc3 | Src homology 2 domain-containing transforming protein C3 | 21.89 | 18.99 | 15.6 | 18.82 | 13.52 | 24.38 | 17.27 | 18.39 | 0.98 |
| NM_011989 | Slc27a4 | Solute carrier family 27 (fatty acid transporter), member 4 | 159.81 | 141.42 | 124.02 | 141.75 | 81.12 | 166.99 | 98.4 | 115.5 | 0.81 |
| NM_011400 | Slc2a1 | Solute carrier family 2 (facilitated glucose transporter), member 1 | 0.65 | 1.53 | 0.44 | 0.87 | 0.62 | 0.45 | 0.32 | 0.46 | 0.53 |
| NM_009204 | Slc2a4 | Solute carrier family 2 (facilitated glucose transporter), member 4 | 0.46 | 0.28 | 0.47 | 0.4 | 0.2 | 0.22 | 0.17 | 0.2 | 0.49 |
| NM_009166 | Sorbs1 | Sorbin and SH3 domain containing 1 | 0.69 | 0.66 | 1.08 | 0.81 | 1.34 | 0.93 | 1.19 | 1.15 | 1.42 |
| NM_009231 | Sos1 | Son of sevenless homolog 1 (*Drosophila*) | 0.58 | 0.67 | 0.48 | 0.57 | 0.45 | 0.29 | 1.43 | 0.72 | 1.26 |
| XM_127051 | Sos2 | Son of sevenless homolog 2 (*Drosophila*) | 0.63 | 0.38 | 0.43 | 0.48 | 0.55 | 0.18 | 0.35 | 0.36 | 0.75 |
| NM_011480 | Srebf1 | Sterol regulatory element binding factor 1 | 1.48 | 1.05 | 0.94 | 1.16 | 1.32 | 0.87 | 0.91 | 1.03 | 0.89 |
| NM_009375 | Tg | Thyroglobulin | 3.47 | 0.77 | 0.66 | 1.64 | 0.4 | 0.37 | 0.26 | 0.34 | 0.21 |
| NM_013692 | Klf10 | Kruppel-like factor 10 | 1.09 | 1.94 | 0.76 | 1.26 | 0.81 | 0.84 | 0.7 | 0.78 | 0.62 |
| NM_009463 | Ucp1 | Uncoupling protein 1 (mitochondrial, proton carrier) | 0.72 | 1.22 | 0.74 | 0.89 | 0.55 | 0.29 | 0.33 | 0.39 | 0.43 |
| NM_011671 | Ucp2 | Uncoupling protein 2 (mitochondrial, proton carrier) | 0.37 | 0.66 | 0.91 | 0.65 | 0.32 | 0.51 | 0.31 | 0.38 | 0.58 |
| NM_009505 | Vegfa | Vascular endothelial growth factor A | 0.42 | 0.42 | 0.57 | 0.47 | 1.42 | 1.04 | 0.72 | 1.06 | 2.27 |
| L08752 | PUC18 | PUC18 Plasmid DNA | 0.47 | 0.88 | 0.68 | 0.68 | 0.23 | 0.48 | 0.31 | 0.34 | 0.5 |
| | Blank | | 0.51 | 0.93 | 0.57 | 0.67 | 0.19 | 0.07 | 0.3 | 0.18 | 0.28 |
| | Blank | | 0.6 | 1.19 | 0.68 | 0.82 | 0.54 | 0.11 | 0.46 | 0.37 | 0.45 |
| SA_00005 | AS1R2 | Artificial Sequence 1 Related 2 (80% identity) (48/60) | 0.66 | 0.63 | 0.72 | 0.67 | 0.31 | 0.18 | 0.65 | 0.38 | 0.57 |
| SA_00004 | AS1R1 | Artificial Sequence 1 Related 1 (90% identity) (54/60) | 1.17 | 1.26 | 1.59 | 1.34 | 1.16 | 0.86 | 1.03 | 1.02 | 0.76 |
| SA_00003 | AS1 | Artificial Sequence 1 | 1.98 | 2.75 | 3.71 | 2.81 | 2.72 | 2.18 | 2.72 | 2.54 | 0.9 |
| NM_024277 | Rps27a | Ribosomal protein S27a | 0.22 | 0.24 | 0.78 | 0.41 | 0.53 | 0.2 | 0.69 | 0.48 | 1.15 |

TABLE 3-continued

| RefSeq Number | Symbol | Description | Group 1 | | | | Group 2 | | | | Group2/ |
|---|---|---|---|---|---|---|---|---|---|---|---|
| | | | C1 | C2 | C3 | Avg | TR1 | TR2 | TR3 | Avg | Group 1 |
| NM_009735 | B2m | Beta-2 microglobulin | 5.89 | 3.93 | 8.09 | 5.97 | 13.14 | 6.74 | 13.82 | 11.23 | 1.88 |
| NM_008302 | Hsp90ab1 | Heat shock protein 90 kDa alpha (cytosolic), class B member 1 | 1.07 | 1.14 | 1.09 | 1.1 | 1.32 | 0.66 | 1.99 | 1.32 | 1.2 |
| NM_008302 | Hsp90ab1 | Heat shock protein 90 kDa alpha (cytosolic), class B member 1 | 1.03 | 1.59 | 1.11 | 1.24 | 1.53 | 0.61 | 2.03 | 1.39 | 1.12 |
| NM_008907 | Ppia | Peptidylprolyl isomerase A | 3.73 | 12.07 | 3.92 | 6.58 | 5.94 | 3.31 | 4.46 | 4.57 | 0.7 |
| NM_008907 | Ppia | Peptidylprolyl isomerase A | 3.72 | 3.8 | 4.46 | 3.99 | 6 | 3.23 | 4.14 | 4.46 | 1.12 |
| SA_00007 | BAS2C | Biotinylated Artificial Sequence 2 Complementary sequence | 173.8 | 175.42 | 160.43 | 169.88 | 83.93 | 136.64 | 126.59 | 115.72 | 0.68 |
| SA_00007 | BAS2C | Biotinylated Artificial Sequence 2 Complementary sequence | 276.7 | 275.3 | 234.08 | 262.03 | 161.09 | 219.17 | 211.46 | 197.24 | 0.75 |

TABLE 4

| RefSeq Number | Symbol | Description | Group 1 | | | | Group 2 | | | | Group 2/ |
|---|---|---|---|---|---|---|---|---|---|---|---|
| | | | C1 | C2 | C3 | Avg | TR1 | TR2 | TR3 | Avg | Group 1 |
| NM_008084 | Gapdh | Glyceraldehyde-3-phosphate dehydrogenase | 26.18 | 16.7 | 49.09 | 30.66 | 85.24 | 47.24 | 96.69 | 76.39 | 2.49 |
| NM_015729 | Acox1 | Acyl-Coenzyme A oxidase 1, palmitoyl | 0.66 | 0.44 | 2.37 | 1.16 | 13.73 | 2.16 | 11.03 | 8.97 | 7.75 |
| NM_013465 | Ahsg | Alpha-2-HS-glycoprotein | 2.45 | 0.83 | 2.64 | 1.97 | 53.11 | 4.13 | 42.04 | 33.09 | 16.76 |
| NM_019395 | Fbp1 | Fructose bisphosphatase 1 | 0.38 | 0.42 | 0.57 | 0.46 | 2.7 | 0.27 | 2.03 | 1.67 | 3.66 |
| NM_010568 | Insr | Insulin receptor | 0.1 | 0.22 | 0.14 | 0.15 | 0.57 | 0.3 | 0.57 | 0.48 | 3.13 |
| XM_357863 | Irs2 | Insulin receptor substrate 2 | 0 | 0.09 | 0.26 | 0.12 | 0.33 | 0.11 | 0.53 | 0.33 | 2.77 |
| NM_010591 | Jun | Jun oncogene | 0.13 | 0.18 | 0.18 | 0.16 | 0.47 | 0.23 | 0.41 | 0.37 | 2.24 |
| NM_008493 | Lep | Leptin | 0.24 | 0.22 | 0 | 0.15 | 0.5 | 0.33 | 0.86 | 0.57 | 3.71 |
| NM_021284 | Kras | V-Ki-ras2 Kirsten rat sarcoma viral oncogene homolog | 0.28 | 0.31 | 0.24 | 0.28 | 0.72 | 0.31 | 0.91 | 0.65 | 2.35 |
| NM_013631 | Pklr | Pyruvate kinase liver and red blood cell | 0.48 | 0.2 | 0.49 | 0.39 | 0.11 | 9.53 | 0.13 | 3.26 | 8.35 |
| NM_029780 | Raf1 | V-raf-leukemia viral oncogene 1 | 0.41 | 0.23 | 0.77 | 0.47 | 0.56 | 2.31 | 0.31 | 1.06 | 2.24 |
| NM_008871 | Serpine1 | Serine (or cysteine) peptidase inhibitor, clade E, member 1 | 0.21 | 0.06 | 0.2 | 0.16 | 0.25 | 0.11 | 0.53 | 0.3 | 1.89 |
| NM_009505 | Vegfa | Vascular endothelial growth factor A | 0.42 | 0.42 | 0.57 | 0.47 | 1.42 | 1.04 | 0.72 | 1.06 | 2.27 |
| NM_009735 | B2m | Beta-2 microgbulin | 5.89 | 3.93 | 8.09 | 5.97 | 13.14 | 6.74 | 13.82 | 11.23 | 1.88 |

TABLE 5

| RefSeq Number | Symbol | Description | Group 1 | | | | Group 2 | | | | Group 2/ |
|---|---|---|---|---|---|---|---|---|---|---|---|
| | | | C1 | C2 | C3 | Avg | TR1 | TR2 | TR3 | Avg | Group 1 |
| NM_011164 | Prl | Prolactin | 0.22 | 0.06 | 0.41 | 0.23 | 0.04 | 0.13 | 0.07 | 0.08 | 0.35 |
| NM_133656 | Crk | V-crk sarcoma virus CT10 oncogene homolog (avian) | 0.82 | 0.6 | 0.6 | 0.68 | 0.35 | 0.31 | 0.3 | 0.32 | 0.48 |

TABLE 5-continued

| RefSeq Number | Symbol | Description | Group 1 C1 | C2 | C3 | Avg | Group 2 TR1 | TR2 | TR3 | Avg | Group 2/ Group 1 |
|---|---|---|---|---|---|---|---|---|---|---|---|
| NM_053246 | Dok4 | Docking protein 4 | 0.18 | 0.3 | 0.5 | 0.33 | 0.24 | 0.02 | 0.19 | 0.15 | 0.47 |
| NM_019819 | Dusp14 | Dual specificity phosphatase 14 | 0.39 | 0.25 | 0.21 | 0.28 | 0.24 | 0.05 | 0.1 | 0.13 | 0.46 |
| NM_008768 | Orm1 | Orosomucoid 1 | 0.28 | 0.3 | 0.45 | 0.34 | 0.05 | 0.16 | 0.27 | 0.16 | 0.47 |
| NM_028994 | Pck2 | Phosphoenolpyruvate carboxykinase 2 (mitochondrial) | 0.45 | 0.44 | 0.86 | 0.58 | 0.17 | 0.31 | 0.36 | 0.28 | 0.48 |
| NM_011062 | Pdpk1 | 3-phosphoinositide dependent protein kinase-1 | 0.18 | 0.12 | 0.45 | 0.25 | 0.13 | 0.03 | 0.12 | 0.09 | 0.38 |
| NM_011202 | Ptpn11 | Protein tyrosine phosphatase, non-receptor type 11 | 0.22 | 0.03 | 0.16 | 0.14 | 0.11 | 0.01 | 0.08 | 0.07 | 0.48 |
| NM_181585 | Pik3r3 | Phosphatidylinositol 3 kinase, regulatory subunit, polypeptide 3 (p55) | 0.38 | 0.11 | 0.34 | 0.28 | 0 | 0.23 | 0 | 0.08 | 0.27 |
| NM_009375 | Tg | Thyroglobulin | 3.47 | 0.77 | 0.66 | 1.64 | 0.4 | 0.37 | 0.26 | 0.34 | 0.21 |
| NM_013692 | Klf10 | Kruppel-like factor 10 | 1.09 | 1.94 | 0.76 | 1.26 | 0.81 | 0.84 | 0.7 | 0.78 | 0.62 |
| NM_009463 | Ucp1 | Uncoupling protein 1 (mitochondrial, proton carrier) | 0.72 | 1.22 | 0.74 | 0.89 | 0.55 | 0.29 | 0.33 | 0.39 | 0.43 |
| L08752 | PUC18 | PUC18 Plasmid DNA | 0.47 | 0.88 | 0.68 | 0.68 | 0.23 | 0.48 | 0.31 | 0.34 | 0.5 |

TABLE 6 displays the number of significant up-regulated (>1.5) and TABLE 7 displays the number of significant down-regulated (<1.5) genes in mouse liver tissue treated with glyceollins (E2 added) compared to controls (E2 added). A total of 19 genes were significantly up-regulated by glyceollin treatment, and a total of 31 genes were significantly down-regulated. Again, in this study the lipid metabolism gene ACOX1 was significantly up-regulated and up regulation of the AHSG gene was detected. Several other up-regulated genes involved in lipid and cholesterol function were caused by glyceollin treatment. The SORBS1 gene is important in lipid transport and SREBF1 is involved in cholesterol transport. TABLE 7 also displays several significant down-regulated genes. INS1 is important in insulin regulation.

TABLE 6

Genes Over-Expressed in Group 2 vs. Group 1

| Symbol | Description | Group 2/ Group 1 |
|---|---|---|
| Acox1 | Acyl-Coenzyme A oxidase 1, palmitoyl | 2.89 |
| Ahsg | Glyceraldehyde-3-phosphate dehydrogenase | 3.49 |
| Akt1 | Thymoma viral proto-oncogene 1 | 1.95 |
| Akt2 | Thymoma viral proto-oncogene 2 | 3.9 |
| Cap1 | CAP, adenylate cyclase-associated protein 1 (yeast) | 4.49 |
| Cebpb | CCAAT/enhancer binding protein (C/EBP), beta | 6.49 |
| Crk | V-crk sarcoma virus CT10 oncogene homolog (avian) | 2.8 |
| Eif2b1 | Eukaryotic translation initiation factor 2B, subunit 1 (alpha) | 2.11 |
| Eif4ebp1 | Eukaryotic translation initiation factor 4E binding protein 1 | 1.99 |
| Fbp1 | Fructose bisphosphatase 1 | 20.83 |
| Fos | FBJ osteosarcoma oncogene | 3.82 |
| Hras1 | Harvey rat sarcoma virus oncogene 1 | 1.75 |
| Map2k1 | Mitogen activated protein kinase kinase 1 | 6.09 |
| Orm1 | Mitogen activated protein kinase kinase 1 | 9.74 |
| Ptpn1 | Protein tyrosine phosphatase, non-receptor type 1 | 7.73 |
| Ptpn11 | Protein tyrosine phosphatase, non-receptor type 11 | 30.51 |

TABLE 6-continued

Genes Over-Expressed in Group 2 vs. Group 1

| Symbol | Description | Group 2/ Group 1 |
|---|---|---|
| Sorbs1 | Sorbin and SH3 domain containing 1 | 2.36 |
| Srebf1 | Sterol regulatory element binding factor 1 | 2.04 |
| Vegfa | Vascular endothelial growth factor A | 7.65 |

TABLE 7

Genes Under-Expressed in Group 2 vs. Group 1

| Symbol | Description | Group 2/ Group 1 |
|---|---|---|
| Aebp1 | AE binding protein 1 | 0.43 |
| Araf | V-raf murine sarcoma 3611 viral oncogene homolog | 0.47 |
| Cbl | Casitas B-lineage lymphoma | 0.4 |
| Cebpa | CCAAT/enhancer binding protein (C/EBP), alpha | 0.45 |
| Cebpd | CCAAT/enhancer binding protein (C/EBP), delta | 0.49 |
| Csn2 | Casein beta | 0.39 |
| Dok2 | Docking protein 2 | 0.34 |
| Dok3 | Docking protein 3 | 0.3 |
| Eif4e | Eukaryotic translation initiation factor 4E | 0.45 |
| Frs3 | Fibroblast growth factor receptor substrate 3 | 0.53 |
| G6pc | Glucose-6-phosphatase, catalytic | 0.66 |
| Gcg | Glucagon | 0.48 |
| Gck | Glucokinase | 0.43 |
| Gpd2 | Glycerol phosphate dehydrogenase 2, mitochondrial | 0.52 |
| Grb10 | Growth factor receptor bound protein 10 | 0.35 |
| Grb2 | Growth factor receptor bound protein 2 | 0.36 |
| Gsk3b | Glycogen synthase kinase 3 beta | 0.49 |
| Igf2 | Insulin-like growth factor 2 | 0.65 |
| Ins1 | Insulin I | 0.39 |
| Ldlr | Low density lipoprotein receptor | 0.38 |
| Nck2 | Non-catalytic region of tyrosine kinase adaptor protein 2 | 0.37 |
| Nos2 | Nitric oxide synthase 2, inducible, macrophage | 0.4 |
| Npy | Neuropeptide Y | 0.43 |
| Phip | Pleckstrin homology domain interacting protein | 0.54 |

TABLE 7-continued

Genes Under-Expressed in Group 2 vs. Group 1

| Symbol | Description | Group 2/Group 1 |
| --- | --- | --- |
| Pik3ca | Phosphatidylinositol 3-kinase, catalytic, alpha polypeptide | 0.4 |
| Pik3r2 | Phosphatidylinositol 3-kinase, regulatory subunit, polypeptide 2 (p85 beta) | 0.51 |
| Ppp1ca | Protein phosphatase 1, catalytic subunit, alpha isoform | 0.51 |
| Ptprf | Protein tyrosine phosphatase, receptor type, F | 0.52 |
| Retn | Resistin | 0.41 |
| Shc3 | Src homology 2 domain-containing transforming protein C3 | 0.39 |
| Slc27a4 | Solute carrier family 27 (fatty acid transporter), member 4 | 0.42 |

Cholesterol is an integral component of lipid membranes in eukaryotic cells that is required for maintaining membrane fluidity and facilitating the trafficking and signaling of membrane-associated proteins. Cholesterol is also a necessary precursor for important metabolites, such as steroid hormones, bile salts and oxysterols. Several pathways coordinate cholesterol homeostasis in the body. Briefly, in the first pathway, cells acquire cholesterol, primarily through the binding of circulating cholesterol-rich low-density lipoprotein (LDL) particles to cellular lipoprotein receptors. The receptor-ligand complex is subsequently absorbed into the cell through clathrin-mediated endocytosis, and cholesterol is then used by a variety of downstream biochemical pathways. In the second pathway, cholesterol is synthesized when intra-cellular levels are low, through activation of the SCAP/SREBP signaling cascade. SREBP (sterol regulatory element binding protein) is a transcription factor that regulates expression of numerous cholesterol synthesizing genes, and SCAP (SREBP cleavage activating protein) regulates its activity. Finally, a reverse cholesterol transport pathway is activated when the cell accumulates excess cholesterol, which must then be transported to the liver for excretion into the bile. In this third pathway, circulating high-density lipoprotein (HDL) acts as the primary acceptor of cholesterol from non-liver cells.

Genistein has been shown to produce a hypolipidemic effect through the up-regulation of genes involved in fatty acid catabolism in the liver. Of particular interest were the observed changes in the expression of genes involved in fatty acid catabolism, including ACOX1.

Materials and Methods: Diabetes
Primate Study and Diets

Subjects for this study were 30 adult female surgically menopausal cynomolgus macaques (*Macaca fascicularis*) with an average age of 17.8±0.5 years. All animals had been ovariectomized for 4 years and housed since this time in stable social groups of 3-4 animals each. Animals were randomized by social group to receive one of three diets containing the following: (1) casein/lactalbumin (C/L, n=9); (2) soy protein isolate containing 193.6 mg/1800 kcal isoflavones (SOY, n=11); and (3) glyceollin-enriched soy protein containing 188.5 mg/1800 kcal isoflavones and 134.1 mg/1800 kcal glyceollins (GLY, n=10). All isoflavone doses are expressed in aglycone equivalents. Each diet also included a physiologic dose of micronized 17β-estradiol (E2, 1 mg/1800 kcal), as described previously (Wood et al 2006). Additional details regarding diet production, composition, and analysis are also provided in this prior report (Wood et al 2006).

Briefly, the GLY supplement contained 959.5 μg of unconjugated glyceollins per gram of product (76.8% glyceollin I, 9.9% glyceollin II, and 13.6% glyceollin III), as determined by high pressure liquid chromatography (HPLC) and UV-monitoring (visible spectrophotometry). Relative isoflavone content was also measured using HPLC (by the manufacturer) and reported in aglycone units as 61.5% genistein, 34.6% daidzein, and 3.8% glyceitin for SOY and 52.6% genistein, 43.0% daidzein, and 4.4% glyceitin for GLY. Diets were isocaloric and similar in macronutrients, cholesterol, calcium, and phosphorus. The soy protein isolate was provided by The Solae Company (St. Louis, Mo., USA), while the glyceollin-enriched protein was provided through collaborative efforts of The Solae Company; the Southern Regional Research Center, United States Department of Agriculture; and the Tulane University School of Medicine. Estradiol tablets were obtained from Mylan Pharmaceuticals (Morganton, W. Va.).

Animals were fed ~120 kcal per kg body weight (BW) once daily. Daily doses of isoflavones, glyceollins, and E2 were scaled to 1800 kcal of diet (rather than BW) to account for differences in metabolic rates between the monkeys and human subjects (Schneider et al 2004). Monkeys were thus given 0.44 mg (C/L), 12.91 mg (SOY), or 12.57 mg (GLY) of isoflavones/kg BW; 8.94 mg glyceollins/kg BW (GLY); and 66.7 μg of E2/kg BW (all groups) each day. All procedures involving animals were conducted in compliance with State and Federal laws, standards of the U.S. Department of Health and Human Services, and guidelines established by the Wake Forest University Institutional Animal Care and Use Committee. The facilities and laboratory animal program of Wake Forest University are fully accredited by the Association for the Assessment and Accreditation of Laboratory Animal Care.

Gene Microarrays and Quantitative Gene Expression Assays

For microarray analyses, total RNA was extracted from frozen mammary fat biopsies using Tri Reagent (Molecular Research Center, Cincinnati, Ohio), purified using RNeasy Mini kit (QIAGEN, Valencia, Calif.), and quantitated using a NanoDrop ND-1000 UV-vis spectrophotometer (NanoDrop, Wilmington, Del.). Biopsy collection has been described previously (Wood et al 2006). RNA intactness and quality were confirmed using an Agilent 2100 Bioanalyzer (Agilent Technologies, Wilmington, Del.). The 3 highest quality samples from each group (n=12 total) were used for microarray analysis. RNA was hybridized to GeneChip Rhesus Macaque Genome Arrays (Affymetrix, Santa Clara, Calif.), washed, and scanned at Cogenics®, a Division of Clinical Data (Morrisville, N.C.). Intensity data were extracted from scanned images using GeneChip Operating Software (Affymetrix). Expression of ten gene targets related to lipid and glucose metabolism pathways (identified on microarray analysis) were determined using quantitative real-time polymerase chain reaction (qRT-PCR). Macaque-specific qRT-PCR primer-probe sets were generated for the internal control genes GAPDH and BACT, while rhesus macaque or human ABI Taqman primer-probe sets were used for target assays (see TABLE 11, showing primer/probe sets for target genes evaluated by qRT-PCR). Total RNA was extracted, quantitated, and reverse-transcribed as above from all mammary samples (n=30). Real-time PCR reactions were performed on an Applied Biosystems ABI PRISM® 7500 Fast Sequence Detection System using Taqman reagents and standard thermocycling protocol. Relative expression was determined using the ΔΔCt method calculated by ABI Relative Quantification 7500 Software v2.0.1. Stock mammary tissue was run in duplicate on each plate as an external calibrator.

TABLE 11

| Gene ID | Description | NCBI RefSeq | Species | ABI assay ID |
|---|---|---|---|---|
| ACTB | actin, beta | DQ464112 | Mf | (custom) |
| ADIPOQ | adiponectin | NM_001032871 | Mm | Rh02788052_m1 |
| AGPAT2 | lysophosphatidic acid acyltransferase, beta | XM_001094264 | Mm | Rh02832953_m1 |
| DGAT2 | diacylglycerol O-acyltransferase 2 | NM_032564.3 | Hs | Hs01045911_m1 |
| GAPDH | glyceraldehyde-3-phosphate dehydrogenase | DQ464111 | Mf | (custom) |
| GPAM | glycerol-3-phosphate acyltransferase, mitochondrial | XM_001088103 | Mm | Rh02878272_m1 |
| GPD1 | glycerol-3-phosphate dehydrogenase 1 | XM_001102726 | Mm | Rh02857284_m1 |
| GYS1 | glycogen synthase 1 | NM_001032886 | Mm | Rh01102890_m1 |
| LASS6 | LAG1 homolog, ceramide synthase 6 | XM_001102396 | Mm | Rh02891284_m1 |
| LEP | leptin | NM_001042755 | Mm | Rh02788316_m1 |
| LPIN1 | lipin 1 | NM_145693 | Hs | Hs01041902_m1 |
| LPL | lipoprotein lipase | NM_000237.2 | Hs | Hs01012569_m1 |
| PLIN | perilipin 1 | NM_002666.3 | Hs | Hs01106922_m1 |
| PPARA | peroxisome proliferator-activated receptor alpha | NM_001033029 | Mm | Rh00947536_m1 |
| PPARG | peroxisome proliferator-activated receptor gamma | NM_138711 | Hs | Hs01115511_m1 |
| PPARGC1A | peroxisome proliferator-activated receptor gamma, coactivator 1 alpha | XM_001105289 | Mm | Rh01016729_m1 |
| PPARGC1B | peroxisome proliferator-activated receptor gamma, coactivator 1 beta | NM_133263.2 | Hs | Hs00370186_m1 |
| SCD | stearoyl-CoA desaturase | XM_001107910 | Mm | Rh02929461_m1 |
| SORBS1 | sorbin and SH3 domain containing 1 | NM_001034954 | Hs | Hs00908952_m1 |

For TABLE 7, Hs=*Homo sapiens*; Mf=*Macaca fascicularis* (cynomolgus macaque); Mm=*Macaca mulatta* (rhesus macaque).

Serum Markers

Blood was collected at baseline and post-treatment for measurement of serum markers. Serum concentrations of total glyceollins (I-III) and soy isoflavonoids were determined by liquid chromatographic-photodiode array mass spectrometric analysis. Serum concentrations of E2, vascular and bone turnover markers (monocyte chemoattractant protein (MCP)-1, endothelin (ET)-1, and CrossLaps collagen degradation products (XLAPs)), and metabolic markers (insulin, glucagon-like peptide (GLP)-1), adiponectin, and leptin) were measured using commercially available kits and protocols for radioimmunoassay (E2, DSL-4800 ultra-sensitive from Diagnostic Systems Laboratories, Webster, Tex.) or enzyme-linked immunosorbent assays (MCP-1 and ET-1 from R&D Systems, Minneapolis, Minn.; XLAPs from Osteometer Biotech A/S, Herlev, Denmark; GLP-1 (Total), leptin, and insulin from ALPCO Diagnostics, Salem, N.H.; and adiponectin from Mercodia, Winston-Salem, N.C.). Total cholesterol (TC), high-density lipoprotein cholesterol (HDL), and triglyceride (TG) concentrations were measured using enzymatic methods on a COBAS FARA II analyzer (Roche Diagnostics, Montclair, N.J.) with standard protocols and reagents. Serum assays were run in a fully standardized clinical chemistry laboratory at Wake Forest University School of Medicine. HDL concentrations were measured using the heparin-manganese precipitation procedure. Low-density lipoprotein cholesterol (LDL) plus very low-density lipoprotein cholesterol (VLDL) was calculated as the difference between TPC and HDL. Samples from baseline and post-treatment timepoints were run at the same time for all serum measures.

Statistical Analyses

Microarray data were analyzed using the GeneSifter® software program (Geospiza, Seattle, Wash.). Intensity data were RMA-normalized, converted to a log 2 scale, screened for heterogeneity among samples and groups, and evaluated using supervised analysis of variance (ANOVA) and pairwise comparisons between treatments. Principal components analysis (PCA), pattern navigation, cluster analysis, heat-mapping, and KEGG pathway analyses were performed on filtered data subsets, as described in results. Differences in gene numbers altered by each treatment were compared using a Chi-Square Test. Euclidean distances (representing the numeric difference between treatment vectors) were calculated as part of hierarchical clustering dendrograms using average linkage. Pathways were evaluated via KEGG analyses; a z-score>2.0 was considered a significant overrepresentation of genes in a particular pathway. Representation of differentially expressed genes within specific canonical and functional categories was evaluated using Ingenuity Pathway Analysis (IPA) software v8.0 (Ingenuity Systems, Redwood City, Calif.). Significance of gene numbers within a given category was determined in IPA using a Fisher's Exact Test with Benjamini and Hochberg correction and expressed as −log 10 (P value) for each treatment group. Other data were analyzed using the SAS statistical package (version 9.1, SAS Institute; Cary, N.C.). A general linear model was used to determine mean values and calculate group differences. All data were evaluated for normal distribution and homogeneity of variances among groups. Gene expression and serum marker data were log-transformed to improve distribution, and data were then retransformed to original scale and reported as fold-change of control with 90% confidence interval. One animal in the SOY group was excluded from gene expression analyses based on poor RNA quality. Final group sizes were thus n=9 for C/L and n=10 for SOY and n=10 for GLY for qRT-PCR data. Post-treatment serum lipid and marker data were covaried by baseline values. All pairwise P-values were adjusted for the number of pairwise tests using a Bonferroni correction. A two-tailed significance level of 0.05 was chosen for all comparisons.

Example 6

Dietary Intake

Body weight, serum E2, and serum isoflavonoids were measured as indicators of diet intake. Treatment groups did not differ significantly in mean BW at baseline or post-treatment, in BW change, or in serum E2 concentrations (ANOVA P>0.05 for all). Mean serum glyceollin concentrations were 134.2±34.6 nmol/L in the GLY group and negligible in the SOY group at 4 hours post-feeding (P<0.001 compared to GLY), while total serum isoflavonoid concentrations were significantly higher in the SOY and GLY groups compared to C/L group at 4 hours (P<0.001 for both) and 24 hours (P<0.05 for both) post-feeding. The SOY and GLY groups did not differ in total serum isoflavonoids at either 4 hours (P=0.59) or 24 hours (P=0.73) post-feeding; individual isoflavonoids were also comparable between the two diets. Total serum isoflavonoids for the SOY and GLY diets at 4 hours post-feeding were comparable to those reported in human soy intervention studies.

Example 7

Gene Expression Profiles in Mammary Fat for Diets Containing Casein/Lactalbumin (C/L), Standard Soy Protein (SOY), and Glyceollin-Enriched Soy Protein (GLY)

Figure 3:
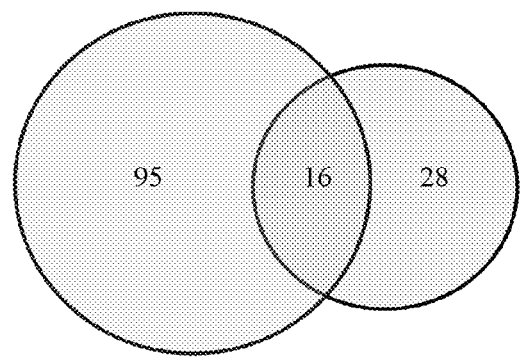
FIG. 3 is a Venn diagram showing the total number of genes (with GenBank identifiers) with FC>1.5, ANOVA P<0.05, quality>2, and t-test P<0.05 compared to casein/lactalbumin.
Figure 4A:
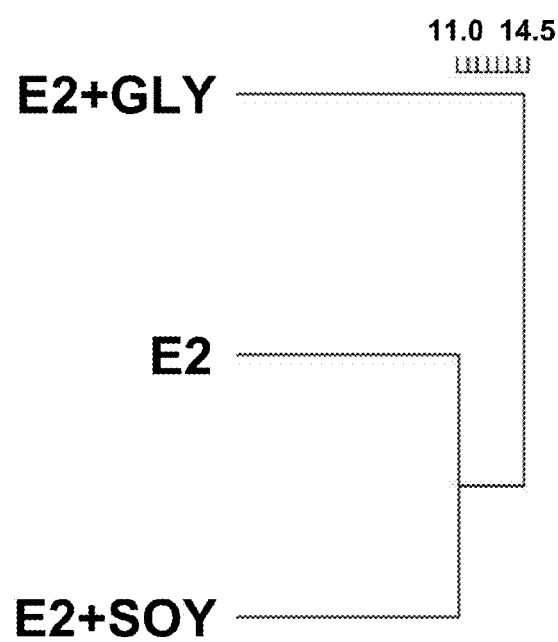
FIG. 4A shows a hierarchical clustering dendrogram.
Figure 4B:
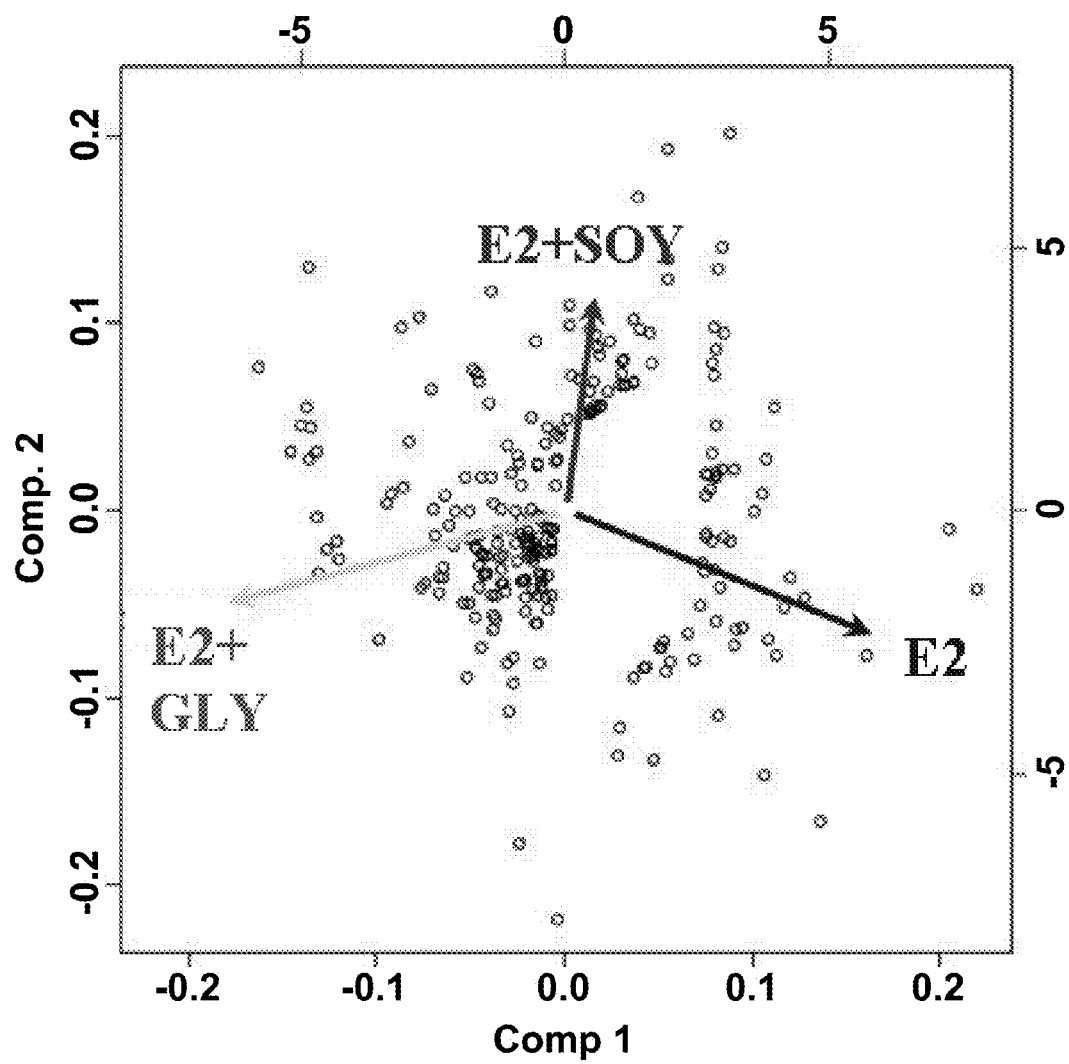
FIG. 4B shows a principal component analysis for gene probes with FC>1.5 and ANOVA P<0.05 (n=252). Euclidean distance and average linkage were used for dendrogram and clustering.
Figure 5:
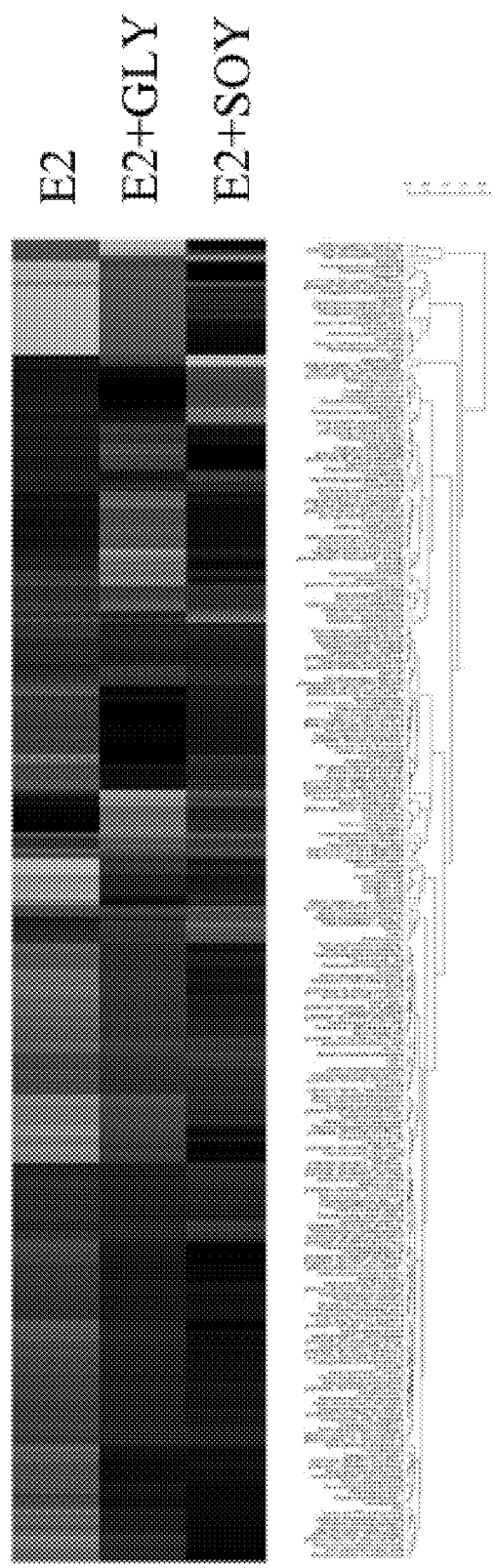
FIG. 5 shows that the distinction in profiles for glyceollin from standard soy protein was also evident qualitatively from heatmaps for genes altered at FC>1.5.
Figure 6:
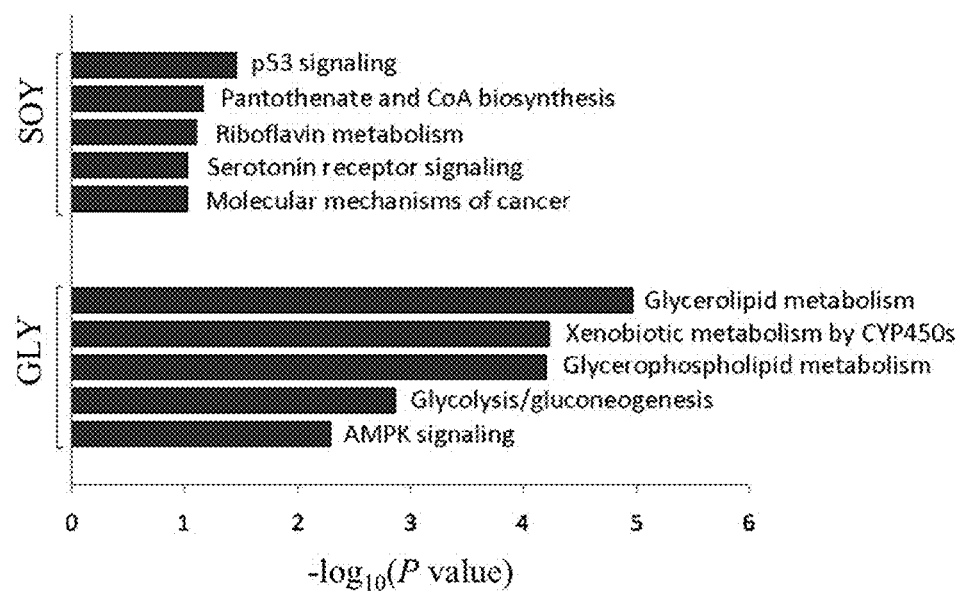
FIG. 6 shows the pathway analyses that were used to sort altered genes by canonical and functional categories. The most overrepresented canonical pathways in IPA for altered genes in the glyceollin group all related to lipid, carbohydrate, and/or energy metabolism (significantly altered at FC>1.5 by GLY and SOY diets by Ingenuity pathway analysis). These pathways included glycerophospholipid and glycerolipid metabolism, cytochrome p450 metabolism, and AMPK signaling (P<0.01 for all).

Global expression profiles showed greater numbers of genes altered by GLY compared to SOY. For example, among 139 total (named) genes with FC>1.5 and ANOVA P<0.05, a greater number were altered in the GLY group (n=111) compared to the SOY group (n=44) (P<0.001 by Chi-square test) with only 14% overlap of GLY genes with SOY genes (FIG. 3). FIG. 3 demonstrates that global expression profiles showed greater numbers of genes altered by glyceollin compared to standard soy protein. For example, among 139 total (named) genes with FC>1.5 and ANOVA P<0.05, a greater number were altered in the glyceollin group (n=111) compared to the standard soy protein group (n=44) (P<0.001 by Chi-square test) with only 14% overlap of glyceollin genes with standard soy protein genes. Supervised hierarchical clustering indicated that C/L and SOY (rather than GLY and SOY) were the most closely associated groups with a Euclidean distance of ~11 for genes significantly altered at FC>1.5 (FIG. 4). FIG. 4 shows that supervised hierarchical clustering indicated that casein/lactalbumin and standard soy protein (rather than glyceollin and standard soy protein) were the most closely associated groups with a Euclidean distance of ~11 for genes significantly altered at FC>1.5. The distinction in profiles for glyceollin from standard soy protein was also evident qualitatively from PCA vectors for genes altered at FC>1.5. The distinction in profiles for GLY from SOY was also evident qualitatively from PCA vectors (FIG. 4) and heatmaps (FIG. 5) for genes altered at FC>1.5. A complete list of all significantly altered genes at FC>1.5 by ANOVA and by supervised pairwise comparisons is provided in TABLE 9. TABLE 9 shows the ten gene targets related to lipid and/or carbohydrate metabolism, PPAR and AMPK signaling, and/or adipocytokine activity that were evaluated by qRT-PCR. Of these targets, eight out of ten were upregulated in the glyceollin group compared to casein/lactalbumin (P<0.05 for all) while none of the ten differed between standard soy protein and casein/lactalbumin groups.

Example 8

Pathway Analyses

Pathway analyses were used to sort altered genes by canonical and functional categories. The most overrepresented canonical pathways in IPA for altered genes in the GLY group all related to lipid, carbohydrate, and/or energy metabolism. These pathways included glycerophospholipid and glycerolipid metabolism, cytochrome p450 metabolism, and AMPK signaling (P<0.01 for all) (see TABLE 8, which shows genes significantly altered by GLY and standard soy protein diets (related to lipid, glucose, and energy metabolism) by KEGG pathway analysis; pathways were identified by KEGG analysis from gene probes with FC>1.5, P<0.05, and >2 genes altered in the pathway; only pathways with significant z-score (>2) are shown.); notable pathways include glycerolipid metabolism, peroxisome proliferator-activating receptor (PPAR) signaling, and cytochrome p450 metabolism. Overrepresentation of pathways with significant z-score or related pathways was not seen for the SOY group. The most overrepresented functional pathways in IPA for GLY genes were lipid metabolism, small molecule biochemistry, and carbohydrate metabolism (P<0.05 for all). The most significant subcategory within lipid metabolism was triacylglycerol biosynthesis (−log 10 (P value)=6.9). Similar patterns were seen with KEGG pathway analysis, which revealed significant overrepresentation of altered genes (z-score>2) for the GLY group related to lipid, glucose, and energy metabolism (TABLE 8). Notable pathways here included glycerolipid metabolism, peroxisome proliferator-activating receptor (PPAR) signaling, and cytochrome p450 metabolism.

TABLE 8

| Pathway | list | # ↑ | # ↓ | geneset | z-score ↑ | z-score ↓ |
|---|---|---|---|---|---|---|
| GLY (z-score > 2) | | | | | | |
| Glycerophospholipid metabolism | 6 | 6 | 0 | 58 | 7.03 | −0.36 |
| Glycerolipid metabolism | 4 | 4 | 0 | 37 | 5.88 | −0.29 |
| Metabolism of xenobiotics by cytochrome P450 | 4 | 4 | 0 | 58 | 4.42 | −0.36 |
| Tyrosine metabolism | 3 | 3 | 0 | 44 | 3.79 | −0.32 |
| Drug metabolism - cytochrome P450 | 3 | 3 | 0 | 55 | 3.24 | −0.35 |
| PPAR signaling pathway | 3 | 3 | 0 | 57 | 3.16 | −0.36 |
| ECM-receptor interaction | 4 | 3 | 1 | 77 | 2.49 | 2.02 |
| Hypertrophic cardiomyopathy | 3 | 2 | 1 | 73 | 1.44 | 2.09 |
| Autoimmune thyroid disease | 3 | 1 | 2 | 48 | 0.71 | 5.82 |
| SOY (z-score > 2) | | | | | | |
| Hypertrophic cardiomyopathy | 3 | 3 | 0 | 73 | 5.76 | −0.30 |
| ECM-receptor interaction | 4 | 3 | 1 | 77 | 5.58 | 2.96 |
| Focal adhesion | 4 | 3 | 1 | 184 | 3.20 | 1.65 |

Example 9

Quantitative Gene Expression

To further examine these findings, ten gene targets related to lipid and/or carbohydrate metabolism, PPAR and AMPK signaling, and/or adipocytokine activity were evaluated by qRT-PCR. Nine out of the 16 targets evaluated were upregulated in the GLY group compared to C/L (P<0.05 for all) while none of the 16 differed between SOY and C/L groups (see TABLE 9, showing dietary protein effects on relative expression of select genes related to lipid and glucose metabolism, PPAR signaling, and adipocytokine activity within mammary adipose tissue, as determined by qRT-PCR). Targets increased in the GLY group included genes for adipocytokine signaling (adiponectin and leptin), carbohydrate metabolism (glycerol-3-phosphate dehydrogenase and glycogen synthase), PPAR signaling (PPARγ and lipin1), and lipid metabolism (lipoprotein lipase and perilipin). It is worth noting that considerable crosstalk occurs among these categories and that particular molecules may thus function in multiple pathways.

TABLE 9

| Gene | C/L | SOY | GLY | Pathways |
|---|---|---|---|---|
| ADIPOQ | 1.0 (0.7-1.3) | 1.5 (1.2-1.9) | 3.2 (2.6-3.8)**,# | adipocytokine & PPAR signaling; type II diabetes |
| DGAT2 | 1.0 (0.7-1.4) | 2.6 (2.1-3.2) | 3.0 (2.5-3.6)* | glycerolipid metabolism, triglyceride biosynthesis |
| GPAM | 1.0 (0.8-1.2) | 1.1 (0.9-1.3) | 1.8 (1.6-2.1) | glycerolipid, glycerophospholipid, & fatty acid metabolism, triglyceride biosynthesis |
| GPD1 | 1.0 (0.7-1.3) | 2.0 (1.6-2.5) | 3.4 (2.8-4.2)** | glycerolipid, glycerophospholipid, & carbohydrate metabolism, gluconeogenesis |
| GYS1 | 1.0 (0.8-1.2) | 1.4 (1.2-1.6) | 1.9 (1.6-2.1)** | starch metabolism, insulin signaling |
| LASS6 | 1.0 (0.8-1.2) | 0.6 (0.4-0.7) | 0.5 (0.4-0.7) | lipid biosynthesis |
| LEP | 1.0 (0.7-1.4) | 2.4 (1.8-3.3) | 4.4 (3.4-5.9)** | adipocytokine, Jak-STAT, & cytokine-cytokine signaling |
| LPIN1 | 1.0 (0.8-1.3) | 1.9 (1.6-2.4) | 2.7 (2.2-3.2)* | PPAR & insulin signaling; triglyceride & nutrient metabolism |
| LPL | 1.0 (0.8-1.3) | 1.4 (1.1-1.7) | 2.7 (2.2-3.3)** | glycerolipid metabolism; PPAR signaling |
| PGC1A | 1.0 (0.7-1.3) | 0.6 (0.4-0.8) | 0.9 (0.7-1.1) | adipocytokine & insulin signaling pathways; glucose homeostasis; fatty acid oxidation; gluconeogenesis |
| PGC1B | 1.0 (0.8-1.2) | 0.9 (0.7-1.1) | 1.1 (1.0-1.3) | PPAR, estrogen receptor, & glucocorticoid signaling |
| PLIN | 1.0 (0.8-1.3) | 1.6 (1.3-1.9) | 2.7 (2.2-3.2)** | PPAR signaling |
| PPARA | 1.0 (0.8-1.2) | 1.0 (0.8-1.2) | 1.1 (0.9-1.3) | adipocytokine & PPAR signaling |
| PPARG | 1.0 (0.7-1.5) | 2.4 (1.7-3.5) | 5.6 (4.0-7.8)** | adipocytokine & PPAR signaling |
| SCD | 1.0 (0.6-1.5) | 2.2 (1.6-3.0) | 2.3 (1.6-3.1) | fatty acid biosynthesis, PPAR signaling |
| SORBS1 | 1.0 (0.8-1.2) | 1.2 (1.0-1.5) | 1.8 (1.5-2.1) | PPAR & insulin signaling |

Values represent mean fold-change relative to C/L diet with 90% confidence interval.
*$P < 0.05$ vs C/L;
**$P < 0.01$ vs C/L;
$P < 0.05$ vs SOY.

Example 10

Serum Markers

Serum lipid measures did not differ significantly among groups at baseline (ANOVA $P>0.05$ for all). Following treatment, the GLY group had lower TC and LDL+VLDL compared to C/L and SOY groups ($P<0.01$ for all) and greater TG compared to C/L ($P=0.008$) (see TABLE 10, showing treatment effects on serum lipids, vascular, bone turnover, and metabolic markers). The SOY group also had greater TG compared to the C/L group ($P=0.02$). No significant group differences were seen for HDL or TC to HDL ratio. No group differences were observed for serum MCP-1, ET-1, XLAPS, or metabolic markers at baseline or post-treatment (ANOVA $P>0.05$ for all).

TABLE 10

| | C/L | SOY | GLY |
|---|---|---|---|
| Lipids | | | |
| TC (mg/dl) | 337 (311-364) | 322 (300-345) | 225 (210-242)**,## |
| TG (mg/dl) | 53 (45-62) | 97 (85-112)* | 108 (93-126)** |
| HDL (mg/dl) | 43 (37-50) | 46 (40-53) | 49 (42-57) |
| VLDL + LDL (mg/dl) | 282 (257-309) | 262 (241-284) | 171 (157-186)**,## |
| TC/HDL | 7.4 (6.3-8.8) | 7.1 (6.1-8.2) | 4.7 (4.1-5.5) |
| Vascular and bone markers | | | |
| MCP-1 (pg/ml) | 194 (178-212) | 206 (189-223) | 189 (174-205) |
| ET-1 (pg/ml) | 1.76 (1.53-2.03) | 1.38 (1.21-1.56) | 1.30 (1.13-1.49) |
| XLAPs (ng/ml) | 0.92 (0.82-1.02) | 0.91 (0.82-1.01) | 0.84 (0.75-0.94) |
| Metabolic markers | | | |
| Insulin (mU/L) | 16.7 (14.0-19.8) | 20.0 (17.1-23.4) | 19.0 (16.1-22.4) |
| GLP-1 (pmol/L) | 4.1 (3.1-5.3) | 2.7 (2.1-3.4) | 2.8 (2.1-3.5) |
| Adiponectin (ug/ml) | 4.7 (4.0-5.5) | 3.1 (2.6-3.6) | 4.8 (4.1-5.5) |
| Leptin (ng/ml) | 1.1 (0.9-1.3) | 1.4 (1.2-1.6) | 0.9 (0.7-1.0) |

TC = total cholesterol;
LDL = low density lipoprotein;
VLDL = very low density lipoprotein;
HDL = high density lipoprotein;
TG = triglyceride;
GLP-1 = glucagon-like peptide-1

TABLE 10 demonstrates that serum lipid measures did not differ significantly among groups at baseline (ANOVA $P>0.05$ for all). Following treatment, the glyceollin group had lower total cholesterol and low density lipoprotein+very low density lipoprotein compared to casein/lactalbumin and standard soy protein groups ($P<0.01$ for all) and greater triglyceride compared to casein/lactalbumin ($P=0.008$). The values of TABLE 10 represent mean (90% confidence interval) at post-treatment covaried by baseline measures. P values were corrected for multiple pairwise comparisons. For conversion of lipid values to SI units (mmol/l), divide by 38.67 for TC, LDL+VLDL, and HDL, and by 88.57 for TG. Symbols indicate significant differences with casein/lactalbumin group (*$P<0.05$, **$P<0.01$) or with standard soy protein group (##$P<0.01$).

Glyceollins are a novel class of phytoalexin compounds produced as defense molecules in response to stress by certain types of leguminous plants, most notably soy. In this study we evaluated transcriptional profiles in mammary adipose tissue resulting from glyceollin-enriched soy protein in comparison with a standard soy protein isolate. We identified a distinct gene expression profile for GLY that showed minimal overlap with that of SOY. The effects of GLY related primarily to pathways involved in lipid and carbohydrate metabolism, including PPAR and adipocytokine signaling, lipoprotein lipase, and triglyceride metabolism. The GLY diet also resulted in lower serum total cholesterol, specifically non-high-density lipoprotein cholesterol, compared to the C/L diet. These preliminary findings suggest that glyceollin-enriched soy protein has divergent effects from standard soy related to adipocyte activity and nutrient metabolism.

Diet is a major determinant of metabolic syndrome and related comorbid conditions, and dietary interventions with beneficial metabolic effects may have an important role in breast cancer prevention. Prior findings suggest that glyceollins may competitively bind estrogen receptors (ERs) and elicit selective ER-modulating properties distinct from soy isoflavonoids. The role of specific isoflavonoids and their derivatives in modulating metabolic pathways remains poorly understood. Notable genes upregulated by the GLY diet included PPARγ, adiponectin, lipin 1, and lipoprotein lipase.

Prior results have shown that glyceollins may function as natural selective ER modulators. Results of this pilot study suggest that glyceollin-enriched soy protein may also have biologically relevant effects on pathways related to lipid, carbohydrate, and energy metabolism. The present inventors' findings demonstrate that soybean treatment prior to processing may alter the profile of bioactive constituents in soy protein, leading to distinct physiologic and metabolic effects from standard soy protein isolates. This idea may also have important implications for the identification of bioactive components in other plant-based foods.

Materials and Methods: Glucose Uptake

Solutions

Krebs-Ringers-Hepes (KRH) buffer was prepared with 200 mL $H_2O$, 300 µL of 1 M $CaCl_2$, 300 µL of 1.2 M $MgSO_4$, 300 µL of 1 M $KH_2PO_4$, 3 mL of 0.14 M KCl, 6 mL of 1 M HEPES in 1.2 M $NaHCO_3$, and 15 mL of 2.6 M NaCl. The pH was adjusted to 7.4 $H_2O$ was added to bring the final volume to 300 mL. The resulting solution was filter sterilized with a 0.22 µm filter.

D-glucose (MW=180.16) stock solution (100 mM) was prepared by dissolving 180.16 mg D-glucose in 10 mL $H_2O$.

Tracer working solution was prepared fresh for each plate by adding 3 µl of tracer stock solution (1 µCi/µl) to 297 µL of 100 mM D-glucose to yield 0.1 µCi [$^3$H]2-deoxyglucose in 99 mM glucose. 10 µL was added to each well with a final volume in each well of 1000 µL=0.1 µCi at 0.99 mM D-glucose.

Insulin (MW=5808) stock solution (100 µM) was prepared by dissolving 2.90 mg insulin into 5 mL of 0.01 N HCl. To make working solutions: the stock solution was diluted 1:10 by adding 100 µL stock to 900 µL KRH buffer, giving solution A (10 µM); solution A was diluted by adding 400 µL of solution A to 932 µL KRH buffer, giving solution B (3 µM); solution A was diluted by adding 100 µL of solution A to 900 µL KRH buffer, giving solution C (1 µM); solution B was diluted by adding 100 µL of solution B to 900 µL KRH buffer, giving solution D (300 nM); solution C was diluted by adding 100 µL of solution C to 900 µL KRH buffer, giving solution E (100 nM); solution D was diluted by adding 100 µL of solution D to 900 µL KRH buffer, giving solution F (30 nM); solution E was diluted by adding 100 µL of solution E to 900 µL KRH buffer, giving solution G (10 nM); solution F was diluted by adding 100 µL of solution F to 900 µL KRH buffer, giving solution H (3 nM); solution G was diluted by adding 100 µL of solution G to 900 µL KRH buffer, giving solution I (1 nM); and solution H was diluted by adding 100 µL of solution H to 900 µL KRH buffer, giving solution J (0.3 nM). 100 µL of each concentration was added to each well with a final volume in each well of 1000 µL (1:10 dilution when added to cells).

A 10 mM stock glyceollin solution was prepared by combining 3.38 mg of mixture of glyceollin I (about 76.8%), glyceollin II (about 9.9%), and glyceollin III (about 13.6%) with 1 mL DMSO. This stock solution was kept refrigerated. To make working solutions: 80 µL of the stock solution was diluted with 3920 µL KRH buffer, giving solution A (200 µM); solution A was diluted by adding 500 µL of solution A to 335 µL KRH buffer, giving solution B (120 µM); solution A was diluted by adding 1000 µL of solution A to 1000 µL KRH buffer, giving solution C (100 µM); solution A was diluted by adding 1000 µL of solution A to 1500 µL KRH buffer, giving solution D (80 µM); solution A was diluted by adding 1000 µL of solution A to 2330 µL KRH buffer, giving solution E (60 µM); solution D was diluted by adding 1000 µL of solution D to 1000 µL KRH buffer, giving solution F (40 µM); solution F was diluted by adding 1000 µL of solution F to 1000 µL KRH buffer, giving solution G (20 µM); solution G was diluted by adding 1000 µL of solution G to 1000 µL KRH buffer, giving solution H (10 µM); and solution H was diluted by adding 1000 µL of solution H to 1000 µL KRH buffer, giving solution I (5 µM). 100 µL of each concentration was added to each well with a final volume in each well of 1000 µL (1:10 dilution when added to cells). Unless indicated otherwise (see, e.g., EXAMPLES 14 & 15), where the EXAMPLES below refer to glyceollin, a mixture of glyceollins I, II, and III, was used.

Cells

Cell culture and differentiation of murine 3T3-L1 cells is a well-accepted model for study of adipocyte differentiation, glucose uptake, and insulin action. These cells undergo a program of differentiation manifest by large lipid droplet accumulation when stimulated by the appropriate hormonal cocktail. The adipocytes express markers such as leptin and adiponectin, express Glut 4, and respond to insulin stimulation by increasing glucose uptake, similar to primary adipocytes. For these experiments, frozen preadipocytes were purchased from Zenbio (Research Triangle Park, N.C.). They were thawed at 37° C., diluted with Zenbio Preadipocyte medium, and incubated in 24-well plates at 37° C. in a humidified atmosphere containing 95% air and 5% $CO_2$ until confluent. Signals derived from confluency were allowed by incubating for 2 more days. Preadipocyte medium was replaced with Zenbio Differentiation Medium and the cells were incubated for 3 additional days; that medium was replaced with Zenbio Adipocyte Maintenece medium for about 2 weeks when greater than 95% of the cells appeared filled with large lipid droplets.

Example 11

Glucose Stimulation & Glyceollin Incubation

Figure 9:
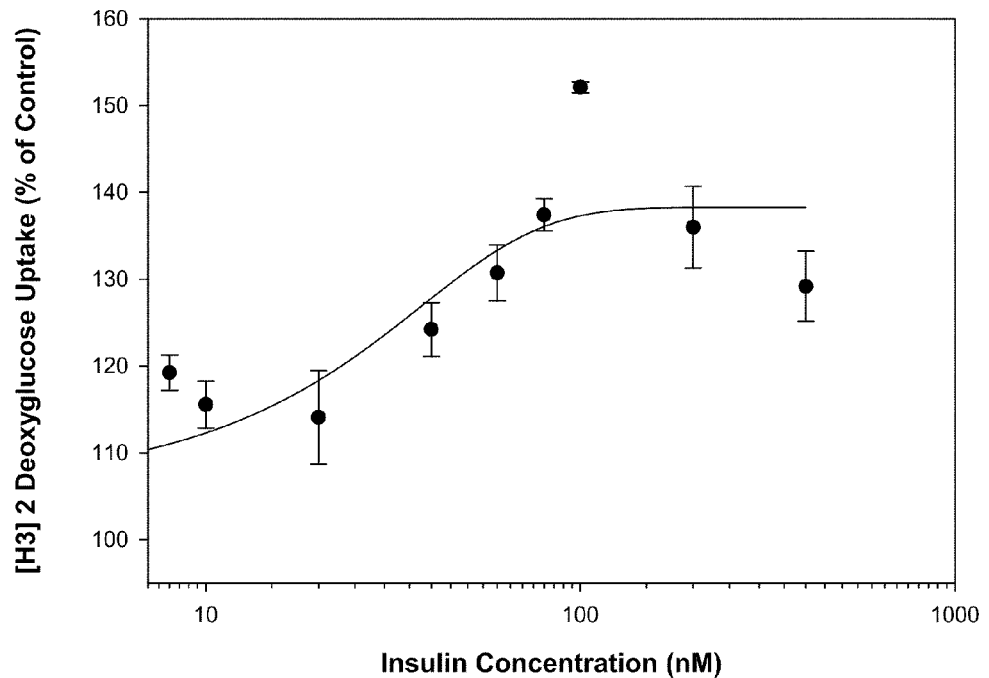
FIG. 9 is a dose-response curve showing insulin-mediated glucose uptake by 3T3-L1 adipocytes.
Figure 10:
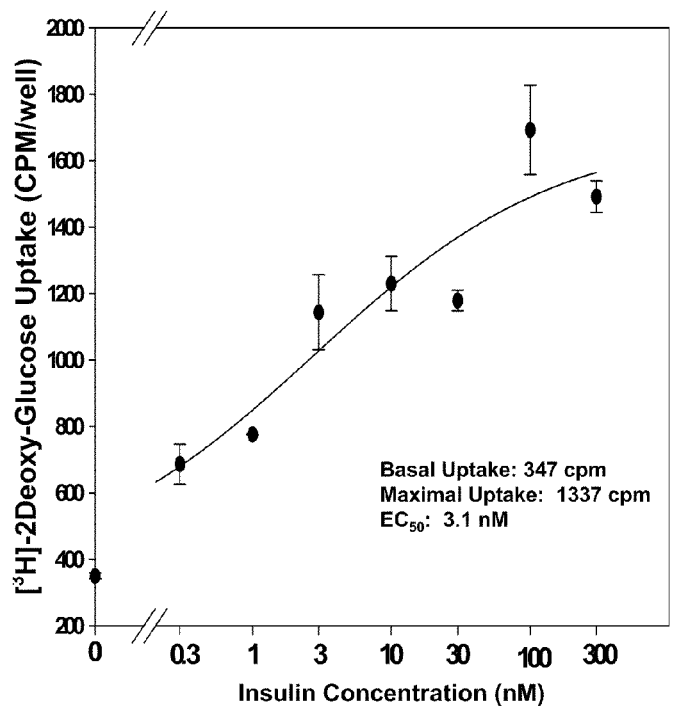
FIG. 10 is a dose-response curve showing insulin-mediated glucose uptake by 3T3-L1 adipocytes starved of adipocyte maintenance medium for 24 hours prior to the experiment.
Figure 11:
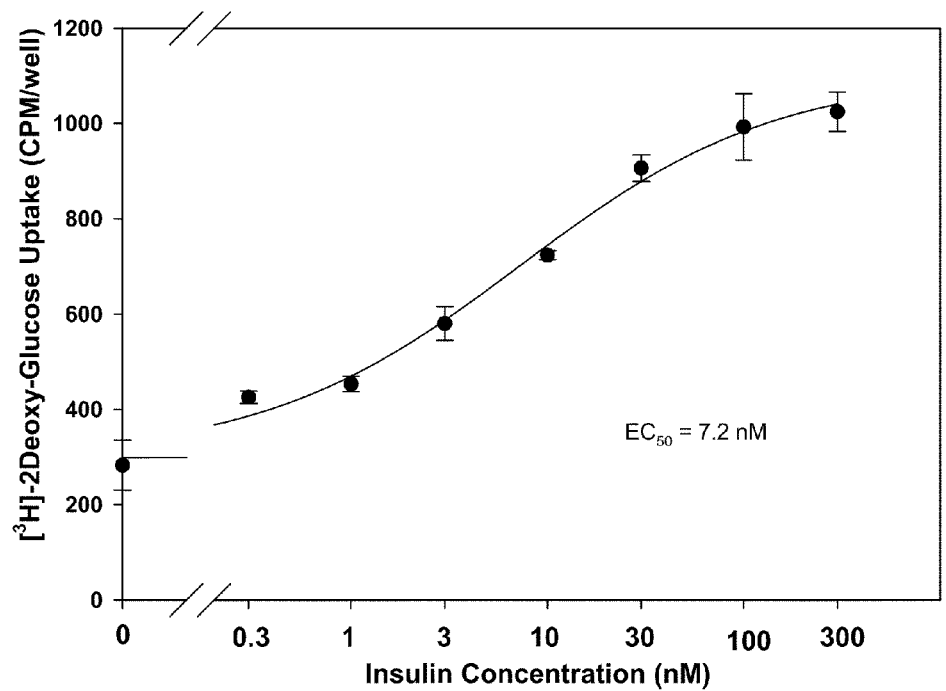
FIG. 11 is a dose-response curve, generated using a rapid-pipetting technique, showing insulin-mediated glucose uptake by 3T3-L1 adipocytes.

Glucose uptake assay was performed with fully differentiated 3T3-L1 adipocytes after starving the cells of serum, insulin, and glucose in the Zenbio Adipocyte Maintenece medium by incubating at 37° C. in 1 ml Krebs Ringer Buffer for different time periods as indicated in the figures after a 1 mL wash with KRH. The next day, the cells were washed once with KRH buffer, and then KRH, insulin, and/or glyceollin solutions were added to wells 1-24 according to the challenge maps at FIGS. 7 and 8. The cells were incubated, then exposed to different concentrations of glyceollin, insulin, or both for 30 min or 45 min (for glyceollin alone) at 37° C. in KRB, after which 10 µL of [$^3$H]2-deoxyglucose in D-glucose was added. Each plate was then incubated in a 37° C. water bath for 10 minutes, then placed on ice. The overlying medium was removed and replaced with 1 mL ice-cold KRH buffer, and each well was then washed twice with fresh ice-cold KRH buffer. The KRH buffer was removed, and 500 µL of radio-immunoprecipitation assay (RIPA) buffer was added, after which all visible cells were washed free of (displaced from) the bottom of each well using a 1 mL pipette. From each well, 450 µL was collected for assay and measured for [$^3$H] in a liquid scintillation counter. Data were expressed as CPM/well. A similar experiment was performed in which the cells were not starved of serum prior to incubation with insulin. Those data are shown in FIG. 9, which reflects a comparatively small increase in insulin-mediated glucose uptake. As shown in FIG. 10, for example, insulin-mediated glucose uptake was greatly improved (sensitivity increased about 10× versus FIG. 9, and maximum insulin-mediated glucose uptake improved about 5×) by starving the cells of ZenBio Adipocyte Maintenance medium (which contains high levels of glucose as well as significant levels of insulin) for 24 hours by replacing the Maintenance medium with KRH. Comparison of FIGS. 9 and 10 reveals that replacement of ZenBio Adipocyte Maintenance medium with KRH buffer containing neither glucose nor insulin improved the insulin responsiveness of the cells. FIG. 11 shows another insulin dose response curve from experiments identical to those from FIG. 10, except that a rapid pipetting technique was used. These data demonstrate the potential for creating insulin resistance in this cell line. Further data demonstrate that glyceollin does not alter insulin sensitivity, as suggested by Park, S. et al. "Glyceollins, One of the Phytoalexins Derived from Soybeans under Fungal Stress, Enhance Insulin Sensitivity and Exert Insulinotropic Actions" *J. Agric. Food Chem.* 2010; 58(3):1551-1557.

Example 12

Pre-Incubation with KRH Alone or KRH with Glyceollin

Figure 12:
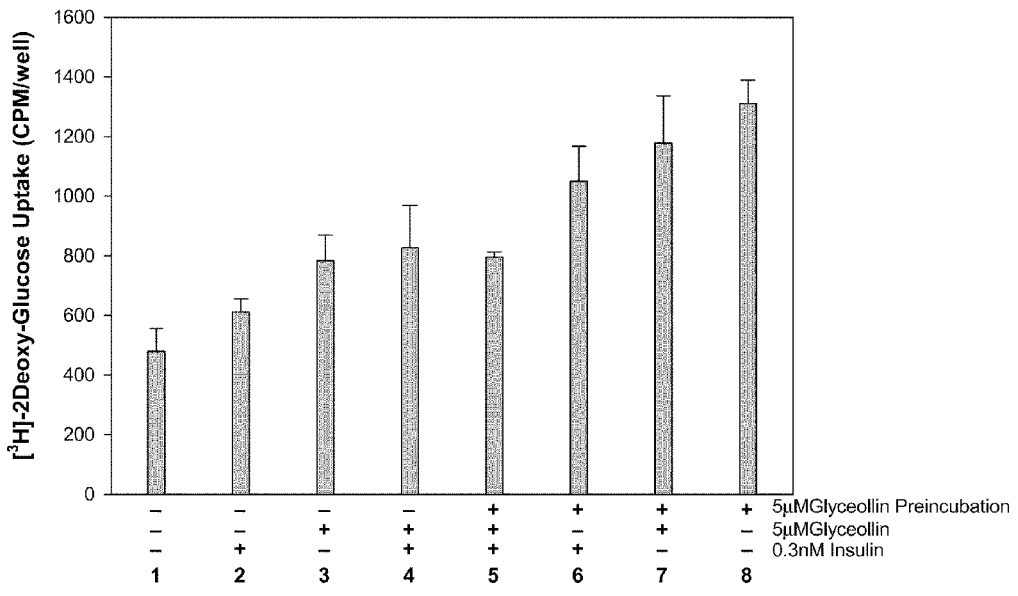
FIG. 12 shows the effects of glyceollin, insulin, or glyceollin plus insulin on glucose uptake by 3T3-L1 differentiated adipocytes pre-incubated for 24 hours with either KRH or with glyceollin.
Figure 13:
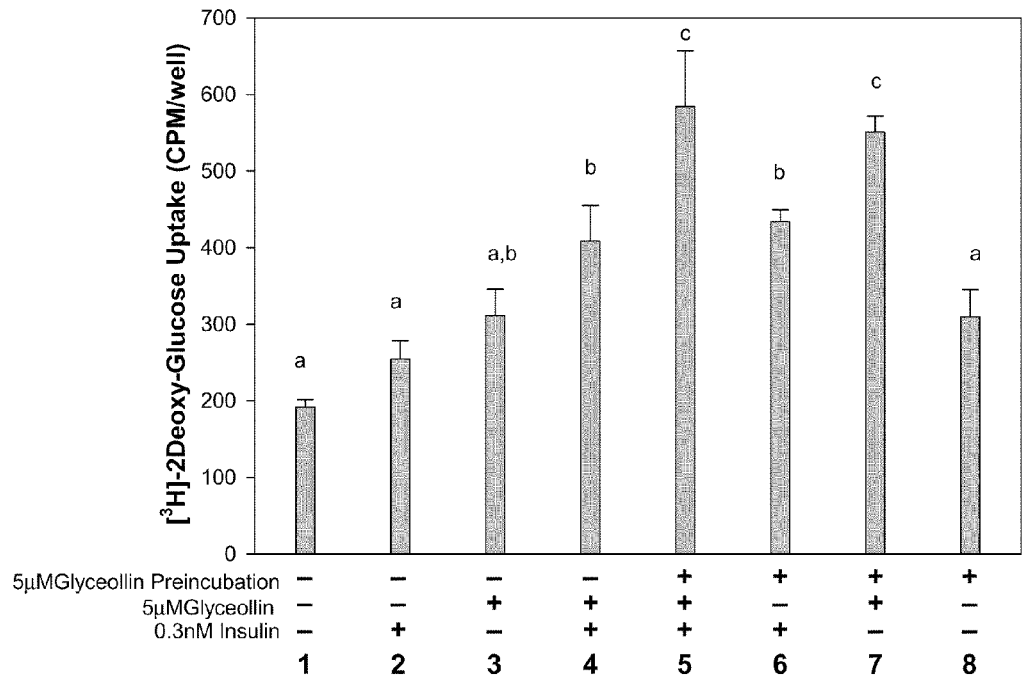
FIG. 13 shows the effects, using a rapid-pipetting technique, of glyceollin, insulin, or glyceollin plus insulin on glucose uptake by 3T3-L1 differentiated adipocytes pre-incubated for 24 hours with either KRH or with glyceollin. Columns that differ from each other by p<0.05 have differing superscript letters.

To extend the study of EXAMPLE 11, and to test whether a glyceollin present during the 24-hour serum starvation would produce measurable effects, cells were serum-starved for 24 hours by replacing the Maintenance medium with either KRH alone, or KRH supplemented with 5 µM glyceollin. Following this serum-starvation protocol, cells were exposed to 0.3 nM insulin in KRB (a very low dose) for 30 minutes at 37° C., after which 10 µL of [$^3$H]2-deoxyglucose in D-glucose was added. Glucose uptake was assayed as above. As shown in FIG. 12, in the absence of pre-incubation with glyceollin, 5 µM glyceollin alone stimulated glucose uptake to a greater degree than did 0.3 nM insulin (compare columns 2 and 3). This result is particularly surprising because it has been suggested that glyceollin does not stimulate glucose uptake without the presence of insulin. The experiment was repeated with a rapid pipetting technique and without 24-hour serum starvation, and the results are shown in FIG. 13. The results of Park et al. mirror those shown by comparison of columns 5 and 6 of FIG. 13, which was interpreted as demonstrating an increase in insulin sensitivity because glucose uptake was enhanced by addition of 5 uM glyceollin (FIG. 13, column 5). Column 3 of FIG. 13, however, again demonstrates that 5 µM glyceollin stimulates glucose uptake to an even greater degree than 0.3 nM insulin alone (see col. 2); column 4 demonstrates the combined effects of insulin and glyceollin, which appear to be at least additive and may be synergistic (comparing to either col. 2 or 3). Glyceollin has been thought to require at least 16 to 24 hours to be effective, and the pre-incubation conditions of columns 5-8 of FIG. 13 (using serum-free medium) were designed to explore this supposition. However, comparison of columns 2 and 4 of FIG. 13 represent data from cells starved of serum for 24 hours and only then stimulated with either insulin (column 2) or glyceollin with insulin (column 4) for 30 minutes, and reveal the surprising finding that glyceollin is clearly effective at stimulating glucose uptake without pre-incubation.

Example 13

Pre-Incubation with KRH Alone or KRH with Glycinol

Figure 14:
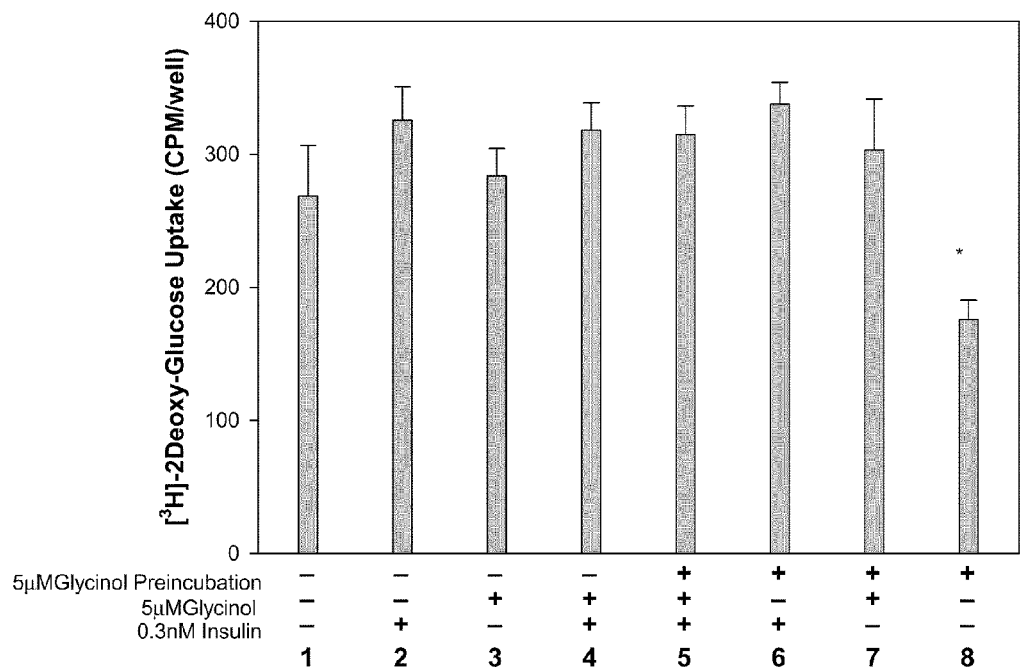
FIG. 14 shows the effects, using a rapid-pipetting technique, of glycinol, insulin, or glycinol plus insulin on glucose uptake by 3T3-L1 differentiated adipocytes pre-incubated for 24 hours with either KRH or with glycinol. The asterisk indicates significant difference from all other groups.

To test whether glycinol (instead of glyceollin) present during the 24-hour serum starvation would produce measurable effects, cells were serum-starved for 24 hours by replacing the Maintenance medium with either KRH alone, or KRH supplemented with 5 µM glycinol, and the experiments otherwise carried out as set forth for EXAMPLE 12. Glycinol is a much more potent estrogen agonist than the glyceollins; Park et al. characterize glyceollin as a selective estrogen receptor modulator (SERM) and propose that glyceollin likely enhances glucose uptake via an estrogen agonist action. As shown in FIG. 14, however, glycinol is ineffective at stimulating glucose uptake and may in fact inhibit glucose uptake (compare columns 1 & 8). These data suggest that an estrogen-mediated pathway is not responsible for stimulating glucose uptake.

Example 14

Pre-Incubation with Different Glyceollins

Figure 15:
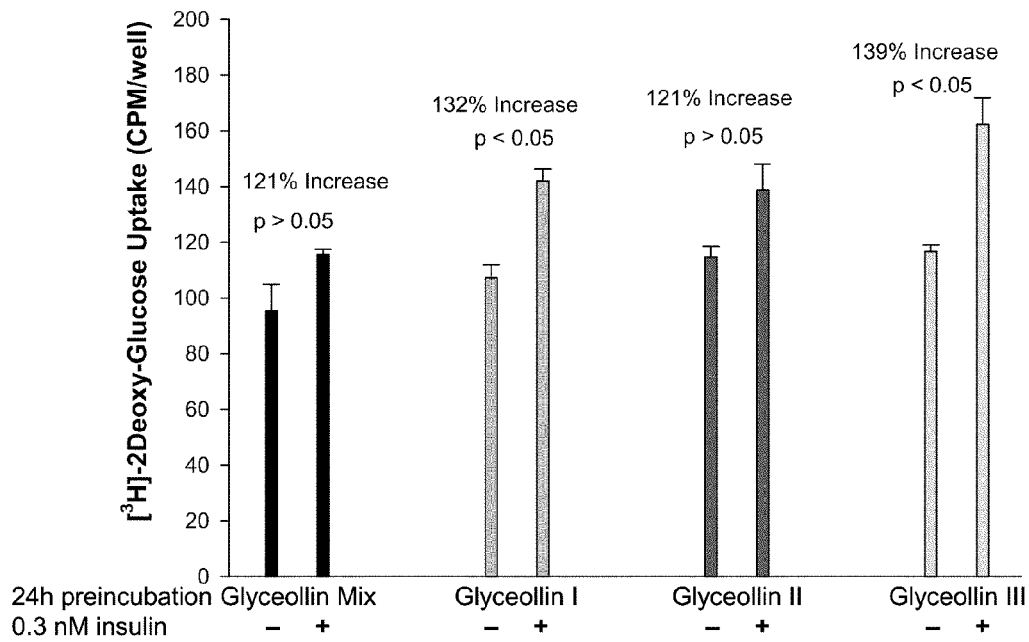
FIG. 15 shows the effects of a 30 minute exposure to insulin on glucose uptake by 3T3-L1 differentiated adipocytes pre-incubated with glyceollin.
Figure 16:
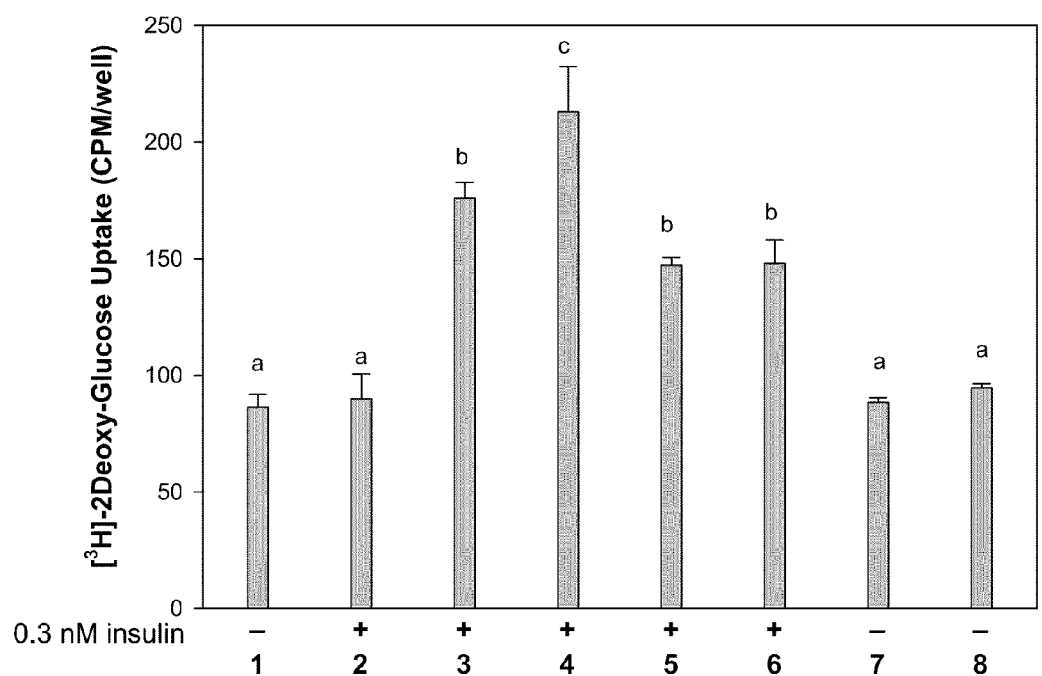
FIG. 16 shows the effects of a 30 minute exposure to glyceollin, insulin, or glycinol on glucose uptake by 3T3-L1 differentiated adipocytes pre-incubated with KRH. Columns are as follows: 1) DMSO control; 2) KRH control; 3) Glyceollin Mix (5 μM); 4) Glyceollin I (5 μM); 5) Glyceollin II (5 μM); 6) Glyceollin III (5 μM); 7) Glycinol (1 μM); 8) Glycinol (0.1 μM). Columns that differ from each other by p<0.05 have differing superscript letters.

To compare the glyceollin mixture (used above, for the prior EXAMPLES) against the individual glyceollins (I, II, and III) that make up that mixture, cells were pre-incubated for 24 hours with either the glyceollin mixture (glyceollins I, II, and III), glyceollin I, glyceollin II, or glyceollin III. As shown in FIG. 15, each of the glyceollins is effective at enhancing insulin-mediated glucose uptake, and it appears that glyceollins I and III are more effective than glyceollin II. The data of FIG. 16 confirm this finding, demonstrating that all three glyceollins enhance insulin-mediated glucose uptake. For the experiments shown in FIG. 16, 3T3-L1 differentiated adipocytes pre-incubated for 24 hours with KRH (serum-starved) were exposed for 30 minutes to 5 µM of glyceollin mixture or individual glyceollins, with insulin, or to glycinol in the absence of insulin. The columns of FIG. 16 are as follows: 1) DMSO control; 2) KRH control; 3) Glyceollin Mix (5 µM); 4) Glyceollin I (5 µM); 5) Glyceollin II (5 µM); 6) Glyceollin III (5 µM); 7) Glycinol (1 µM); 8) Glycinol (0.1 µM). Glyceollin I appears to stimulate glucose uptake better than glyceollins II and III; because the glyceollin mixture contains about 75% glyceollin I, it would be expected to have less activity than purified glyceollin I. Columns 7 and 8 indicate that glycinol does not present the same bioactivity as glyceollin, as demonstrated earlier. Finally, column 1 demonstrates that the DMSO vehicle does not have any effect on glucose uptake.

Example 15

Glyceollins I & III Stimulate Glucose Uptake in the Absence of Insulin

Figure 17:
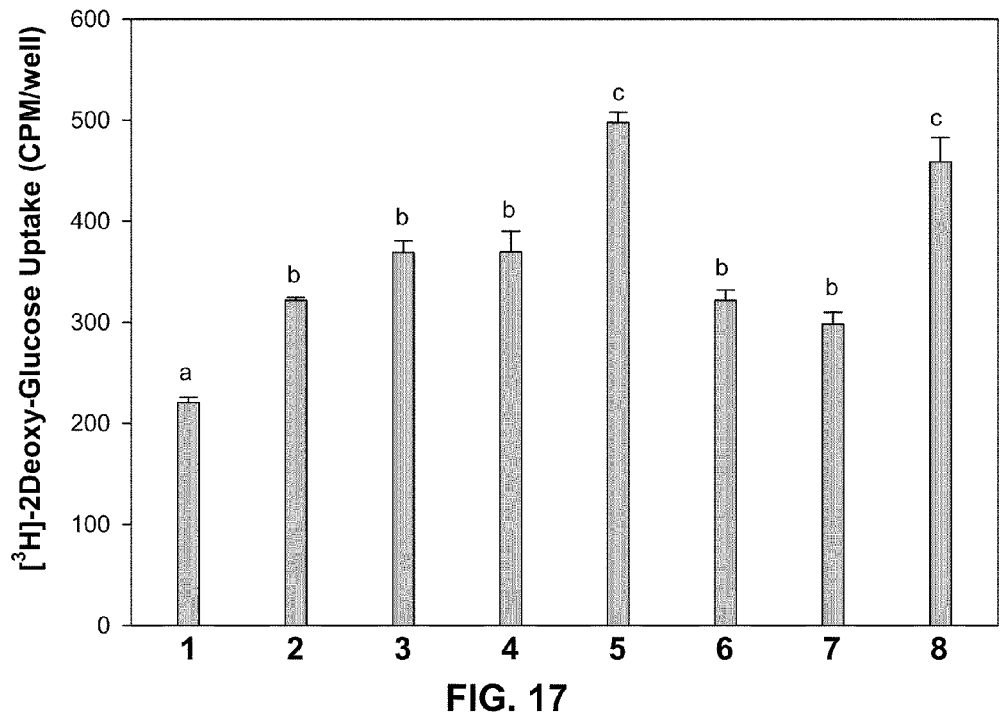
FIG. 17 shows the effects of a 30 minute exposure to either glyceollin I or glyceollin III, with or without insulin, on glucose uptake by 3T3-L1 differentiated adipocytes pre-incubated with KRH. Columns are as follows: 1) DMSO control; 2) 0.3 nM insulin; 3) Glyceollin I (5 μM); 4) 0.3 nM insulin+Glyceollin I (1 μM); 5) 0.3 nM insulin+Glyceollin I (5 μM); 6) Glyceollin III (5 μM); 7) Glyceollin I (1 μM); 8) 0.3 nM insulin+Glyceollin III (5 μM). Columns that differ from each other by p<0.05 have differing superscript letters.

Cells were pre-incubated (serum starved) for 24 hours in KRH, then exposed to glyceollins I or III in either the presence or absence of insulin. The data of FIG. 17 demonstrate that both glyceollins I and III can stimulate glucose uptake in the absence of insulin, but that glucose uptake is further enhanced after addition of insulin. The columns of FIG. 17 are as follows: 1) DMSO control; 2) 0.3 nM insulin; 3) Glyceollin I (5 µM); 4) 0.3 nM insulin+Glyceollin I (1 µM); 5) 0.3 nM insulin+Glyceollin I (5 µM); 6) Glyceollin III (5 µM); 7) Glyceollin I (1 µM); 8) 0.3 nM insulin+Glyceollin III (5 µM). Columns that differ from each other by p<0.05 have differing superscript letters.

Example 16

Response of 3T3-L1 Differentiated Adipocytes to Very Low Doses of Insulin

Figure 18:
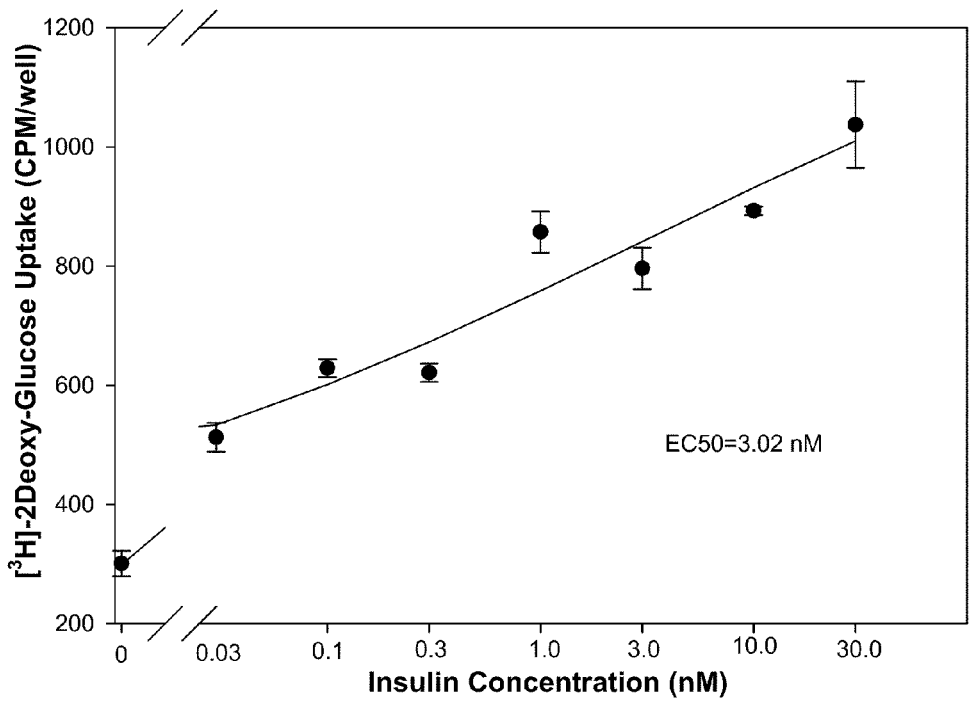
FIG. 18 is a dose-response curve, generated using a rapid-pipetting technique, showing insulin-mediated glucose uptake by 3T3-L1 adipocytes.

The experiments described for EXAMPLE 11 were repeated using lower concentrations of insulin. The dose-response curve of FIG. 18 shows the effects of very low insulin concentrations on glucose uptake in 3T3-L1 differentiated adipocytes.

Example 17

Glucose Uptake After 19 Hours Pre-Incubation with Glyceollin Mixture

Figure 19:
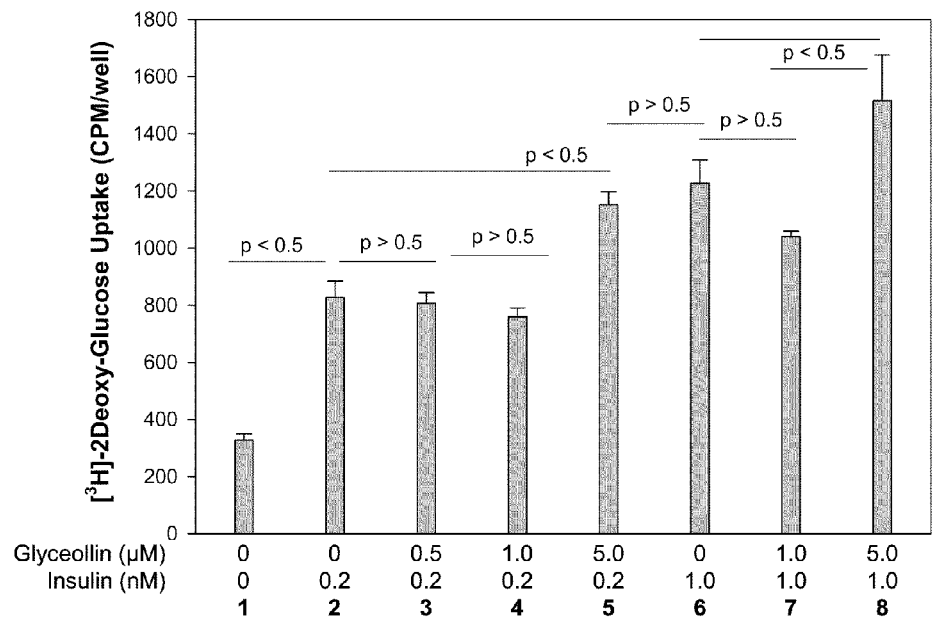
FIG. 19 shows the effects of a 30 minute exposure to insulin on glucose uptake by 3T3-L1 differentiated adipocytes pre-incubated for 24 hours with either KRH or with glyceollin.
Figure 20:
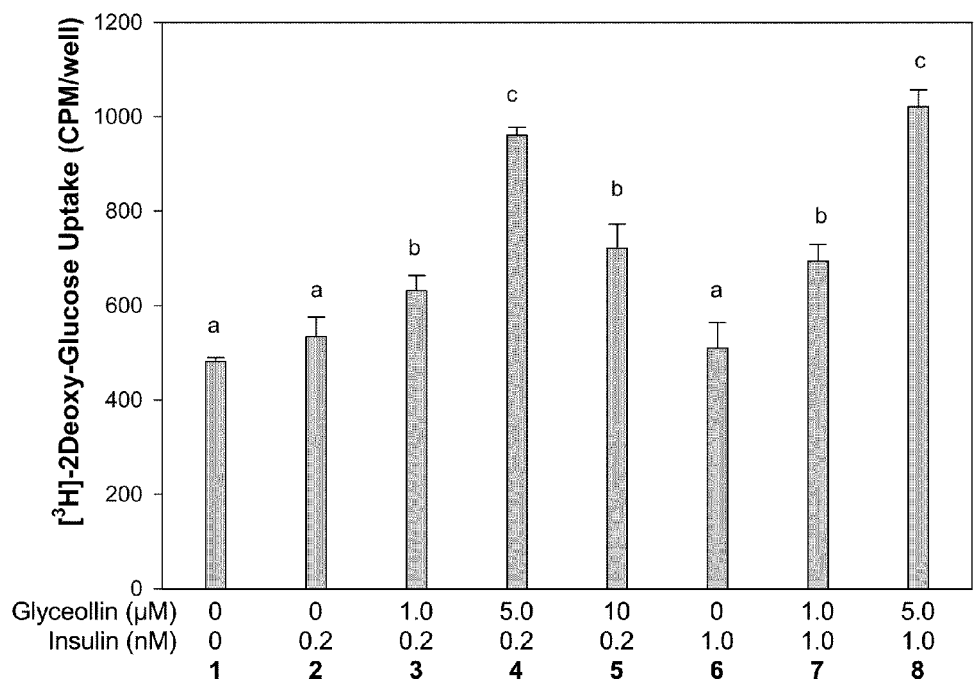
FIG. 20 shows the effects of a 30 minute exposure to insulin on glucose uptake by 3T3-L1 differentiated adipocytes pre-incubated for 3 hours with either KRH or with glyceollin. Columns that differ from each other by p<0.05 have differing superscript letters.

3T3-L1 differentiated adipocytes were pre-incubated for 19 hours with either KRH or with the glyceollin mixture (glyceollins I, II, and III) at the concentrations indicated. Cells were then washed and challenged with insulin at the concentrations indicated, and the results are shown in FIG. 19. Column 2 demonstrates stimulation of glucose uptake by 0.2 nM insulin alone (compare columns 1 & 2). Columns 3, 4, and 5 indicate that 5 µM glyceollin is required to further stimulate glucose uptake (i.e., that 0.5 and 1.0 µM glyceollin concentrations are insufficient). Column 6 demonstrates a maximal insulin dose (1 nM), and bar 8 demonstrates that preincubation with glyceollin (5 µM) enhances glucose uptake even further. These data suggest are surprising because it has not been known that glyceollin can stimulate glucose uptake beyond that of a high insulin dose. These data also suggest that glyceollin does not enhance insulin sensitivity, but rather stimulates glucose uptake via an insulin-independent mechanism. The experiment was repeated with pre-incubation of only 3 hours (instead of 19 hours), and the data show that a 3-hour pre-incubation with glyceollin mixture is sufficient to stimulate glucose uptake to a level above that achieved with insulin alone (FIG. 20).

Example 18

Glucose Uptake After 45 Minutes Pre-Incubation with Glyceollin Mixture

Figure 21:
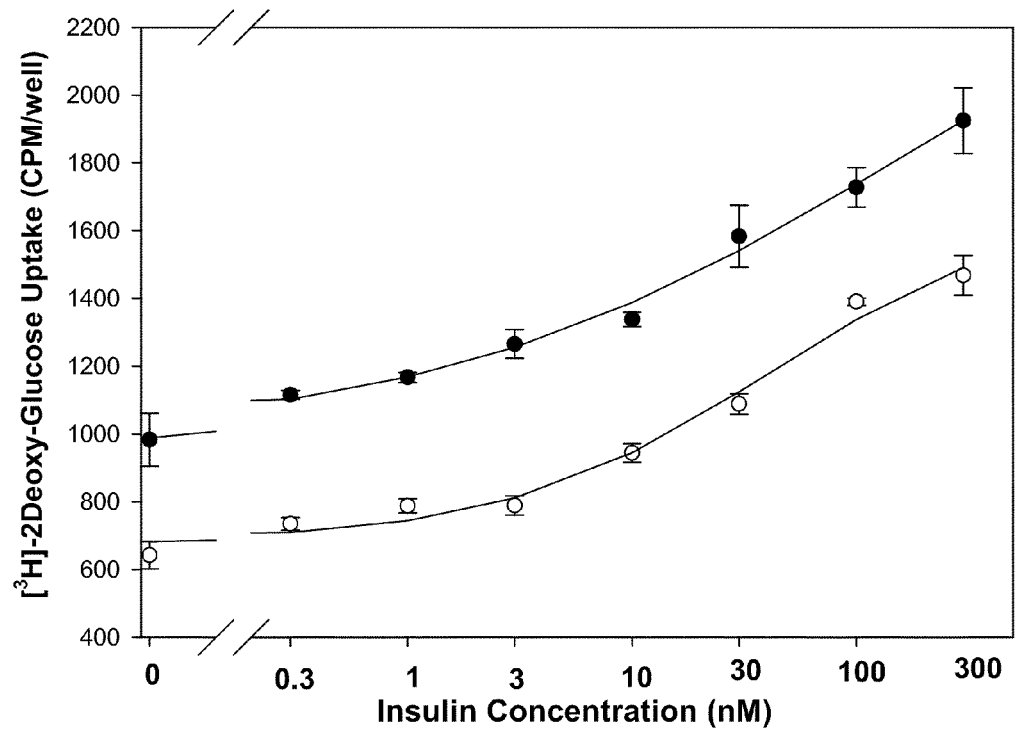
FIG. 21 shows insulin-mediated glucose uptake by 3T3-L1 differentiated adipocytes after 45 minutes of exposure to either glyceollin (●) or KRH buffer (○). Means are significantly different at all insulin concentrations (p<0.05).

3T3-L1 differentiated adipocytes were exposed to either KRH for 45 minutes (see FIG. 21, "○") as a control, or to a 5 µM glyceollin mixture (see FIG. 21, "●"), then challenged with different doses of insulin to generate a dose-response curve as described above (see, e.g., EXAMPLE 11); the results are presented in FIG. 21. Unlike the serum-starvation experiments above, this study did not involve removing serum for 24 hours; the purpose was to create an insulin-insensitive system to determine whether glyceollin would increase insulin sensitivity. The response observed when cells are pre-incubated with KRH is very much blunted and insulin-insensitive, as shown by the open circles (○) and compared to the insulin dose-response curves generated after an overnight medium switch (24-hour serum starvation; see FIG. 18). If glyceollin increases insulin sensitivity, as commonly supposed, then the insulin dose-response curve of FIG. 21 should be shifted to the left. It was not; glucose uptake increased significantly at all insulin challenge levels. This indicates that glyceollin must stimulate glucose uptake via a mechanism that is independent of insulin. Because insulin-mediated glucose uptake is mediated by the GLUT4 transporter, and since these cells have a GLUT 1 transporter (this is believed to be responsible for basal glucose uptake), it appears likely that glyceollin does not increase insulin sensitivity by altering GLUT 4 but rather increases basal glucose uptake via GLUT 1.

Example 19

Glyceollin-Stimulated Glucose Uptake in the Absence of Insulin

Figure 22:
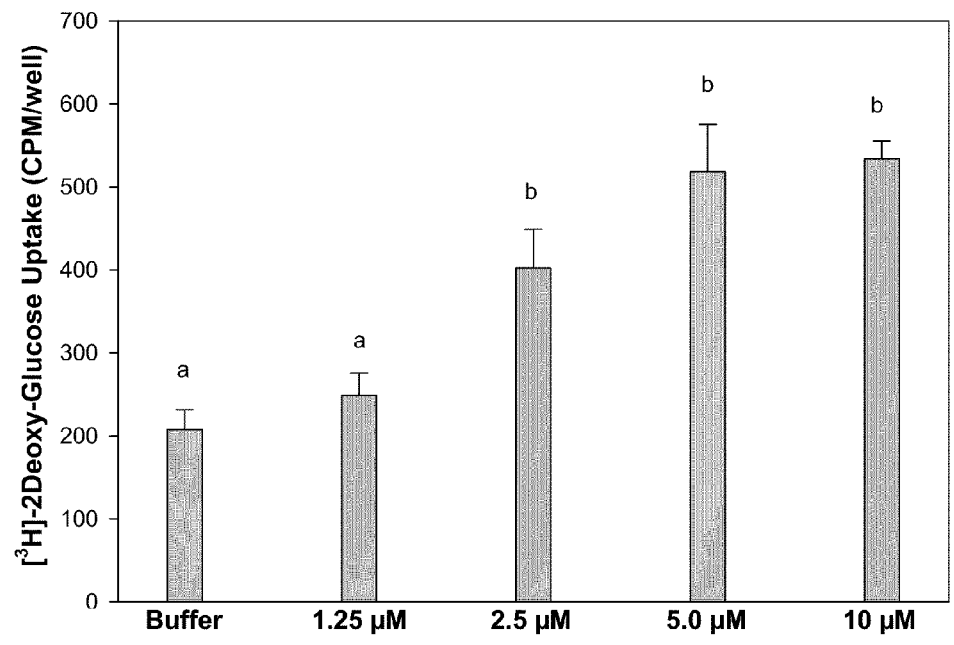
FIG. 22 shows glucose uptake by 3T3-L1 differentiated adipocytes preincubated for 24 hours with KRH, then incubated 45 minutes with different doses of glyceollin, and then 30 minutes with KRH. Columns that differ from each other by p<0.05 have differing superscript letters.

3T3-L1 differentiated adipocytes were pre-incubated (serum-starved) for 24 hours in KRH to starve the cells of glucose and insulin, as demonstrated earlier. This provides a very sensitive assay for glucose uptake. The cells were then incubated for 45 minutes with various concentrations of the glyceollin mixture, washed, and then incubated in KRH for an additional 30 minutes. As demonstrated in FIG. 22, glyceollin mixture alone stimulates basal glucose uptake in an insulin-independent manner.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method of treating hyperlipidemia, obesity, excessive cholesterol, diabetes, or combinations thereof, in an animal in need thereof, comprising administering a composition comprising at least one isolated glyceollin to said animal, wherein said isolated glyceollin is present in said composition in an amount of from about 100 nM to about 50 µM.

2. The method of claim 1, wherein said at least one isolated glyceollin is isolated from elicited soy, and is glyceollin I, glyceollin II, glyceollin III, or combinations thereof.

3. The method of claim 2, wherein said at least one isolated glyceollin is provided in an amount of from about 1 mg/kg/animal to about 100 mg/kg/animal.

4. A method of stimulating glucose uptake in an animal in need thereof, comprising administering a composition comprising at least one isolated glyceollin to said animal wherein said at least one isolated glyceollin is provided in a concentration of from about 100 nM to about 50 μM.

5. The method of claim 4, wherein said at least one isolated glyceollin is isolated from elicited soy, and is glyceollin I, glyceollin II, glyceollin III, or combinations thereof.

6. The method of claim 4, wherein said composition further comprises insulin, or wherein a further composition comprising insulin is also administered to said animal.

7. A method of stimulating glucose uptake in an animal in need thereof, comprising administering a composition comprising at least one isolated glyceollin to said animal wherein said at least one isolated glyceollin is provided in an amount of from about 1 mg/kg/animal to about 100 mg/kg/animal.

8. The method of claim 7, wherein said at least one isolated glyceollin is isolated from elicited soy, and is glyceollin I, glyceollin II, glyceollin III, or combinations thereof.

9. The method of claim 7, wherein said composition further comprises insulin, or wherein a further composition comprising insulin is also administered to said animal.

* * * * *